United States Patent
Garneau-Tsodikova et al.

(10) Patent No.: US 10,208,000 B2
(45) Date of Patent: Feb. 19, 2019

(54) EIS INHIBITORS

(71) Applicants: University of Kentucky Research Foundation, Lexington, KY (US); The United States of America, as represented by the Secretary, Department of Health and Human Services, Rockville, MD (US)

(72) Inventors: Sylvie Garneau-Tsodikova, Lexington, KY (US); Oleg V. Tsodikov, Lexington, KY (US); James E. Posey, Rockville, MD (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/381,901

(22) Filed: Dec. 16, 2016

(65) Prior Publication Data

US 2017/0174639 A1 Jun. 22, 2017

Related U.S. Application Data

(60) Provisional application No. 62/268,244, filed on Dec. 16, 2015.

(51) Int. Cl.
| | |
|---|---|
| *C07D 241/44* | (2006.01) |
| *A61K 31/498* | (2006.01) |
| *A61K 31/7036* | (2006.01) |
| *A61K 45/06* | (2006.01) |

(52) U.S. Cl.
CPC .......... *C07D 241/44* (2013.01); *A61K 31/498* (2013.01); *A61K 31/7036* (2013.01); *A61K 45/06* (2013.01)

(58) Field of Classification Search
CPC .................................................. C07D 241/44
See application file for complete search history.

(56) References Cited

U.S. PATENT DOCUMENTS

| | | | |
|---|---|---|---|
| 5,852,016 A | 12/1998 | Faye et al. | |
| 5,912,245 A | 6/1999 | Rivó et al. | |
| 6,096,744 A | 8/2000 | Kornberg et al. | |
| 8,642,660 B2 * | 2/2014 | Goldfarb | A61K 31/122 514/18.9 |
| 9,108,953 B2 | 8/2015 | Babaoglu et al. | |
| 2009/0163545 A1 * | 6/2009 | Goldfarb | A61K 31/122 514/312 |

FOREIGN PATENT DOCUMENTS

WO WO2015/080707 6/2015

OTHER PUBLICATIONS

Olayiowla, G. et al., Synthesis and neuropharmacological activity of some quinoxalinone derivatives African Journal of Biotechnology (2007), 6(6), 777-786 CODEN: AJBFAH; ISSN: 1684-5315 URL: http://www.academicjournals.org/AJB/PDF/pdf2007/19Mar/Olayiwola%20et%20al.pd f; English.*

Garzan, et al., Sulfonamide-Based Inhibitors of Aminoglycoside Acetyltransferase Eis Abolish Resistance to Kanamycin in *Mycobacterium tuberculosis*; J. Med. Chem. 2016, 59, 10619-10628.

Garzan, et al., Supporting Information for Sulfonamide-Based Inhibitors of Aminoglycoside Acetyltransferase Eis Abolish Resistance to Kanamycin in *Mycobacterium tuberculosis*; J. Med. Chem. 2016, 59, S1-S9.

* cited by examiner

*Primary Examiner* — Paul V Ward
(74) *Attorney, Agent, or Firm* — Mandy Wilson Decker; Stites & Harbison PLLC

(57) ABSTRACT

Provided herein are novel small-molecules that have use in the inhibition of Eis, which mediates kanamycin resistance in *Mycobacterium tuberculosis*. The presently-disclosed subject matter further includes a pharmaceutical composition including a small molecule inhibitor, as described herein, and a suitable pharmaceutical carrier. Methods of treating tuberculosis comprising administering to an individual an effective amount of the disclosed small molecule inhibitors to mediate kanamycin A resistance and treat tuberculosis are also provided.

16 Claims, 5 Drawing Sheets

US 10,208,000 B2

EIS INHIBITORS

RELATED APPLICATIONS

This application claims priority from U.S. Provisional Application Ser. No. 62/268,244, filed Dec. 16, 2015, the entire disclosure of which is incorporated herein by this reference.

GOVERNMENT INTEREST

This invention was made with government support under National Institutes of Health (NIH) Grant AI090048. The government has certain rights in the invention.

TECHNICAL FIELD

The presently-disclosed subject matter relates to compositions useful as inhibitors of acetyltransferase Eis, a mediator of kanamycin resistance in *Mycobacterium tuberculosis*, and their methods of use. In particular, the compositions are sulfonamide-based and sulfonyl isothiazole-based small molecules.

INTRODUCTION

A major cause of tuberculosis (TB) resistance to the aminoglycoside kanamycin (KAN) is the *Mycobacterium tuberculosis* (Mtb) acetyltransferase Eis. Eis is a super-acetyltransferase from *M. tuberculosis* that inactivates all clinically used aminoglycosides. Upregulation of Eis is a frequent cause of clinical resistance to the aminoglycoside kanamycin (KAN) in TB. Upregulation of this enzyme is responsible for inactivation of KAN through acetylation of its amino groups.

Tuberculosis (TB) is an infectious disease caused by *Mycobacterium tuberculosis* (Mtb), and a major global health threat. In 2013, approximately 9.0 million people developed TB, and nearly 1.5 million died from the disease. Due to the spread of multidrug-resistant TB (MDR TB), defined as TB with resistance to at least isoniazid and rifampin (~10% of new TB cases in 2013) and extensively drug-resistant TB (XDR TB), defined as MDR TB with added resistance to at least a fluoroquinolone and an injectable drug (i.e., kanamycin (KAN), capreomycin, or amikacin), the need for novel strategies to combat drug resistant TB is urgent.

The aminoglycosides (AGs) kanamycin A (KAN) and amikacin (AMK) are used to treat MDR- and XDR-TB, but resistance to these agents occurs as well. Among mechanisms of clinically important transmissible drug resistance is the recently identified inactivation of an MDR-TB therapeutic, the aminoglycoside kanamycin, through its acetylation by an upregulated acetyltransferase, the Eis (enhanced intracellular survival) enzyme. We previously demonstrated that the Mtb Eis protein (Eis_Mtb) is an acetyltransferase capable of multiacetylating a variety of AGs, including the TB therapeutics KAN and AMK, via a random sequential mechanism, thereby abolishing the antibiotic activity of these drugs. The ability of acetylating an AG molecule at multiple amine positions due to its unique structure distinguishes Eis from other AG acetyltransferases (AACs), which are known to be exquisitely regiospecific. A crystal structure of Eis_Mtb in complex with coenzyme A and tobramycin demonstrated how tobramycin could interact with the Eis active site in two binding modes for the observed diacetylation of the 6'- and 3"-amines of this AG.

Multiacetylation by Eis has a defined pattern for each AG: the number of acetylations and the positions of the amino groups that get acetylated depend on the structure of the AG. Furthermore, Eis homologues from *Mycobacterium smegmatis*, *Mycobacterium abscessus*, *Anabaena variabilis*, *Bacillus anthracis*, *Gordonia bronchialis*, *Kocuria rhizophila* (9), and *Tsukamurella paurometabola* are also functional AACs, which exhibit differences in regiospecificity and can be inhibited by chlorhexidine, a non-clinically relevant Eis_Mtb inhibitor. In addition to AG substrate versatility, Eis enzymes display some acyl-CoA co-substrate promiscuity and can acetylate non-AG molecules containing lysine residues, such as capreomycin and the JNK-specific dual-specificity protein phosphatase 16 (DUSP16)/mitogen-activated protein kinase phosphatase-7 (MKP-7) pair. These observations underscore the uniqueness and versatility of Eis AG modifying activity and its high capacity for inactivation of diverse AG drugs.

The development of AGs that cannot be modified by Eis or a novel therapy that would involve an Eis inhibitor used in combination with KAN are two possible approaches to resolve the need in the field of drug resistant tuberculosis. The former route is complicated by the ability of Eis to accept structurally diverse AGs as substrates, whereas the latter route is potentially more suitable. The latter approach to combat drug resistance arising as a result of drug-modifying enzymes, then, is to use a combination therapy that includes an antibiotic along with an inhibitor of its associated resistance enzyme. In Mtb, including MDR TB, the combination of the β-lactamase inhibitor clavulanate and the β-lactam meropenem was demonstrated to overcome resistance to β-lactam antibiotics. With this strategy in mind, efforts have also been made towards identifying inhibitors of aminoglycoside acetyltransferases (AACs) present in non-mycobacteria, with limited pre-clinical progress, but these are not applicable for the mechanistically and structurally distinct Mtb Eis acetyltransferase. For example, aminoglycoside-acetyl coenzyme A bi-substrate inhibitors were found to potently inhibit AAC(6') enzymes in vitro, but were not effective in cell-based assays. Numerous cationic peptides that inhibit AAC(6') enzymes in vitro were identified, but these also displayed no antibacterial effects against resistant bacterial strains due to membrane permeability issues. Finally, the natural product aranorosin was found to be an inhibitor of the bi-functional AAC(6')-Ie/APH(2")-Ia enzyme, and its combination with the aminoglycoside arbekacin was shown to stop the growth of a methicillin-resistant *Staphylococcus aureus* strain.

We previously reported that some Eis inhibitors displayed AG-competitive and mixed modes of action, establishing a proof of principle for inhibition of Eis in vitro.

A two-drug combination therapy where one drug targets an offending cell and the other targets a resistance mechanism to the first drug is a time-tested, yet underexploited approach to combat or prevent drug resistance in an infectious disease. Furthermore, there remains a need for approaches to combat drug resistant TB.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes compositions useful as inhibitors of acetyltransferase Eis, a mediator of kanamycin resistance in *Mycobacterium tuberculosis*, and their methods of use. In particular, the compositions are sulfonamide-based and sulfonyl isothiazole-based small molecules. In some embodiments, the inhibitors can effectively overcome kanamycin resistance in strains of Mtb.

In some embodiments, the compositions are a compound of the formula:

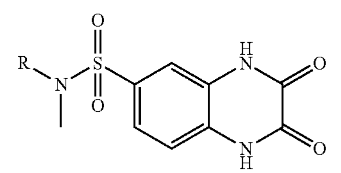

wherein R is selected from the group consisting of

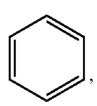

, 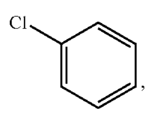 , 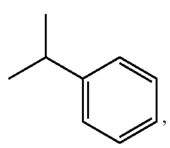 ,

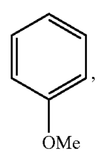

, 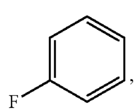 , 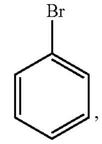 , 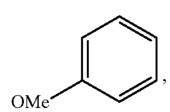 ,

, 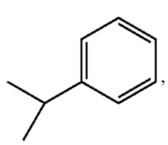 , 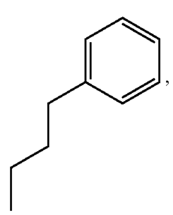 ,

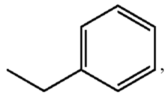

, 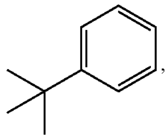 ,

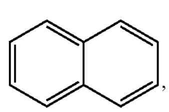

, and 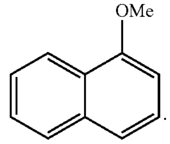 .

In some embodiments, the compounds is of the formula of any one of compounds 33-47, as set forth in Table 1B herein.

In some embodiments, the compounds are included in a pharmaceutical composition. In some embodiments, the pharmaceutical composition includes the compounds of the present invention and a suitable pharmaceutical carrier. In some embodiments, compositions and pharmaceutical compositions include the small molecule compounds set forth herein, such as for example, the compounds in Tables 1B, 4 and 5, a suitable pharmaceutical carrier, and an aminoglycoside. In some embodiments, the aminoglycoside is kanamycin (KAN).

Methods of using the Eis inhibitors are also disclosed. In some embodiments, methods of inhibiting Eis include administering an effective amount of a composition including the compounds disclosed herein, including those set forth in Tables 1B, 4, or 5 is disclosed. In some embodiments, such methods include administration of a compound selected from compounds 29, 30, 32-35, 37-39, 41, 43, and 46 in Table 1B.

In some embodiments, the compound is according to the formula:

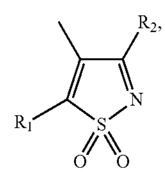

wherein the R1 and R2 groups are according to the structures identified in Table 5 as 3i, 6b, 7b, 8a, 8e, 11c, 12e, 13a, 13e, 13g, 13i, 14c, 15e, 15f, 17i, 33a, 35e, 35g, 35h, 35i, 36d, 37b, 37d, 46a, 46b, 46c, 46h, 52i, 62i, 81b, 81g, 87b, 89b, 112b, 112i, 115i, 116i, 139b, 139e, and 139i. In some embodiments, Eis inhibition is effectuated by administration of the disclosed compounds.

In one aspect, the administration of the disclosed compound yields a Minimal Inhibitory $Concentration_{Kanamycin}$ ($MIC_{KAN}$) value is less than about 2.5 μg/mL to about 5 μg/mL to a Mtb strain. In some embodiments, the MIC level is reduced to a level close to a KAN-susceptible Mtb strain, and can be characterized as fully overcoming kanamycin resistance. In some embodiments, the $IC_{50}$, that is, the concentration of an inhibitor's Eis inhibitory activity is increased. In some embodiments, the $IC_{50}$ is about 0.08 μM to about 0.25 μM against purified Eis enzyme, in other embodiments, the $IC_{50}$ is less than about 0.25 μM.

Methods of administration can include, in some embodiments, administering an aminoglycoside or a combination of drugs including an aminoglycoside. In some embodiments, the aminoglycoside is kanamycin (KAN).

Methods of treating aminoglycoside-resistant *Mycobacterium tuberculosis* are also disclosed and include administering the compounds of the present invention, including compounds as set forth in Tables 1B, 4 and 5. In some embodiments, such methods of treatment include administering an aminoglycoside, before, during or after treatment with the compounds of the present invention. In some embodiments, the aminoglycoside is administered with a combination of other active drugs. In some instances, the aminoglycoside is kanamycin (KAN). In one aspect, the methods of treatment include administering the aminoglycoside and presently-disclosed compounds to a subject in need of treatment for aminoglycoside-resistant Mtb.

A kit including the compounds as disclosed herein, for example, a compound as set forth in Tables 1B, 4 and 5, packaged together with an aminoglycoside are also disclosed. In some embodiments, the kit contains the aminoglycoside kanamycin.

BRIEF DESCRIPTION OF THE DRAWINGS

The novel features of the subject matter of the present disclosure are set forth with particularity in the following description and in the appended sample claims. A better understanding of the features and advantages of the presently disclosed subject matter will be obtained by reference to the following detailed description that sets forth illustrative embodiments, in which the principles of the invention(s) are used, and the accompanying drawings.

FIG. 2 is a cartoon view of the crystal structure of Eis in complex with compound 39 and CoA.

DESCRIPTION OF EXEMPLARY EMBODIMENTS

Figure 1:
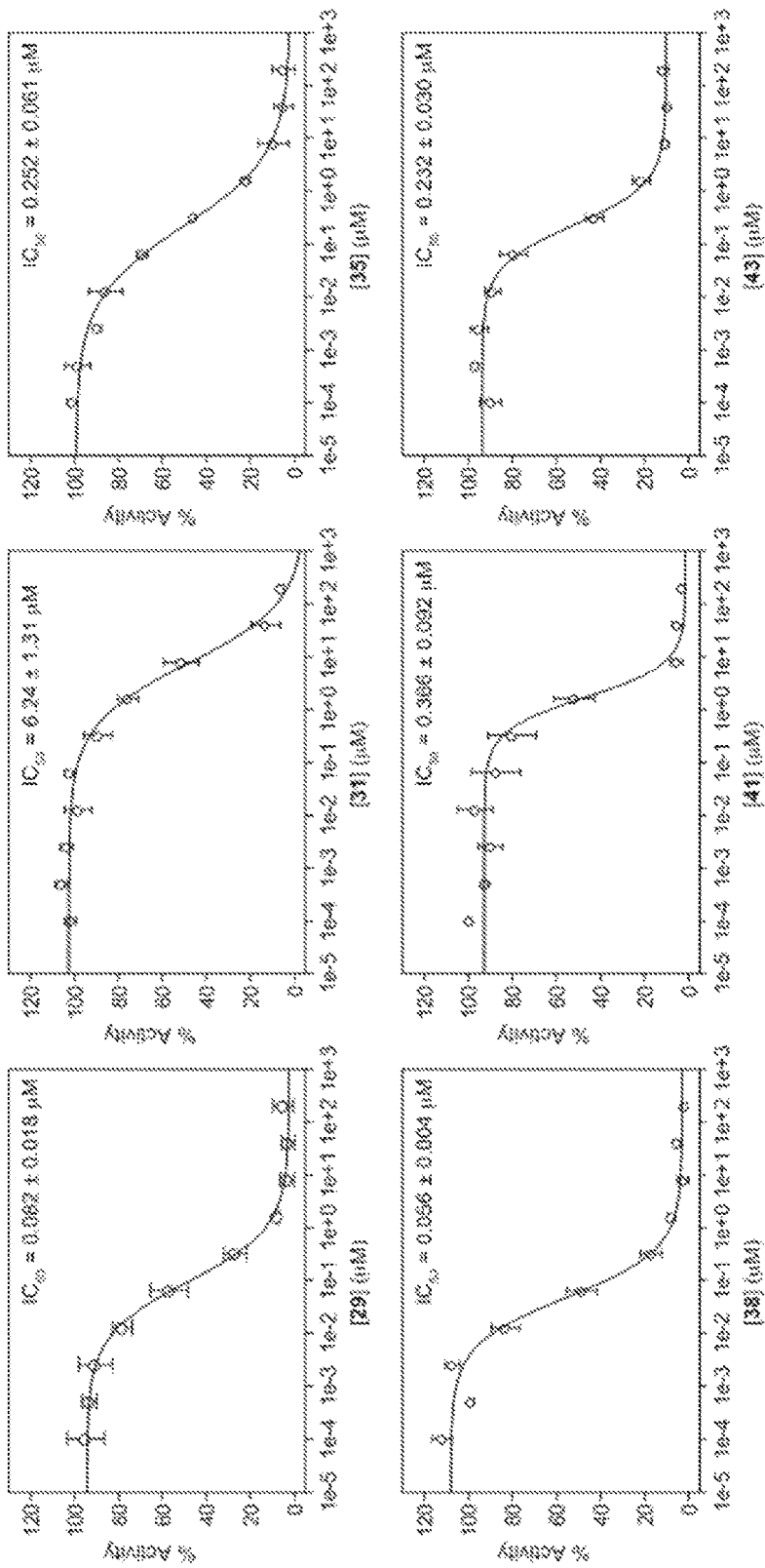
FIG. 1 shows representative dose response curves for sulfonamide inhibitors of the present invention with pure Eis.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is illustrated by specific but non-limiting examples throughout this description. The examples may include compilations of data that are representative of data gathered at various times during the course of development and experimentation related to the present invention(s). Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The presently-disclosed subject matter includes compounds that are useful for inhibiting Eis. In some embodiments, the compound has the following structure:

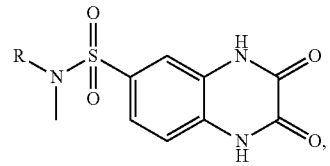

where R is defined as set forth in Table 1B, hereinbelow. In some embodiments, the compound is any one of compounds 33-47, as set forth in Table 1B. In some embodiments, the compound has the following structure:

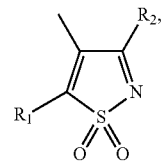

where $R_1$ and $R_2$ are defined as set forth in Tables 4 and 5.

The presently-disclosed subject matter also includes compositions comprising one or more of compounds as set forth in Table 1B. In some embodiments, the composition includes one or more of compounds 33-47, as set forth in Table 1B. In some embodiments, the composition includes one or more compounds as set forth in Tables 1B, 4, and 5. In some embodiments, the composition includes one or more compounds identified in Table 5 as 3i, 6b, 7b, 8a, 8e, 11c, 12e, 13a, 13e, 13g, 13i, 14c, 15e, 15f, 17i, 33a, 35e, 35g, 35h, 35i, 36d, 37b, 37d, 46a, 46b, 46c, 46h, 52i, 62i, 81b, 81g, 87b, 89b, 112b, 112i, 115i, 116i, 139b, 139e, and 139i. In some embodiments, the composition is a pharmaceutical composition further comprising a pharmaceutically-acceptable carrier.

The presently-disclosed subject matter further includes methods or inhibiting Eis and methods of treating aminoglycoside-resistant Mtb. In some embodiments the method involves administering a compound or composition as disclosed herein. In some embodiments, the method involves administering a compound or composition to a subject in need of treatment for aminoglycoside-resistant Mtb. In some embodiments, the method further includes administering an aminoglycoside. In some embodiments the aminoglycoside is kanamycin (KAN).

The terms "treat," "treatment," and the like refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative (prophylatic) treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

In some embodiments, a method is provided for treating antibiotic resistance and/or inhibiting Eis enzymatic activity in a cell. In some embodiment the method includes contacting the cell with compounds disclosed herein. The term "contacting" as used herein refers to any means by which the compound is brought into sufficient proximity and/or in direct contact with a cell such that the cell is capable of receiving the compound. For instance, in some embodiments contact refers to coating or otherwise exposing a cell to the compound. In some embodiments contact refers to culturing a cell in a solution that includes the compound. In other embodiments the cell is within a subject, and contact refers to administering a compound to the subject such that a cell within the subject is capable of receiving the novel small molecule compounds. In some embodiments, such methods can include further administration of an antibiotic at the same time as the administration of the compound, or prior to or subsequent to the administration of compound. In some embodiments, the antibiotic is kanamycin. The presently-disclosed subject matter further includes composition that include at least one compound disclosed herein as an Eis inhibitor, and an aminoglycoside. In some embodiments the aminoglycoside is kanamycin (KAN). In some embodiments, the cell exhibits resistance to kanamycin. In some embodiments, said cell is within a subject diagnosed with tuberculosis.

The presently-disclosed subject matter further includes kits comprising at least one compound disclosed herein as an Eis inhibitor, packaged together with an aminoglycoside. In some embodiments the aminoglycoside is kanamycin (KAN).

The presently disclosed subject matter includes identified potent inhibitors of Eis enzymatic activity with resulting sensitization of KAN-resistant Mtb cells, in which the resistance to KAN is caused by Eis upregulation. The inhibitors bind in the AG binding pocket blocking the access of AGs to the active site of the enzyme. The inhibitor binding is accompanied by induced-fit conformational changes of the protein. These compounds have a great potential for further development as KAN adjuvants in Mtb.

The presently-disclosed subject matter includes novel small molecule compositions, and small molecule compositions useful as inhibitors of Eis enzymatic activity. In some instances, the small molecule is a sulfonamide-based structure. In some embodiments, the small molecule is a sulfonyl isothiazole-based composition. In some embodiments, the inhibitors can effectively overcome kanamycin resistance in strains of Mtb.

In one aspect, the administration of the disclosed compound yields a Minimal Inhibitory Concentration$_{Kanamycin}$ ($MIC_{KAN}$) value is less than about 2.5 µg/mL for Mtb strains. In some embodiments, the $MIC_{KAN}$ is less than about 0.625 µg/mL for *Mycobacterium tuberculosis* (Mtb) strain H37Rv, or less than about 5 μg/mL for Mtb strain K204. In some embodiments, the MIC level is reduced to a level close to a KAN-susceptible Mtb strain, and can be characterized as fully overcoming kanamycin resistance. For example, in Mtb strain K204, a measured $MIC_{KAN}$ of less than or equal to 1.25 μg/mL would indicate a compound with inhibitory activity sufficient to overcome kanamycin resistance. As such, in some embodiments, the KAN MIC values of a compound are expressed as a 2-fold, four fold, 8-fold or more reduction in KAN MIC against a Mtb strain.

In some embodiments, the $IC_{50}$, the concentration of an inhibitor's Eis inhibitory activity is measured. In some embodiments, the $IC_{50}$ is about 0.08 μM to about 0.25 μM against purified Eis enzyme. However, as one skilled in the art will recognize, compounds can reduce the MIC value of a KAN-resistant Mtb strain with $IC_{50}$ values that vary according to how measured. For example, in vitro measurements differ from those values measured in cellulo or in vivo. For example, $IC_{50}$ values ranging from 0.1 to about 4.35 μM when measured in cellulo or in vivo can be indicative of an effective Eis inhibitor, as these activities are not exactly correlated. Such variances can be for a wide variety of reasons, including, for example, based upon difficulty of small molecules penetrating the waxy cell wall of Mycobacteria.

Methods of treating kanamycin resistance are also disclosed herein, comprising administering a small molecule composition disclosed herein. Also provided are methods of treating tuberculosis comprising administering the Eis inhibitors disclosed herein with kanamycin. The presently-disclosed subject matter further includes a pharmaceutical composition including a small molecule, as described herein, and a suitable pharmaceutical carrier. The presently-disclosed subject matter also includes a method of treating a bacterial infection comprising administering to an individual an effective amount of a small molecule Eis inhibitor, as disclosed herein. In some instances, the pharmaceutical composition is administered with an aminoglycoside. In some instances the aminoglycoside is Kanamycin.

While the following terms used herein are believed to be well understood by one of ordinary skill in the art, definitions are set forth to facilitate explanation of the presently-disclosed subject matter.

The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

Unless otherwise indicated, the term "administering" is inclusive of all means known to those of ordinary skill in the art for providing a preparation to a subject, including administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and/or subcutaneous administration. Administration can be continuous or intermittent. A preparation can be administered therapeutically; that is, administered to treat an existing condition of interest. A preparation can be administered prophylactically; that is, administered for prevention of a condition of interest.

In some embodiments a subject will be administered an effective amount of at least one compound and/or composition provided in the present disclosure. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

In some embodiments the subject in need thereof will be suffering or will have been diagnosed tuberculosis and/or related diseases, disorders, pathologies, or conditions.

As used herein, the terms "treatment" or "treating" relate to any treatment of a condition of interest, including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an enzyme" includes a plurality of such enzymes, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As will be recognized by one of ordinary skill in the art, the terms "reduce", "reducer", "reduction", "reducing", "suppression," "suppressing," "suppressor," "inhibition," "inhibiting" or "inhibitor" do not refer to a complete elimination of angiogenesis in all cases. Rather, the skilled artisan will understand that the term "reducing", "suppressing" or "inhibiting" refers to a reduction or decrease in a particular condition. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

As described herein, the presently-disclosed subject matter further includes pharmaceutical compositions comprising at least one enzyme described herein together with a pharmaceutically acceptable carrier.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compositions can be formulated as eye drops. For example, the pharmaceutically acceptable carrier may comprise saline solution or other substances used to formulate eye drop, optionally with other agents. Thus, eye drop formulations permit for topical administration directly to the eye of a subject.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

The presently-disclosed subject matter further includes a kit that can include an enzyme and/or a pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

The presently-disclosed subject matter includes novel small molecules. Also disclosed are small molecules that inhibit Eis. Small molecule Eis inhibitors disclosed herein aid in reducing KAN resistance and/or restoring KAN susceptibility in *Mycobacterium tuberculosis*. The presently-disclosed subject matter further includes a pharmaceutical composition including a small molecule inhibitor, as described herein, and a suitable pharmaceutical carrier, optionally administered with Kanamycin. The presently-disclosed subject matter further includes a method of treating tuberculosis, including aminoglycoside resistant tuberculosis, comprising administering to an individual an effective amount of a small molecule Eis inhibitor, as disclosed herein, to inhibit the Eis acetyltransferase of *Mycobacterium tuberculosis* and reduce KAN resistance and/or restore KAN susceptibility.

In certain embodiments, the present disclosure further provides a method of treating, preventing and/or reducing kanamycin resistance and/or restoring KAN susceptibility in *Mycobacterium tuberculosis*. The method comprises at least the step of administering an effective amount of a small molecule in TABLE 1-continued
A. Synthetic scheme used for the preparation of the molecules generated in this study. B. Structures of molecules used in this study.
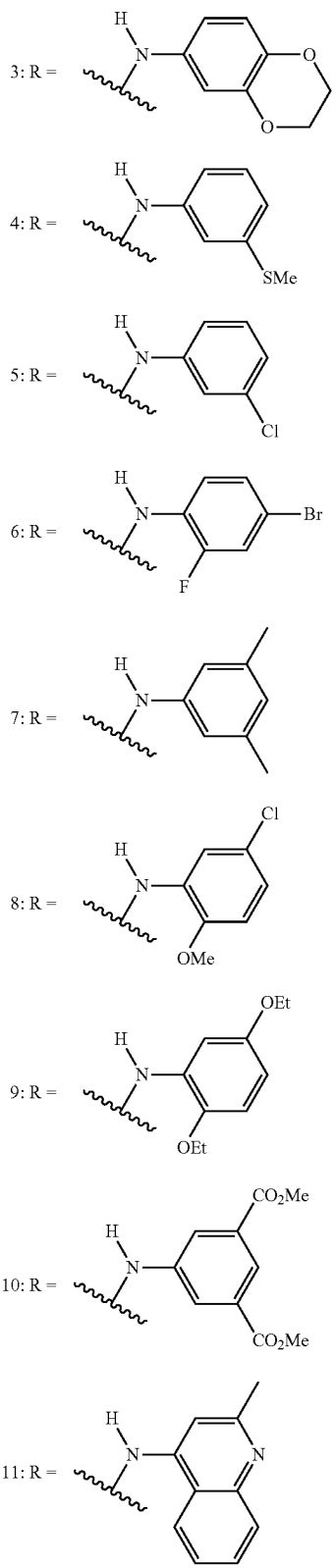
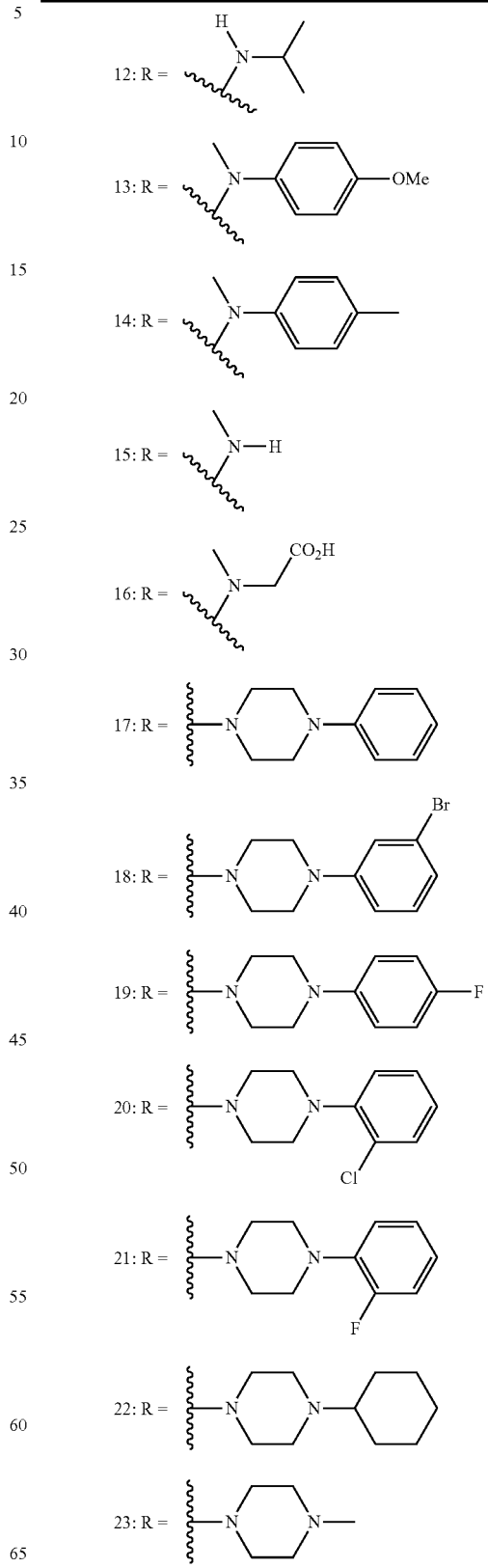

TABLE 1-continued
A. Synthetic scheme used for the preparation of the molecules generated in this study. B. Structures of molecules used in this study.
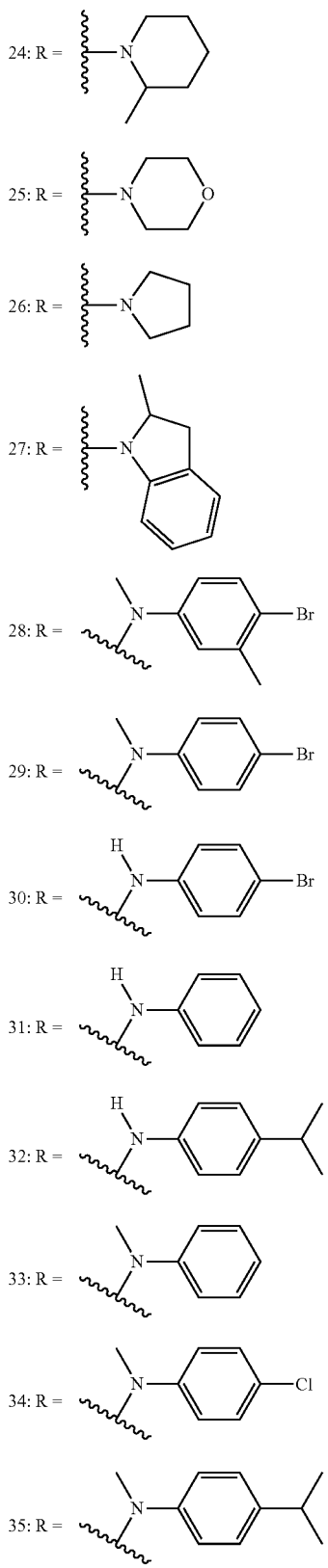
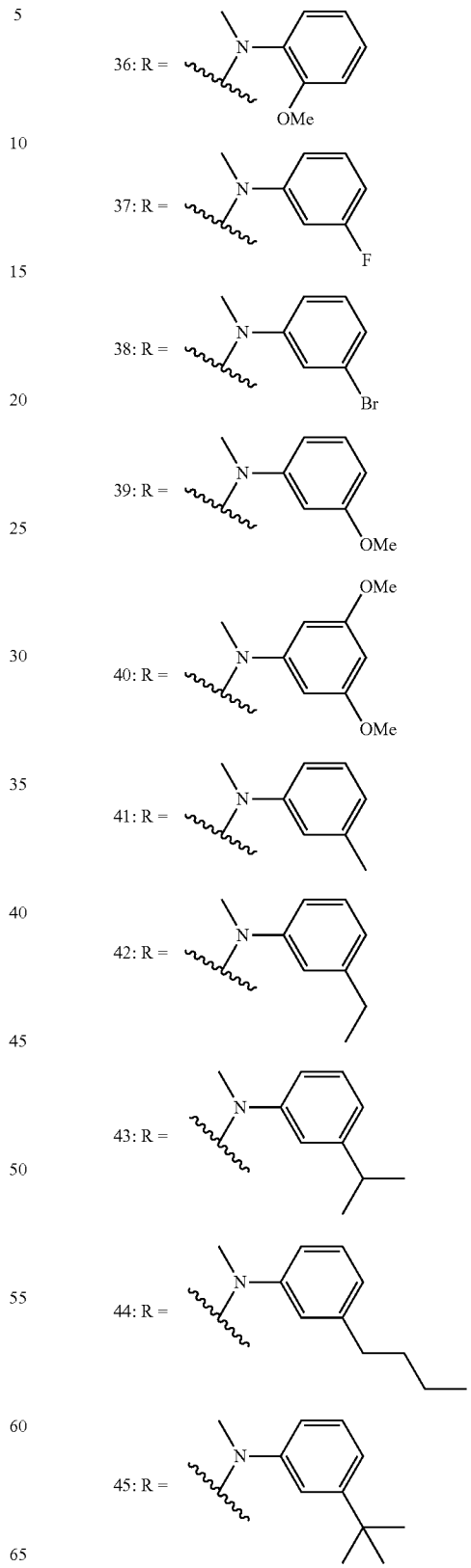

TABLE 1-continued

A. Synthetic scheme used for the preparation of the molecules generated in this study. B. Structures of molecules used in this study.

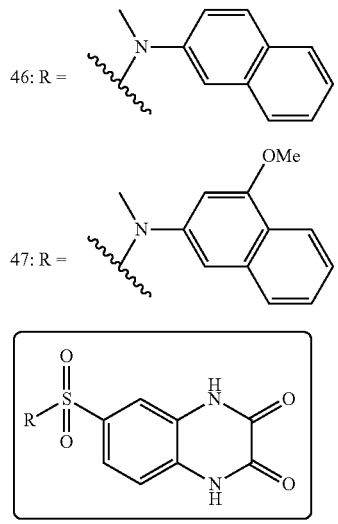

Biochemical and Biological Testing of Sulfonamides 29-47.

To investigate the potential of these compounds as Eis inhibitors for use in combination with KAN, their biochemical ($IC_{50}$ values against purified Eis enzyme) and biological (effect on the MIC values of KAN in KAN-sensitive Mtb H37Rv and in Mtb K204, which is KAN-resistant due to Eis upregulation properties were evaluated in parallel studies (Table 2 and FIG. 1). The freshly synthesized compound 29 displayed robust inhibition of Eis in vitro ($IC_{50}$=0.08±0.02 µM). When combined with KAN, sulfonamide 29, resulted in a four-fold reduced KAN MIC value (2.5 µg/mL) compared to KAN alone (10 µg/mL) for K204 Mtb. This was a reduction almost to the MIC level of KAN in the KAN-susceptible Mtb H37Rv (1.25 µg/mL) parent strain. To gain insight into the importance of the substitution pattern on the aniline portion of the sulfonamide scaffold, secondary (NHAr) and tertiary (N(Me)Ar) sulfonamides (29-47) were first generated. Eis inhibition assays with the synthesized sulfonamides were carried out in combination with KAN. The non-methylated counterpart of lead compound 29, compound 30, displayed lower Eis inhibitory activity ($IC_{50}$=6.24±1.31 µM) and, contrary to 29, did not overcome KAN resistance in Mtb K204 ($MIC_{KAN}$=10 µg/mL). Two other non-methylated derivatives, 31 and 32, also resulted in lower Eis inhibitory activity ($IC_{50}$>200 and 10.6±2.5 µM, respectively) and did not overcome KAN resistance in Mtb K204 ($MIC_{KAN}$=10 and 5 µg/mL, respectively). These data, in conjunction with the fact that compounds 1-12 from the HTS did not display significant Eis inhibition, suggest that the N-methyl group is essential for efficient Eis inhibition and antitubercular activity.

TABLE 2

$IC_{50}$ values against purified Eis and MIC values against Mtb H37Rv and Mtb K204.

| Compound # | $IC_{50}$ (µM)[a] | H37Rv $MIC_{KAN}$ (µg/mL)[b] | K204 $MIC_{KAN}$ (µg/mL)[c] |
|---|---|---|---|
| — | — | 1.25 | 10 |
| 29 | 0.08 ± 0.02 | ≤1.25 | 2.5 |
| 30 | 6.2 ± 1.3 | ≤1.25 | 5 |
| 31 | >200 | ≤1.25 | 10 |

TABLE 2-continued $IC_{50}$ values against purified Eis and MIC values against Mtb H37Rv and Mtb K204.

| Compound # | $IC_{50}$ (µM)[a] | H37Rv $MIC_{KAN}$ (µg/mL)[b] | K204 $MIC_{KAN}$ (µg/mL)[c] |
|---|---|---|---|
| 32 | 10.6 ± 2.5 | ≤1.25 | 5 |
| 33 | 5.8 ± 1.8 | ≤1.25 | 5 |
| 34 | 0.100 ± 0.045 | ≤1.25 | 2.5 |
| 35 | 0.25 ± 0.06 | ≤1.25 | 2.5-5 |
| 36 | >200 | ≤1.25 | 10 |
| 37 | 3.0 ± 0.7 | ≤1.25 | 5 |
| 38 | 0.056 ± 0.004 | ≤1.25 | 2.5 |
| 39 | 5.8 ± 1.2 | ≤1.25 | ≤1.25 |
| 40 | 7.4 ± 3.3 | ≤1.25 | 5-10 |
| 41 | 0.37 ± 0.09 | ≤1.25 | 2.5-5 |
| 42 | 0.027 ± 0.012 | ≤1.25 | 5-10 |
| 43 | 0.23 ± 0.03 | ≤1.25 | 2.5-5 |
| 44 | 0.7 ± 0.3 | ≤1.25 | 5-10 |
| 45 | 27 ± 8 | ≤1.25 | 5-10 |
| 46 | 0.00024 ± 0.00010 | ≤1.25 | ≤1.25 |
| 47 | 0.30 ± 0.08 | ≤1.25 | 10 |

[a]$IC_{50}$ values against purified Eis enzyme,
[b]anti-TB activity of KAN against Mtb H37Rv,
[c]anti-TB activity of KAN against Mtb K204.

Having established the importance of the N-methyl moiety, the effect of substitutions on the benzene ring of the aniline moiety were explored. Removing all substituents on the benzene ring (compound 33) resulted in a 70-fold decrease in Eis inhibitory activity ($IC_{50}$=5.8±1.8 µM) when compared to that of lead 29 and did not overcome KAN resistance in Mtb K204, suggesting the importance of a substituted aniline for Eis inhibition and antitubercular activity. In general, para substitution (compounds 29 with a p-Br, 34 with a p-Cl, and 35 with a p-iPr) was found to be highly favorable and yielded compounds with $IC_{50}$ values varying from 0.08-0.25 µM, which overcame KAN resistance ($MIC_{KAN}$=2.5 µg/mL) in KAN-resistant Mtb. Interestingly, p-methoxy substitution resulted in a compound (13) that was found to be inactive during our HTS. To delineate if ortho or meta substitution would be even more favorable than para substitution, we generated compounds 36 (with an o-OMe) and 39 (with a m-OMe). The o-methoxy substituted 36 was found to be completely inactive ($IC_{50}$>200 µM and $MIC_{KAN}$=10 µg/mL against Mtb K204), whereas the m-methoxy substituted 39 was found to be a potent Eis inhibitor ($IC_{50}$=5.8±1.2 µM) and was one of our two compounds to fully overcome KAN resistance in Mtb K204 ($MIC_{KAN}$≤1.25 µg/mL). It is important to note that incorporating an additional m-methoxy group, as in compound 40, was detrimental for the overall activity of the molecule, which suggested that mono-substitution is more promising than di-substitution. We also synthesized the m-bromo derivative 38, which demonstrated a slightly improved Eis inhibitory activity ($IC_{50}$=0.056±0.004 µM) than did the corresponding para derivative 29, while also being able to overcome KAN resistance in Mtb K204 (MIC=2.5 µg/mL). We also found that the m-iso-propyl derivative 43 and its para counterpart 35 displayed similar Eis inhibitory activity ($IC_{50}$=0.23±0.03 and 0.25±0.06 µM, respectively) and resulted in identical KAN MIC values (2.5-5n/mL) against KAN-resistant Mtb. While the p-methyl derivative 14 was inactive in our HTS, its meta counterpart 41 displayed good Eis inhibition ($IC_{50}$=0.37±0.09 µM) and some ability to overcome KAN resistance in Mtb K204 (MIC 2.5-5 µg/mL). These data suggest that mono-mew substitution is either equal or more advantageous then para, which is more beneficial than ortho. Based on these results, we generated additional m-alkylated sulfonamides (42, 44, and 45) and observed that longer or bulkier alkyl groups, although good for Eis inhibition, did not produce compounds capable of overcoming KAN resistance in Mtb K204. Finally, with the hope of increasing any possible π-π interaction between the inhibitor and the AG-binding site of the Mtb Eis, we generated compound 46, which showed an incredible increase in Eis inhibitory activity ($IC_{50}$=0.00024±0.00010 μM) and was found to completely overcome KAN resistance in Mtb K204 ($MIC_{KAN}$≤1.25 μg/mL). Compound 46 is currently our most potent and promising Eis inhibitor that can be used in conjunction with KAN.

To examine the selectivity of our two best inhibitors (39 and 46) towards Eis, next these two compounds were tested against three other AAC enzymes: AAC(2')-Ic from Mtb (17, 18), AAC(3)-IV from *E. coli* (19, 20), and AAC(6')-Ie/APH(2")-Ia from *Staphylococcus aureus* (21, 22). Sulfonamides 39 and 46 did not inhibit KAN acetylation by the AACs tested at concentrations as high as 200 μM with the exception of 39, which inhibited 15% of the AAC(2')-Ic activity when tested at 200 μM. These data demonstrate the high selectivity of the inhibitors towards Eis.

Figure 2A:
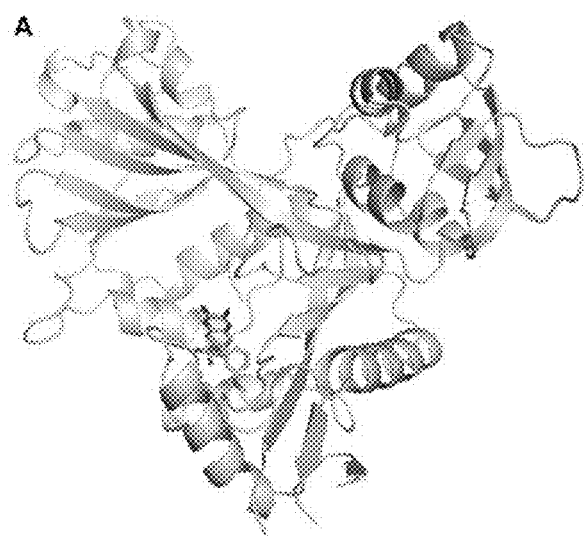
FIG. 2a. provides the overall view of a monomer of Eis-CoA-inhibitor 39 complex.
Figure 2B:
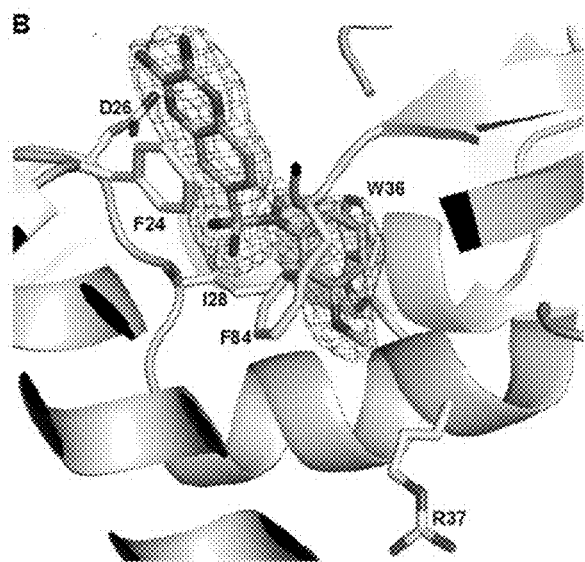
FIG. 2b. provides the zoomed-in view of the AG-binding site with the bound inhibitor. The omit $F_o$-$F_c$ map (contoured at 3a) generated without the inhibitor is shown as mesh. The bound CoA is omitted to avoid obstructing the view. The inhibitor is shown as sticks and the interacting side chains of Eis are shown as pale sticks.

Crystal Structure of EisC204A-CoA-inhibitor 39 Complex. In order to characterize the mechanism of our Eis inhibitors, explain the SAR, and aid in future drug development, the crystal structure of Eis in complex with CoA and inhibitor 39 was determined at the resolution of 2.1 Å (FIG. 2 and Table 3).

TABLE 3

X-ray diffraction data collection and refinement statistics for the EisC204A-CoA-inhibitor 39 ternary complex structure.

| Data collection | |
| --- | --- |
| Space group | R32 |
| Number of monomers per asymmetric unit | 1 |
| Unit cell dimensions | |
| a, b, c (Å) | 175.2, 175.2, 122.3 |
| α, β, γ (°) | 90, 90, 120 |
| Resolution (Å) | 50.0-2.1 (2.14-2.10)[a] |
| I/σ | 16 (2.1) |
| Completeness (%) | 95.8 (97.7) |
| Redundancy | 3.9 (3.8) |
| $R_{merge}$ | 0.08 (0.50) |
| Number of unique reflections | 37,907 |
| Structure refinement statistics | |
| Resolution (Å) | 40.0-2.1 |
| R (%) | 19.4 |
| $R_{free}$ (%) | 21.9 |
| Bond length deviation (rmsd) from ideal (Å) | 0.006 |
| Bond angle deviation (rmsd) from ideal (°) | 1.35 |
| Ramachandran plot statistics[b] | |
| % of residues in most allowed regions | 93.8 |
| % of residues in additional allowed regions | 6.2 |
| % of residues in generously allowed regions | 0.0 |
| % of residues in disallowed regions | 0.0 (0 residues) |

[a]Numbers in parentheses indicate the values in the highest-resolution shell.
[b]Indicates Procheck statistics (23).

Although sulfonamide 46 was the best compound in biochemical and biological studies, it did not co-crystallize with Eis. Therefore efforts were focused on compound 39, the second best compound. The crystal structure demonstrates that inhibitor 39 is bound in the part of the AG-binding pocket that is formed by the N-terminal domain of Eis. The inhibitor is apparently stabilized in the bound state by numerous hydrophobic interactions. Specifically, the aniline moiety is stacked between the rings of Phe84 and Trp36, with the methoxy group surrounded by the nonpolar stem of the Arg37 side chain, Phe84, Trp13, and Val40. This explains why removing the aniline ring resulted in a loss of activity for compounds 12, 15, 16, and 22-26. The quinoxaline moiety stacks against Phe24, a residue that interacts with tobramycin, as previously observed in a crystal structure of an Eis-TOB complex. The NH group of the quinoxaline ring on the side of the sulfonamide forms a hydrogen bond with the carboxyl group of Asp26 (N—O distance of 2.9 Å) and the oxygen of the sulfonamide forms a hydrogen bond with the main chain nitrogen of Ile28 (O—N distance of 3.0 Å). Our SAR studies showed that compounds with an N-methyl group of the sulfonamide moiety displayed higher Eis inhibitory activity than those with an NH group, which can be rationalized by the optimal van der Waals interaction of the methyl with Trp36 (the distance between the methyl C atom and the closest C of the Trp36 side chain is 3.6 Å). Eliminating the methyl group would abolish this interaction, putting a polar NH in a hydrophobic environment, likely destabilizing binding (5 vs 37, 30 vs 29, 31 vs 33, and 32 vs 35). Replacing the aniline ring with an N-aryl piperazine (compounds 17-21) resulted in a loss of Eis inhibitory activity when compared to the aniline ring. As described above, this part of the molecule is snugly fit in a hydrophobic pocket, which is too small to accommodate these larger groups. The ortho position of the aniline ring is flanked by the C-terminal residue Phe402 and it abuts Phe84, explaining why an ortho substitution, as in compound 36, resulted in a loss of Eis inhibitory activity. A bulky group such as n-butyl (44) or t-butyl (45) in meta position of the aniline ring would clash with Arg37 that is structurally fixed by π-π stacking with the inhibitor, explaining the poor inhibitory activity of these two compounds. A meta,meta-disubstitution (40) resulted in a dramatic decrease in activity as the second substituent would clash with the side chain of Met65. Electron-donating groups such as methoxy (39) or a naphthalene ring (46) increase the π-π interaction of the aniline ring with Phe84 and Trp36, explaining their stronger interactions in the AG-binding pocket of Eis. However, combining the two substituents in compound 47 led to a loss of activity, as both substitutions cannot be sterically accommodated.

The overall conformation of Eis in complex with the inhibitor is similar to the previously reported crystal structure. A notable conformational difference is that a part of a loop (residues 28-30) and a helix (residues 31-37) are shifted towards the inhibitor relative to their conformation in the structure without the inhibitor by 1-1.5 Å, apparently in an induced-fit fashion, to maximize steric contacts. The indole ring of Trp36 in this helix is rotated by ~40°, maximizing the stacking with the aniline ring and other interactions, as explained above. These small, but significant conformational changes likely precluded us from obtaining a correct model of a bound inhibitor by prior extensive computational docking simulations. In summary, the crystal structure of the EisC204A-CoA-inhibitor 39 complex allowed explanation of biochemical and biological data and provides a solid foundation for further rational structure-based development of Eis inhibitors.

In conclusion, the biochemical, biological, and structural studies described in this example provide a proof-of-principle of the activity of Eis inhibitors as promising KAN adjuvants. The SAR combined with the co-crystal structure will guide future development of these compounds for their clinical use against MDR- and XDR-TB.

Synthesis and Characterization of Sulfonamides 29-47.

Sulfonamides 29-47 were synthesized in two chemical steps (Table 1A). A detailed description of the synthetic procedures as well as characterization by $^1$H, $^{13}$C NMR, and mass spectrometry can be found in the Materials and Methods Section.

Chemical Library Screening for Eis Inhibitors, Hit Validation, Inhibition Kinetics, and Inhibitor Selectivity.

Acetyltransferase inhibition was assessed by monitoring the absorbance at 412 nm ($\varepsilon_{412}$=14140 M$^{-1}$ cm$^{-1}$) of a compound generated by the reaction between the free thiol group of CoA released during acetylation and 5',5-dithiobis-(2-nitrobenzoic acid) (DTNB), as described in the Materials and Methods and Table 2.

Mycobacterial MIC Determination by Alamar Blue.

The MIC values for KAN in the absence and presence of Eis inhibitors 29-47 was determined against KAN-sensitive and KAN-resistant Mtb strains H37Rv and K204, respectively, as described in detailed in the Materials and Methods Section and Table 2.

Crystallization and Structure Determination of the EisC204A-CoA-Inhibitor 39 Complex.

Inhibitor 39 was soaked into rhombohedral crystals of EisC204A in complex with CoA upon an elaborate solvent exchange procedure as described in details in the Materials and Methods. Data were collected and the structure was determined by molecular replacement using the previously published Eis structure (PDB code 3R1K) as the initial model. The inhibitor was built unambiguously into a strong $F_o$-$F_c$ electron density as detailed in the Materials and Methods, FIG. 2, and Table 3.

Example 2

Disclosed herein are inhibitors of Eis that could be co-administered with KAN in order to prevent inactivation by Eis in Mtb. Here, the identification as well as the biochemical and biological characterization of several potent inhibitors of Eis that were able to restore the antibacterial activity of KAN in a KAN-resistant strain, Mtb K204 are reported. To clarify in atomic details the mode of action of these compounds and their structure-activity-relationships, crystal structures of EisC204A in complex with CoA and two of these inhibitors were also determined. A 123,000-compound high-throughput screen (HTS) yielded several small-molecule Eis inhibitors that share a sulfonyl isothiazole scaffold. These were investigated for their structure-activity relationships. Crystal structures of Eis in complex with two potent inhibitors show that these molecules are bound in the conformationally adaptable aminoglycoside binding site of the enzyme, thereby obstructing binding of KAN for acetylation. Importantly, several Eis inhibitors, when used in combination with KAN against resistant Mtb, efficiently overcome KAN resistance. This approach paves the way toward development of novel combination therapies against aminoglycoside-resistant TB.

High-Throughput Screening Leads to the Identification of a Promising Eis Inhibitor Scaffold.

Figure 3:
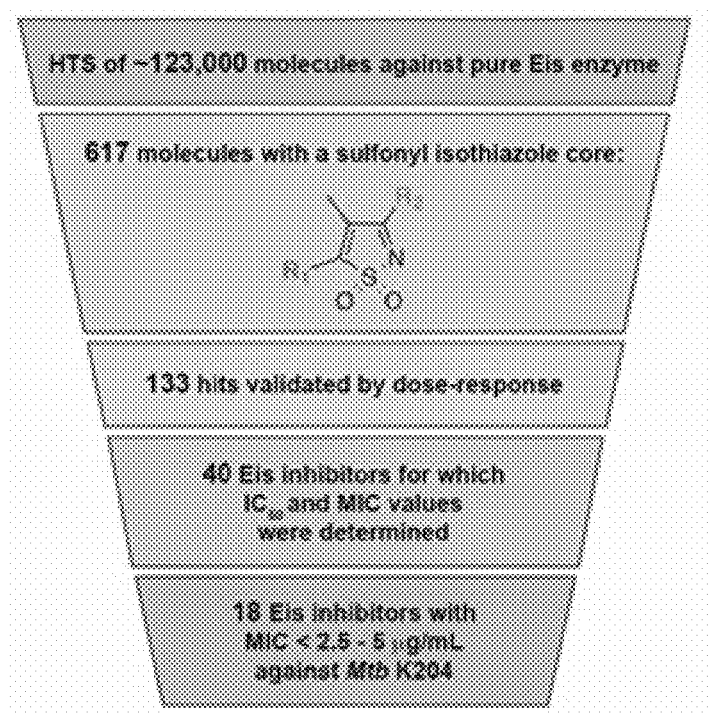
FIG. 3 is a schematic representation of the winnowing of ~123,000 small organic molecules to 18 showing inhibition of both Eis enzymatic activity and growth of Mtb K204 in the presence of KAN.

In order to identify Mtb Eis inhibitors, HTS of molecular libraries comprising 123,000 structurally diverse small molecules using a previously reported Eis acetylation assay in the miniaturized format was performed (FIG. 3). The initial HTS assay was performed using the aminoglycoside neomycin B (NEO) as a substrate, which was selected over KAN to maximize the signal to noise ratio under the HTS conditions. However, KAN was used in all post-HTS assays, since it is the clinically relevant aminoglycoside. The HTS yielded 617 hits containing a sulfonyl isothiazole core that were re-tested (Table 4 and Table 5). Of these 617 molecules, 133 showed reproducible inhibition of Eis enzymatic activity in the same single-point HTS assay. Thirty-six of these 133 compounds were chosen for further testing in dose-response assays, based on the potency of their inhibition of Eis in the HTS assay and the structural diversity of their chemical substituents ($R_1$ and $R_2$ groups). In a previous study of Eis inhibitors evaluating fewer molecules, we demonstrated that active compounds contained (i) a group that may become positively charged, usually an amine, or (ii) an aromatic group. The presence of either of these groups was therefore also a criterion for selection of compounds for dose-response testing. Additionally, four analogues that were not a part of the original library were included, but which contained the same structural core (Table 4). This process yielded a group of forty molecules, for which $IC_{50}$ values were determined against purified Eis. The effect of these compounds on KAN MIC for KAN-susceptible (H37Rv) and KAN-resistant (K204) Mtb strains (Table 5), were also measured as described in the two following sections.

TABLE 4

Structures of Compounds of Example 2.
The 617 molecules tested are noted in Table 6.

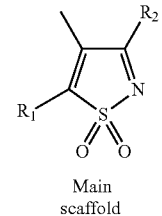

Main scaffold $R_1$ =

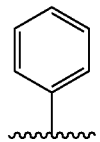

a

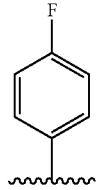

b

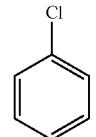

c

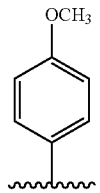

d

TABLE 4-continued
Structures of Compounds of Example 2.
The 617 molecules tested are noted in Table 6.
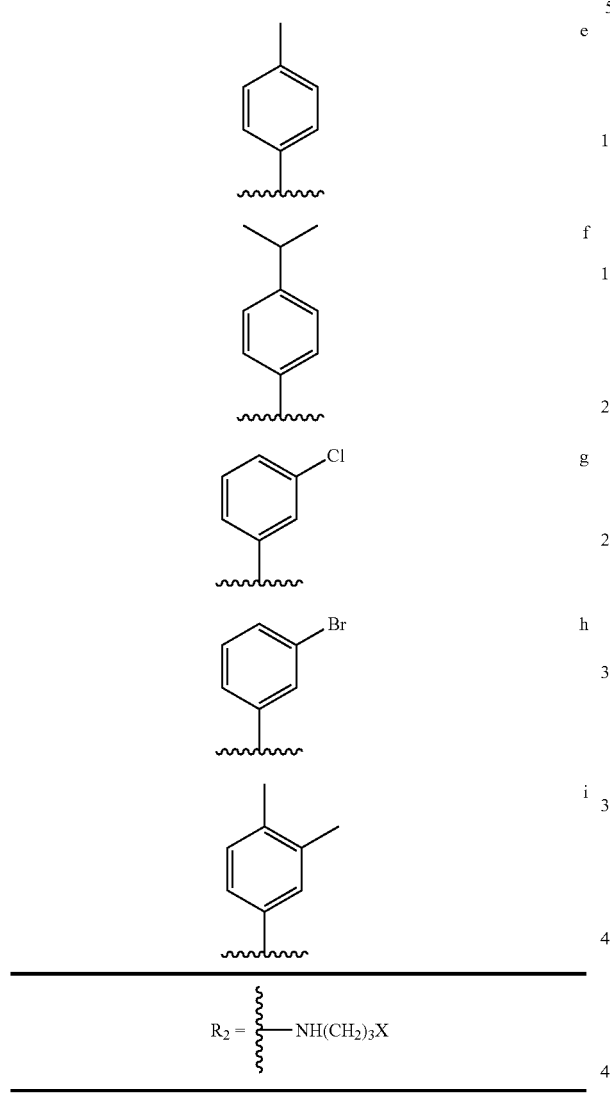
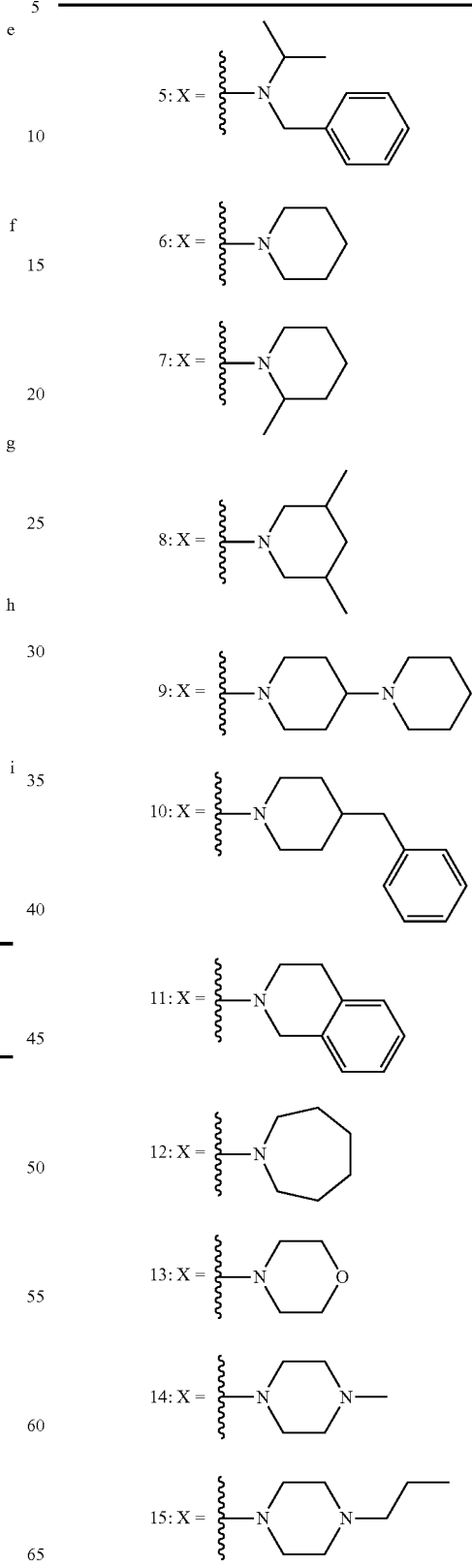

TABLE 4-continued
Structures of Compounds of Example 2.
The 617 molecules tested are noted in Table 6.
16: X = 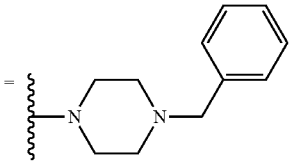
17: X = 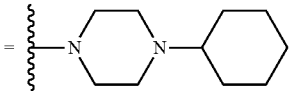
18: X = 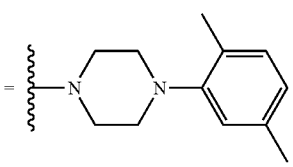
R₂ = 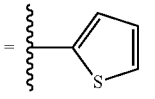—NH(CH₂)₂X
19: X = 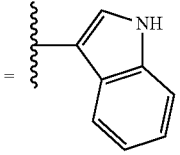
20: X = 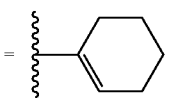
21: X = 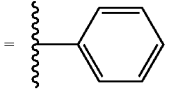
22: X = 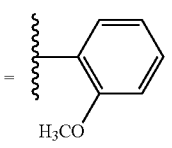
23: X = 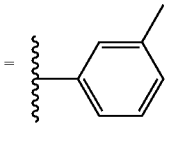
24: X = 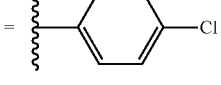
25: X = 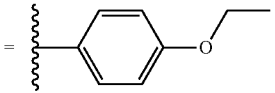
26: X = 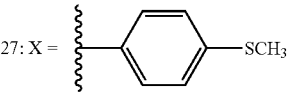
TABLE 4-continued
Structures of Compounds of Example 2.
The 617 molecules tested are noted in Table 6.
27: X = 
28: X = 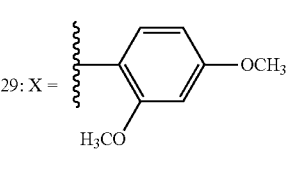
29: X = 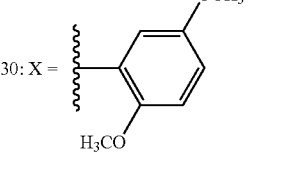
30: X = 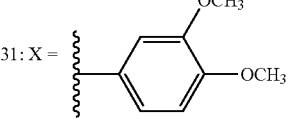
31: X = 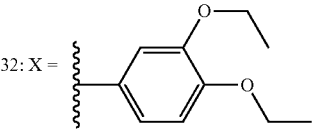
32: X = 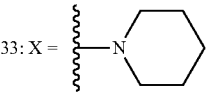
33: X = 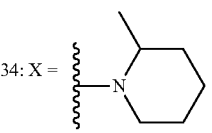 [SMILES: *N1CCCCC1C]
34: X = 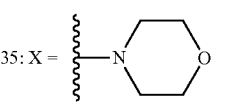
35: X = 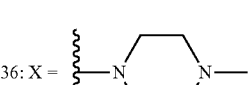
36: X = 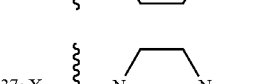
37: X = 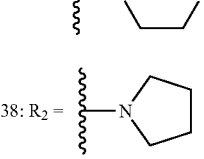
38: R₂ =

TABLE 4-continued
Structures of Compounds of Example 2.
The 617 molecules tested are noted in Table 6.
39: R₂ = 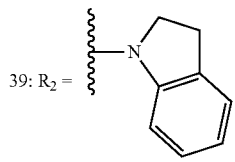 [SMILES: *N1CCc2ccccc21]
40: R₂ = 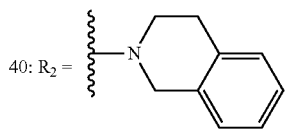
R₂ = 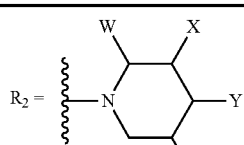
Note: When not specified, W, X, Y, and Z = H
41: W = X = Y = Z = H
42: W = CH₃
43: X = CH₃
44: Y = CH₃
45: X = Z = CH₃
46: Y = 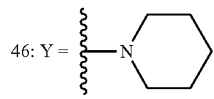
47: X = 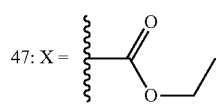
48: Y = 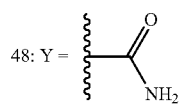
49: Y = 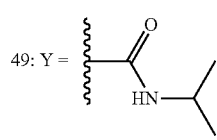 [SMILES: *C(=O)NC(C)C]
50: Y = 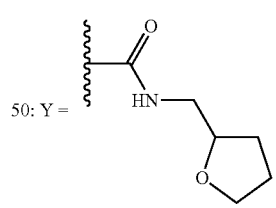 [SMILES: *C(=O)NCC1CCCO1]
51: Y = 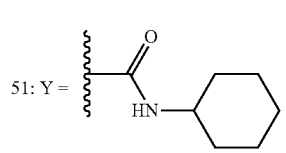 [SMILES: *C(=O)NC1CCCCC1]
TABLE 4-continued
Structures of Compounds of Example 2.
The 617 molecules tested are noted in Table 6.
52: Y = 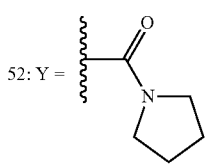 [SMILES: *C(=O)N1CCCC1]
53: Y = 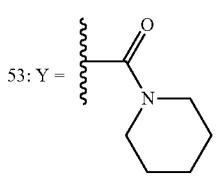 [SMILES: *C(=O)N1CCCCC1]
54: Y = 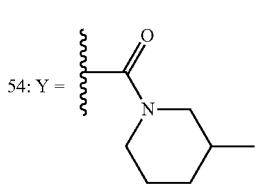 [SMILES: *C(=O)N1CCCC(C)C1]
55: Y = 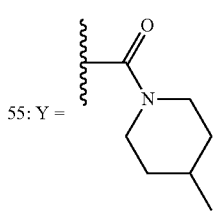 [SMILES: *C(=O)N1CCC(C)CC1]
56: Y = 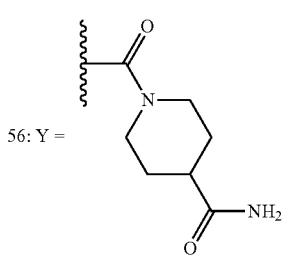 [SMILES: *C(=O)N1CCC(C(N)=O)CC1]
57: Y = 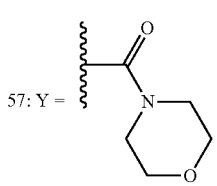 [SMILES: *C(=O)N1CCOCC1]
58: Y = 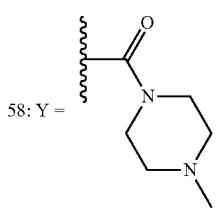 [SMILES: *C(=O)N1CCN(C)CC1]

TABLE 4-continued
Structures of Compounds of Example 2.
The 617 molecules tested are noted in Table 6.
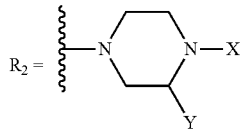
Note: In all cases Y = H, except for 76 (Y = CH₃)
60: X = 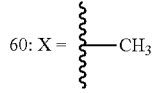 —CH₃
61: X = 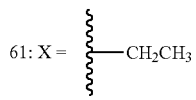 —CH₂CH₃
62: X = 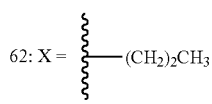 —(CH₂)₂CH₃
63: X = 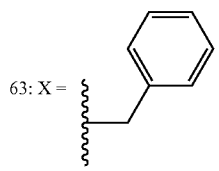 [SMILES: *Cc1ccccc1]
64: X = 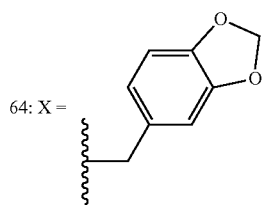
65: X = 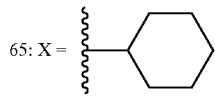
66: X = 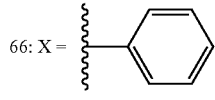
67: X = 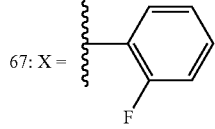
68: X = 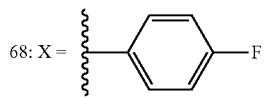
69: X = 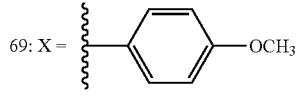
TABLE 4-continued
Structures of Compounds of Example 2.
The 617 molecules tested are noted in Table 6.
70: X = 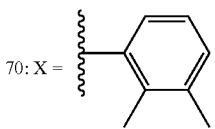 [SMILES: *c1cccc(C)c1C]
71: X = 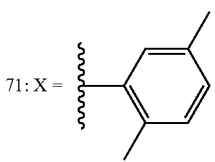 [SMILES: *c1cc(C)ccc1C]
72: X = 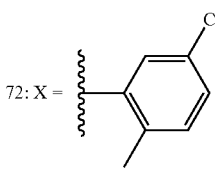
73: X = 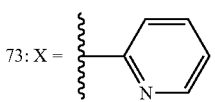 [SMILES: *c1ccccn1]
74: X = 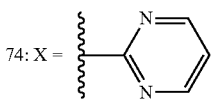
75: X = 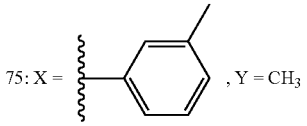, Y = CH₃
76: X = 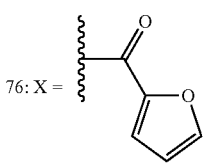 [SMILES: *C(=O)c1ccco1]
77: X = 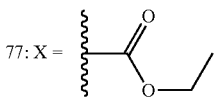
78: X = 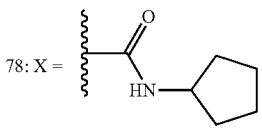 [SMILES: *C(=O)NC1CCCC1]
R₂ = 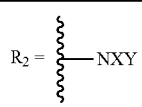—NXY
79: X = 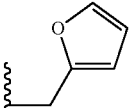, Y = CH₃

TABLE 4-continued

Structures of Compounds of Example 2.
The 617 molecules tested are noted in Table 6.

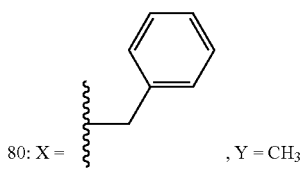 [SMILES: *Cc1ccccc1]

80: X = [benzyl], Y = CH$_3$

81: X = Y = CH$_2$CH$_3$

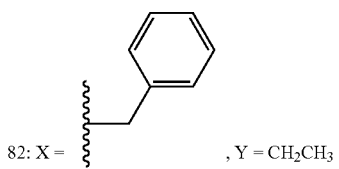 [SMILES: *Cc1ccccc1]

82: X = [benzyl], Y = CH$_2$CH$_3$

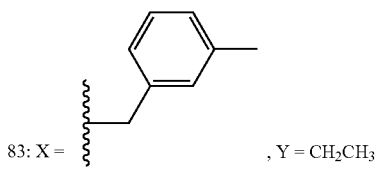 [SMILES: *Cc1cccc(C)c1]

83: X = [m-methylbenzyl], Y = CH$_2$CH$_3$

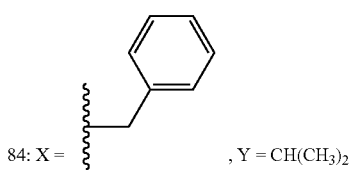 [SMILES: *Cc1ccccc1]

84: X = [benzyl], Y = CH(CH$_3$)$_2$

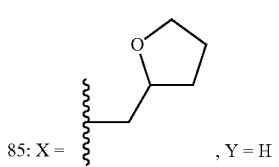 [SMILES: *CC1CCCO1]

85: X = [tetrahydrofuran-2-ylmethyl], Y = H

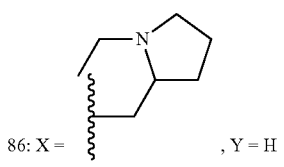 [SMILES: *CC1CCCN1CC]

86: X = [indolizidinyl], Y = H

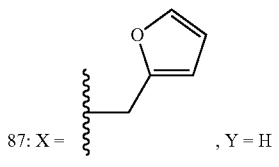 [SMILES: *Cc1ccco1]

87: X = [furan-2-ylmethyl], Y = H

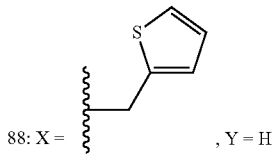 [SMILES: *Cc1cccs1]

88: X = [thiophen-2-ylmethyl], Y = H

TABLE 4-continued

Structures of Compounds of Example 2.
The 617 molecules tested are noted in Table 6.

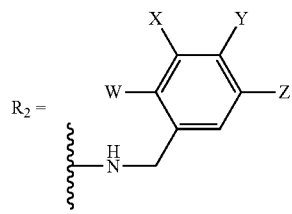

Note: When not specified, W, X, Y, and Z = H

89: W = X = Y = Z = H
90: W = CH$_3$
91: W = F
92: W = Cl
93: W = OCH$_3$
94: W = OCH$_2$CH$_3$
95: X = Cl
96: X = Br
97: X = OCH$_3$
98: Y = CH$_3$
99: Y = CH$_2$CH$_3$
100: Y = F
101: Y = Cl
102: Y = OCH$_3$
103: Y = OCH$_2$CH$_3$
104: Y = OCH(CH$_3$)$_2$
105: Y = N(CH$_3$)$_2$
106: W = X = OCH$_3$
107: W = OCH$_3$, X = OCH$_2$CH$_3$
108: W = CH$_3$, Y = N(CH$_2$CH$_3$)$_2$
109: W = OCH$_3$, Y = Br
110: W = Z = OCH$_3$
111: X, Y = OCH$_2$O

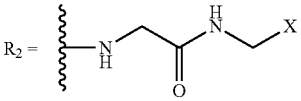

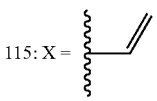 [SMILES: *C=C]

115: X =

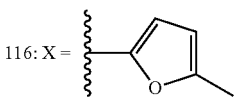 [SMILES: *c1ccc(C)o1]

116: X =

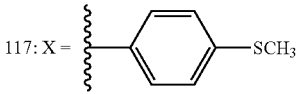

117: X =

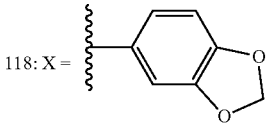

118: X =

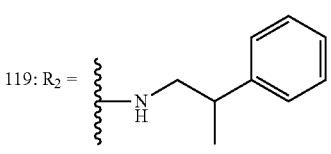 [SMILES: *NCC(C)c1ccccc1]

119: R$_2$ =

TABLE 4-continued

Structures of Compounds of Example 2.
The 617 molecules tested are noted in Table 6.

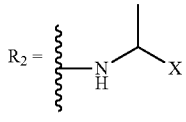

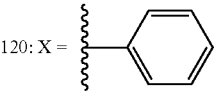
120: X =

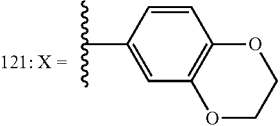 [SMILES: *c1ccc2c(c1)OCCO2]
121: X =

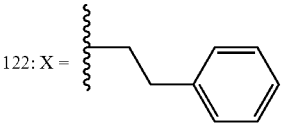
122: X =

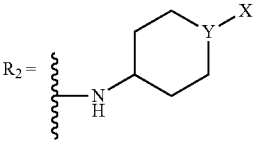

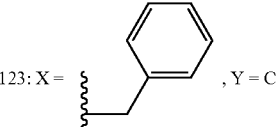
123: X =           , Y = C

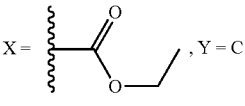
124: X =           , Y = C

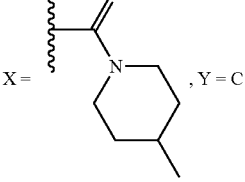
125: X =           , Y = C

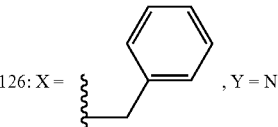
126: X =           , Y = N

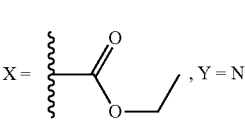
127: X =           , Y = N

TABLE 4-continued

Structures of Compounds of Example 2.
The 617 molecules tested are noted in Table 6.

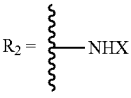
$R_2 =$ —NHX

137: X = $CH_3$
138: X = $CH_2CH_3$
139: X = $(CH_2)_2CH_3$
140: X = $CH(CH_3)_2$
141: X = $CH(CH_3)CH_2CH_3$
142: X = $C(CH_3)_3$
143: X = $(CH_2)_2CH(CH_3)_2$
144: X = $(CH_2)_2OCH_3$
145: X = $(CH_2)_3OCH_3$
146: X = $(CH_2)_3OCH_2CH_3$
147: X = $(CH_2)_3OCH(CH_3)_2$

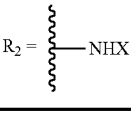
$R_2 =$ —NHX

128: X =

129: X =

130: X =

131: X =

132: X =

133: X =

134: X =

135: X =

TABLE 4-continued

Structures of Compounds of Example 2.
The 617 molecules tested are noted in Table 6.

136: X = 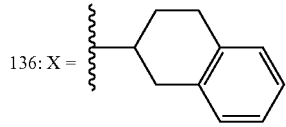 [SMILES: *C1CCc2ccccc2C1]

$R_2$ = 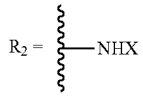—NHX

205: X = 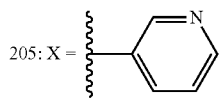

206: X = 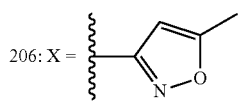 [SMILES: *c1cc(C)on1]

$R_2$ = 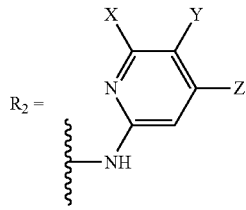

Note: When not specified, X, Y, and Z = H

199: X = Y = Z = H
200: X = $CH_3$
201: Y = $CH_3$
202: Y = Cl
203: Y = Br
204: Z = $CH_3$ $R_2$ = 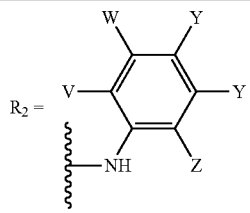

Note: When not specified, V, W, X, Y, and Z = H

148: V = $CH_3$
149: V = $CH_2CH_3$
150: V = F
151: V = Cl
152: V = Br
153: V = $OCH_3$
154: W = $CH_2CH_3$
155: W = F
156: W = Cl
157: W = $SCH_3$
158: X = $CH_3$
159: X = $CH_2CH_3$
160: X = $CH(CH_3)_2$

161: X = 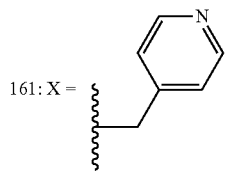 [SMILES: *Cc1ccncc1]

TABLE 4-continued

Structures of Compounds of Example 2.
The 617 molecules tested are noted in Table 6.

162: X = 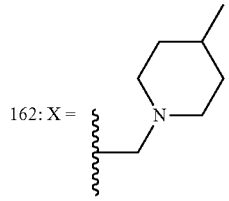

161: X = 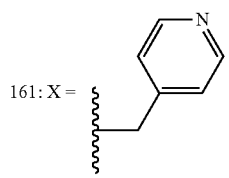 [SMILES: *Cc1ccncc1]

162: X = 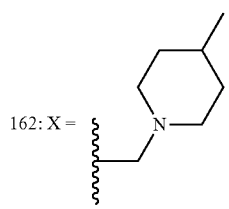

163: X = 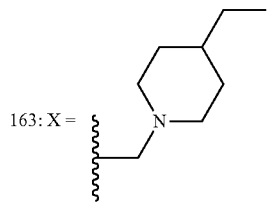 [SMILES: *CN1CCC(CC)CC1]

164: X = 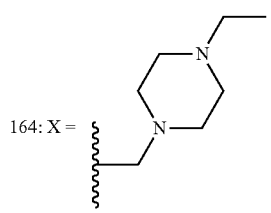 [SMILES: *CN1CCN(CC)CC1]

165: X = F
166: X = Cl
167: X = $OCH_3$
168: X = $OCH_2CH_3$
169: V = W = $CH_3$
170: V = $CH_3$, W = Cl
171: V = W = $OCH_3$
172: V = X = $CH_3$
173: V = $CH_3$, X = F
174: V = $CH_3$, X = Cl
175: V = X = F
176: V = F, X = Br
177: V = Cl, X = $CH_3$
178: V = X = $OCH_3$
179: V = Y = $CH_3$
180: V = $CH_3$, Y = Cl
181: V = Y = F
182: V = $OCH_3$, Y = $CH_3$
183: V = $OCH_3$, Y = Cl
184: V = Y = $OCH_3$
185: V = Y = $OCH_2CH_3$
186: V = Z = $CH_3$
187: V = $CH_3$, Z = $CH_2CH_3$
188: W = X = $CH_3$
189: W = $CH_3$, X = Br
190: W = Cl, X = $CH_3$

TABLE 4-continued

Structures of Compounds of Example 2.
The 617 molecules tested are noted in Table 6.

191: W = Cl, X = OCH₃
192: W = X = OCH₃
193: W, X = OCH₂O
194: W = Y = CH₃
195: W = Y = CO₂CH₃
196: W = Y = OCH₃
197: V = X = Z = CH₃
198: V = OCH₃, X = Cl, Y = CH₃

TABLE 5

Structures of the 41 Eis inhibitors with sulofnyl scaffold
for which IC$_{50}$ against pure Eis enzyme and MIC values
against strains H36Rv and K204 Mtb have been evaluated

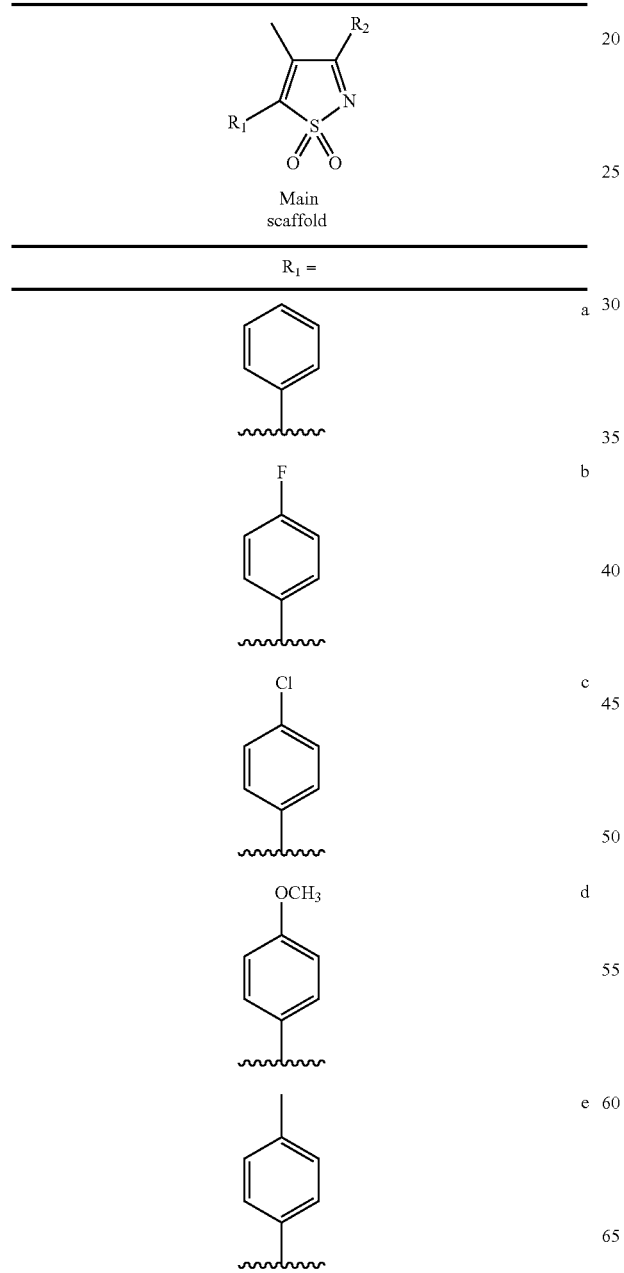

TABLE 5-continued

Structures of the 41 Eis inhibitors with sulofnyl scaffold
for which IC$_{50}$ against pure Eis enzyme and MIC values
against strains H36Rv and K204 Mtb have been evaluated

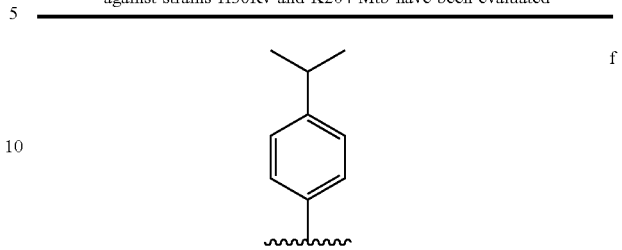   f

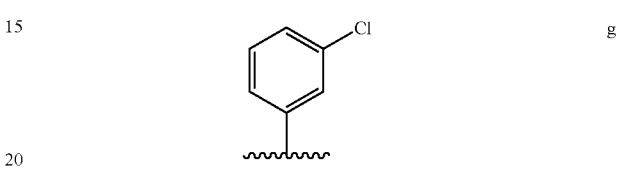   g

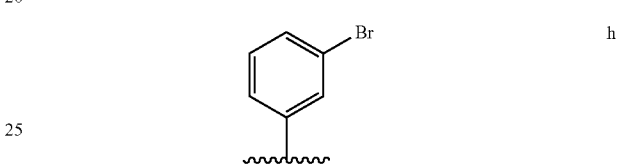   h

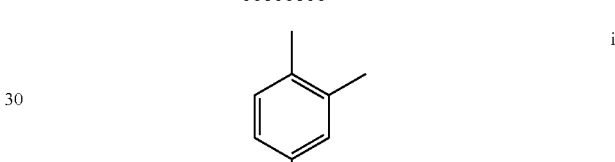   i

R₂ = —NH(CH₂)₃X

3: X = —NH(CH₂CH₃)₂

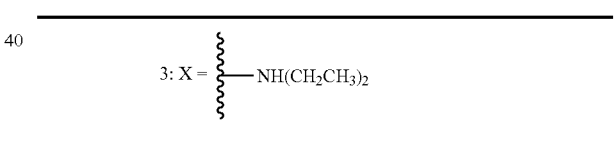   6: X =

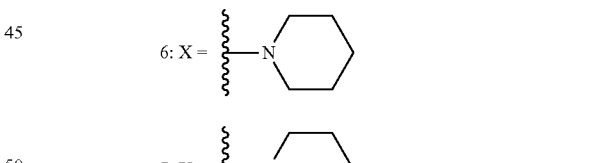   7: X =

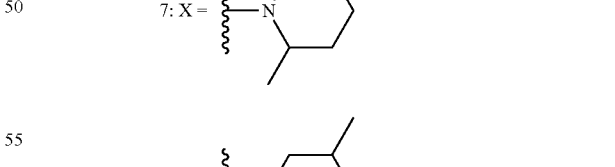   8: X =

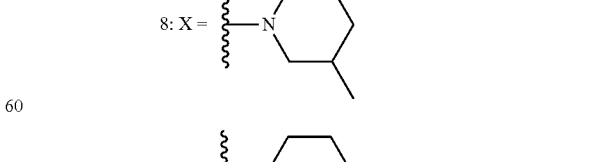   11: X =

TABLE 5-continued

Structures of the 41 Eis inhibitors with sulofnyl scaffold for which $IC_{50}$ against pure Eis enzyme and MIC values against strains H36Rv and K204 Mtb have been evaluated

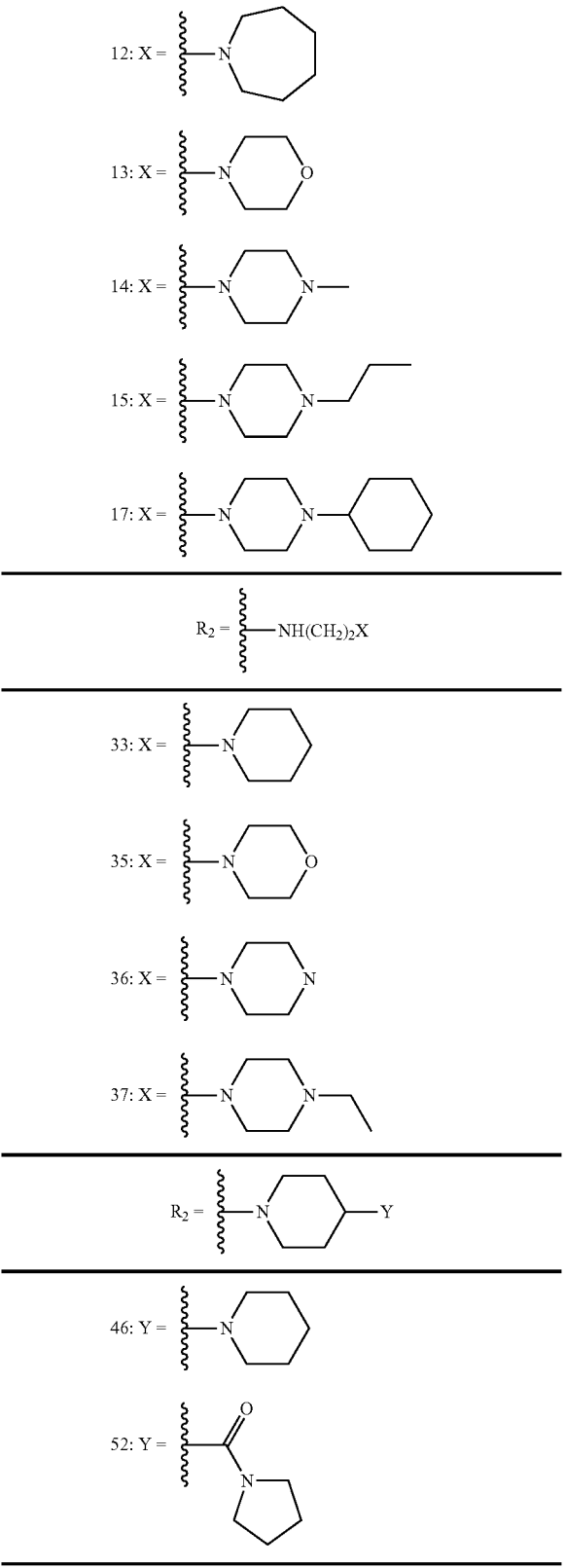

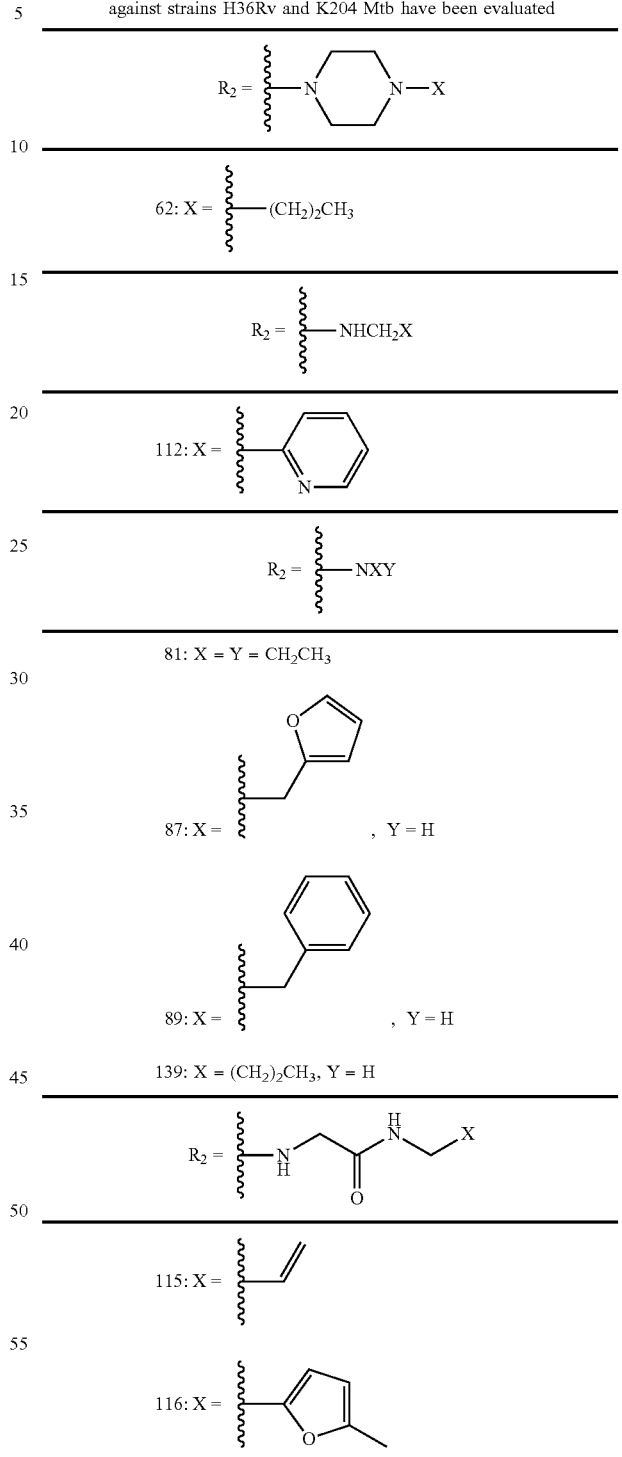

Inhibitors with $IC_{50}$ & MIC: 3i, 6b, 7b, 8a, 8e, 11c, 12e, 13a, 13e, 13g, 13i, 14c, 15e, 15f, 17i, 33a, 35e, 35g, 35h, 35i, 36d, 37b, 37d, 46a, 46b, 46c, 46h, 52i, 62i, 81b, 81g, 87b, 89b, 112b, 112i, 115i, 116i, 139b, 139e, 139i Structure-Activity Relationship (SAR) Studies.

Various $R_1$ and $R_2$ side-chains in the identified sulfonyl isothiazole scaffold (Tables 4-6), were explored to improve anti-Eis potency in vitro.

Based on the 617 initial HTS hit molecules, we first drew several unambiguous conclusions about the desirable structure of the $R_2$ side-chain. Most of the compounds for which $R_2$ contained an aromatic ring, a branched alkyl group, a cyclohexyl moiety, or a benzyl functionality did not efficiently inhibit Mtb Eis. Table 6 is a summary of Eis activity of compounds tested against enzyme and, in some instances, Mtb.

TABLE 6

Eis activity of compounds tested against purified enzyme and/or Mtb.

| Cpd | a | b | c | D | e | f | g | h | i | Cpd | A | B | c | d | e | f | g | h | i |
|---|---|---|---|---|---|---|---|---|---|---|---|---|---|---|---|---|---|---|---|
| 1 | x | x | x |  |  | x |  |  |  | 104 | x |  | x | x | x |  |  |  |  |
| 2 |  |  | x |  |  |  |  | x | x | 105 | x |  |  |  |  |  |  |  |  |
| 3 |  |  |  | □-- |  |  |  |  | □□□□ | 106 |  | X |  |  |  |  |  |  |  |
| 4 |  | □-- |  |  |  |  |  |  |  | 107 |  |  |  |  | x |  |  |  |  |
| 5 |  |  |  | X | □-- |  |  |  |  | 108 | x |  |  |  |  |  |  |  |  |
| 6 |  | □□□ |  |  |  |  |  |  |  | 109 | x |  |  |  |  |  |  |  |  |
| 7 |  | □□□ |  |  |  |  |  |  | □-- | 110 |  |  |  |  | x |  |  |  |  |
| 8 | □□x |  | □-- |  | □□□ |  |  |  |  | 111 |  | X |  | x |  | x | x | x |  |
| 9 | x | □-- |  |  |  |  |  |  |  | 112 | x | □xx |  |  |  | x | x | □□x |  |
| 10 | □□□ |  |  |  |  |  |  |  |  | 113 |  |  |  | x |  |  |  | □-- |  |
| 11 |  |  | □□□□ |  | □-- |  |  | □-- |  | 114 |  |  |  |  | x |  |  |  |  |
| 12 |  |  |  |  | □□□□ |  |  |  |  | 115 |  |  |  |  |  | □xx |  |  |  |
| 13 | □□□ |  |  |  | □□□ | □□□ |  | □□x |  | 116 |  |  |  |  |  | □xx |  |  |  |
| 14 | x |  | □□x |  |  |  |  |  |  | 117 |  |  |  |  |  | x |  |  |  |
| 15 |  |  | □-- |  | □□x | □□x |  |  |  | 118 |  |  |  | x |  |  |  |  |  |
| 16 | x |  |  |  | □-- |  |  |  |  | 119 | x | x | x | x |  |  |  | x |  |
| 17 | x | x |  |  | □-- |  |  |  | □□x | 120 |  | x | x | x |  | x |  | x |  |
| 18 | x |  |  |  |  |  |  |  | x | 121 | x | x |  | x |  | x |  | x |  |
| 19 | x |  |  | X |  |  |  |  | x | 122 | x |  |  | x | x |  |  |  |  |
| 20 |  |  |  |  |  | x |  |  |  | 123 | x |  |  |  |  |  |  |  |  |
| 21 | x |  | x | X | x |  |  | x |  | 124 |  |  |  |  |  |  |  | x |  |
| 22 |  | x | x |  |  | x |  | x | x | 125 |  |  |  |  |  |  |  | x |  |
| 23 |  |  |  |  |  | x |  |  |  | 126 |  | x | x |  |  | x | x | x | x |
| 24 |  |  | x |  |  |  |  |  |  | 127 |  |  |  |  | x |  |  |  |  |
| 25 | x |  |  |  |  |  |  |  |  | 128 | x | □-- |  | x |  |  | x |  |  |
| 26 |  |  |  | X | x |  |  |  |  | 129 |  | □-- |  | x | □-- | x | x |  |  |
| 27 | x |  |  |  | x |  |  |  |  | 130 |  |  |  |  |  | x | x | x |  |
| 28 |  |  | □-- |  |  | x |  |  | x | 131 | x | x |  |  |  |  | x | x |  |
| 29 | x |  |  |  |  |  |  |  |  | 132 |  | x |  |  |  |  | x |  |  |
| 30 |  |  |  |  |  | x |  |  |  | 133 | x |  |  |  | x |  | x |  |  |
| 31 |  | x |  | X |  | x |  | x | x | 134 |  |  |  | x |  |  |  |  |  |
| 32 |  |  |  |  |  | x |  |  |  | 135 | x |  |  |  | x |  |  |  |  |
| 33 | □□x |  |  |  |  |  |  |  |  | 136 |  |  |  | x |  |  |  |  |  |
| 34 | □-- | □-- |  |  |  |  |  |  |  | 137 |  |  |  |  | x |  |  |  |  |
| 35 | x | □-- |  | X | □xx |  | □□□ | □□□ | □□□ | 138 |  |  |  |  |  |  |  |  | □-- |
| 36 |  |  |  | □□□□ |  |  |  |  |  | 139 | x | □xx |  |  | □xx | x |  | □xx |  |
| 37 |  | □□□ |  | □xx |  |  |  |  |  | 140 |  | □-- |  |  | □-- | x |  |  |  |
| 38 |  | □-- | □-- |  | □-- |  |  | □-- |  | 141 |  | x |  |  |  | x |  | x |  |
| 39 |  | x | x | X | x | x |  |  |  | 142 |  | x |  |  |  |  |  |  |  |
| 40 | □-- | □-- |  | □-- | x |  |  | x | x | 143 | x | □-- |  | x | x | x x |  | x |  |
| 41 | □-- | □-- | □-- | □-- | □-- |  |  |  | □-- | 144 | x | x | □-- x | □□□ | x |  |  | □-- |  |
| 42 |  |  |  |  | □-- |  |  | □-- |  | 145 |  | x | x x |  |  |  |  | x |  |
| 43 | x |  |  |  | □-- |  |  |  |  | 146 | x | x | x x |  |  |  |  | x |  |
| 44 | x | □-- |  | □-- | □-- | □-- | □-- |  |  | 147 | x | x | x x |  |  |  |  | x |  |
| 45 | x | □-- | □-- | □-- |  |  |  |  | x | 148 | x | x | x |  |  |  | x | x |  |
| 46 | □□x | □□x | □□□ | □-- | □-- |  |  | □□x | □-- | 149 | x | x | x |  | x |  | x x |  |  |
| 47 |  | x |  |  |  | □-- |  |  | □-- | 150 |  |  | x |  | x | x | x | x |  |
| 48 |  |  |  |  |  | □□□ |  |  |  | 151 | x | x |  |  |  |  |  | x |  |
| 49 |  |  |  |  |  | □-- |  |  |  | 152 | x |  |  |  | x |  |  | x |  |
| 50 |  |  |  |  |  | □-- |  |  |  | 153 |  |  |  |  |  | x |  |  |  |
| 51 |  |  |  |  |  | x |  |  |  | 154 |  | x |  |  |  | x x |  |  |  |
| 52 |  |  |  |  |  | x |  |  | □□□ | 155 |  |  |  | x |  | x | x |  |  |
| 53 |  |  |  |  |  | □-- |  |  |  | 156 |  | x |  |  |  | x |  |  |  |
| 54 |  |  |  |  |  |  |  |  | □-- | 157 | x |  |  |  |  | x x |  |  |  |
| 55 |  |  |  |  |  | x |  |  |  | 158 |  |  |  |  | x |  |  |  | x |
| 56 |  |  |  |  |  |  |  |  | □-- | 159 | x | x | x |  |  |  |  | x | x |
| 57 |  |  |  |  |  | x |  |  |  | 160 | x |  |  |  |  |  |  |  |  |
| 58 |  |  |  |  |  |  |  |  | □-- | 161 |  | x |  |  | x |  |  |  | x |
| 59 | x | □-- | □-- | □-- | □-- | x |  | x | □-- | 162 |  |  |  |  | □-- |  |  |  |  |
| 60 | x | □-- | □-- | □-- |  | x | □-- | x | □-- | 163 |  |  |  |  |  | x |  |  |  |
| 61 | x | □-- | □-- | □-- |  | □-- | x | □-- | □-- | 164 |  | x |  |  | x |  |  | x |  |
| 62 |  |  |  | X |  |  |  |  | □□x | 165 |  |  |  | x |  | x | x x |  |  |
| 63 | x | x |  |  | □-- |  |  |  | □-- | 166 |  | x |  |  |  | x |  |  |  |

TABLE 6-continued

Eis activity of compounds tested against purified enzyme and/or Mtb.
Table 6

| Cpd | a | b | c | D | e | f | g | h | i | Cpd | A | B | c | d | e | f | g | h | i |
|---|---|---|---|---|---|---|---|---|---|---|---|---|---|---|---|---|---|---|---|
| 64 | x | x |   | X |   | x | x |   | □-- | 167 |   |   | x |   | x |   |   |   |   |
| 65 | x | x |   | □-- | □-- | x |   | x | x | 168 |   | x | x | x | x | x | x | x | x |
| 66 | x | x | x |   | x | x | x | x | x | 169 |   |   | x |   | x |   | x | x |   |
| 67 | x | x |   |   | x | x |   |   |   | 170 |   |   |   | x |   |   |   |   |   |
| 68 | x | x | x |   |   | x | x | x | x | 171 |   |   |   |   |   |   |   |   | x |
| 69 |   |   |   | X | x |   |   |   | x | 172 | x | x | x | x | x |   | x | x | x |
| 70 | x |   |   |   |   |   |   |   |   | 173 | x |   | x |   | x | x | x |   |   |
| 71 |   |   |   | X |   |   |   |   |   | 174 | x |   |   |   |   |   |   |   |   |
| 72 |   |   |   | X |   |   |   |   |   | 175 | x |   |   |   | x | x |   |   | x |
| 73 | x | x |   | X | □-- | x | x | x |   | 176 | x |   |   |   |   |   |   |   | x |
| 74 |   |   |   |   |   |   |   |   | x | 177 | x |   |   |   | x |   |   |   |   |
| 75 | x |   |   |   | x |   |   |   |   | 178 | x | x | x | x | x | x | x | x | x |
| 76 |   |   |   |   | □-- | □-- |   |   |   | 179 | x |   |   | x |   | x | x | x |   |
| 77 |   | x |   |   | □-- |   |   |   | □-- | 180 | x |   |   | x | x |   |   |   |   |
| 78 |   |   |   |   |   | x |   |   |   | 181 | x | x |   | x | x | x | x | x | x |
| 79 |   | □-- |   |   |   |   |   |   |   | 182 |   |   |   |   |   | x | x |   |   |
| 80 | x | □-- | □-- | X | □-- | x | x | x | x | 183 |   |   |   |   |   |   |   |   | x |
| 81 |   | □□□ |   |   |   |   | □□□ |   |   | 184 | x | x | x | x | x | x |   |   |   |
| 82 |   | □-- |   | X |   |   |   |   | x | 185 | x |   |   | x | x |   |   |   | x |
| 83 | x |   |   |   |   |   |   |   |   | 186 |   |   |   | x |   |   | x |   | x |
| 84 | x |   |   |   | x |   |   |   |   | 187 | x |   |   | x |   |   |   |   |   |
| 85 |   | x |   |   |   |   |   |   |   | 188 | x | x | x |   | x |   | x | x | x |
| 86 |   | □-- |   |   |   |   |   |   |   | 189 | x |   |   | x | x |   |   |   |   |
| 87 | x | □xx |   |   |   |   |   |   |   | 190 | x |   |   | x |   |   |   |   |   |
| 88 | x | x |   |   |   |   |   |   |   | 191 |   |   |   |   | x | x |   |   | x |
| 89 | x | □xx |   |   |   | x |   | x | x | 192 |   | x |   |   |   | x | x |   |   |
| 90 | x | x |   |   |   |   | x |   | x | 193 |   | x |   | x | x |   |   |   | x |
| 91 | x | x |   |   | x | x | x |   | x | 194 | x | x | x |   | x |   | x | x | x |
| 92 | x | x | x |   | x |   |   |   | x | 195 |   |   |   |   | x |   |   |   |   |
| 93 |   |   |   |   |   | x |   |   | x | 196 |   |   | x |   | x | x | x | x |   |
| 94 | x |   |   |   | x | x |   |   | x | 197 | x |   |   | x |   |   |   |   |   |
| 95 |   |   |   |   |   | x |   |   |   | 198 | x |   |   | x |   |   |   |   |   |
| 96 |   |   |   |   |   | x |   |   |   | 199 |   | x |   |   |   |   |   |   |   |
| 97 |   |   |   |   |   |   | x |   |   | 200 | x |   |   |   |   |   |   |   |   |
| 98 | x | x | x | x |   |   |   |   |   | 201 |   |   | x |   | x |   |   |   |   |
| 99 |   |   | x | x |   |   |   |   |   | 202 |   | x |   |   |   |   |   |   |   |
| 100 | x | x | x |   |   | x |   | x | x | 203 |   |   |   |   |   |   |   |   | x |
| 101 | x |   |   |   | x |   |   |   | x | 204 |   | x |   |   |   |   |   |   |   |
| 102 |   | □-- |   | x |   |   | x |   | x | 205 | x |   |   | x |   | x | x |   |   |
| 103 | x | x | x | x | x |   |   |   | x | 206 | x |   |   |   |   |   |   |   | x |

Symbol legend:
Empty box indicates that the combination of $R_1$ (letter) and $R_2$ (number) did not exist in the tested library.
x indicates that the compound did not inhibit Eis purified enzyme in the initial HTS.

□-- indicates that the compound inhibited Eis purified enzyme in the initial HTS, but was not pursued for determination of $IC_{50}$ values.

□xx indicates that the compound inhibited Eis purified enzyme in the initial HTS, but was found to not be a strong Eis inhibitor after determination of its $IC_{50}$ and also did not affect Mtb growth.

□□x indicates that the compound inhibited Eis purified enzyme in the initial HTS and was found to be a moderate to good Eis inhibitor after determination of its $IC_{50}$, but did not affect Mtb growth.

□□□ indicates that the compound inhibited Eis purified enzyme in the initial HTS and was found to be a moderate to good Eis inhibitor after determination of its $IC_{50}$, and was also found to affect Mtb growth.

□□□□ indicates compounds that we selected to purchase that were not in our initial HTS. These compounds were found to be a moderate to good Eis inhibitor after determination of its $IC_{50}$ and were also found to affect Mtb growth.

Compounds that did not efficiently inhibit Mtb Eis are indicated by x in Table 6. Among the forty compounds that were pursued beyond the dose-response assay, compounds containing $R_2$ groups 8, 13, 15, 35, 46, and 81 inhibited Eis in vitro when combined with multiple $R_1$ substituents (as indicated by □□x and □□□, respectively, in Table 6) while other $R_2$ groups were shown to inhibit Eis in dose-response assays when in combination with only one of the possible $R_1$ substituents (6b, 7b, 11c, 12e, 14c, 17i, 33a, 36d, 37b, 52i, 62i, and 112i). Overall, two large families of $R_2$ substituents emerged as potential potent inhibitors of Eis: (i) compounds with $R_2$ containing two nitrogen atoms separated by three carbon atoms (structures 3, 6-8, 11-15, and 17), particularly compounds with large bulky groups or a cyclohexyl ring attached to the extended nitrogen atom were most often inhibitory; and (ii) compounds containing an $R_2$ group with two nitrogen atoms separated by two carbon atoms also efficiently inhibited Eis (structures 33, 35-37, and 112). In this series of molecules, only compounds with a nitrogen atom located in a cyclohexyl ring were inhibitory.

We next explored the effect of the $R_1$ substituents on Eis inhibition. Upon initial inspection of the 617 HTS hits, the identity of the $R_1$ substituent appeared to have little effect on their Eis inhibitory activity. However, when analyzing these side chains statistically, patterns emerged. The p-fluorophenyl group (b) had the highest percentage (34%) of compounds inhibiting Eis in the initial HTS; this was followed closely by the p-methylphenyl group (e, 33%) and the m,p-dimethylphenyl group (i, 30%), suggesting that these three groups as $R_1$ substitutions have a better chance of contributing positively to Eis inhibition. The next best $R_1$ substituent was the p-chlorophenyl group (c) with 27% of the compounds within this group displaying inhibition of Eis. The m-chlorophoenyl group (g) and p-anisole group (d) were next with 19% and 18% of their compounds displaying Eis inhibition, respectively. Finally, with 13%, 12%, and 9% of compounds showing Eis inhibition were compounds containing the p-isopropylphenyl (f), the m-bromophenyl (h), and the phenyl (a) group as $R_1$, respectively.

Having established general trends for the $R_1$ and $R_2$ substituents by analyzing the data from Table 6, we next focused on the measured in vitro potency ($IC_{50}$) of the forty selected compounds (Table 7).

Several trends consistent with those established above emerged from these quantitative data. With the exception of compound 112i, mono-substituted $R_2$ amine substituents comprised of a straight alkyl chain (139b, 139e, 139i), an aromatic ring (87b, 89b, 112b), or an amide functionality (115i, 116i) did not inhibit purified Eis. Compounds with $R_2$ substituents containing a diamine separated by two carbon atoms with the second amine present in a cyclohexyl ring all displayed good to moderate Eis inhibition. However, no conclusion could be formed as to what type of cyclohexyl ring was best, an unsubstituted (33a), a morpholino (35e, g, h, and i), or a piperazinyl (36d or 37b) ring, as most $IC_{50}$ values were similar for these compounds. Compound 13i with a diamine separated by three carbons at the $R_2$ position and the m,p-dimethylphenyl group at the $R_1$ position was found to be the most potent Eis inhibitor ($IC_{50}$=0.054±0.002 μM). Interestingly, compound 46b with a cyclohexyl ring directly attached to the core scaffold followed by a second piperazine ring in the para-position was found to be the second best Eis inhibitor ($IC_{50}$=0.092±0.021 μM). These results indicate that both a rotationally free alkyl chain (as in compound 13i) or cyclically restricted alkyl linkers could be useful in designing Mtb Eis inhibitors.

TABLE 7

Eis inhibition $IC_{50}$ values of tested compounds and the effect of the compounds on kanamycin A MIC values against H37Rv and K204 Mtb strains.

| Cpd | $IC_{50}$ (μM)[a] | Concentration tested (μM)[b] | H37Rv $MIC_{KAN}$ (μg/mL)[c] | K204 $MIC_{KAN}$ (μg/mL)[d] |
|---|---|---|---|---|
| — | — | — | 1.25 | 10 |
| 3i | 0.120 ± 0.035 | 12 | 0.625 | 1.25 |
| 6b | 0.152 ± 0.045 | 15.2 | 0.625 | 2.5 |
| 7b | 0.102 ± 0.034 | 10.2 | 0.625 | 2.5 |
| 8a | 2.85 ± 0.26 | 184.5 | 0.625-1.25 | 5 |
| 8e | 0.200 ± 0.036 | 20 | 0.625 | 2.5-5 |
| 11c | 0.238 ± 0.089 | 23.8 | 0.625 | 1.25 |
| 12e | 0.183 ± 0.043 | 18.3 | 0.625 | 2.5 |
| 13a | 2.82 ± 0.21 | 282.3 | 0.625 | 2.5 |
| 13e | 0.331 ± 0.071 | 33.1 | 0.625 | 2.5 |
| 13g | 0.234 ± 0.060 | 23.4 | 0.625 | 2.5-5 |
| 13i | 0.054 ± 0.002 | 5.42 | 0.625 | 5 |
| 14c | 0.112 ± 0.008 | 11.2 | 0.625 | 5 |
| 15e | 0.535 ± 0.045 | 53.5 | 0.625-1.25 | 5 |
| 15f | 0.148 ± 0.016 | 14.8 | 0.625-1.25 | 10 |
| 17i | 0.232 ± 0.038 | 23.2 | 0.625-1.25 | 5 |
| 33a | 0.123 ± 0.023 | 13.2 | 0.625 | 5 |
| 35e | >200 | 20 | 0.625 | 5 |
| 35g | 2.49 ± 0.49 | 100 | 0.625 | 2.5 |
| 35h | 3.23 ± 0.99 | 100 | 0.625 | 2.5 |
| 35i | 0.985 ± 0.190 | 98.5 | 0.625 | 2.5 |
| 36d | 0.152 ± 0.031 | 15.3 | 0.625 | 2.5-5 |
| 37b | 0.657 ± 0.105 | 65.7 | 0.625 | 2.5-5 |
| 37d | >200 | 20 | 0.625-1.25 | 5-10 |
| 46a | 0.432 ± 0.057 | 43.2 | 0.625-1.25 | 10 |
| 46b | 0.092 ± 0.021 | 9.21 | 0.625-1.25 | 5 |
| 46c | 0.109 ± 0.022 | 10.9 | 0.625 | 2.5 |
| 46h | 0.135 ± 0.031 | 13.5 | 0.625 | 5 |
| 52i | 0.580 ± 0.096 | 58 | 0.625 | 2.5 |
| 62i | 0.386 ± 0.080 | 38.6 | 0.625 | 5 |
| 81b | 1.25 ± 0.22 | 124.8 | 0.625 | 2.5-5 |
| 81g | 1.42 ± 0.42 | 142.3 | 0.625 | 2.5 |
| 87b | >200 | 20 | 1.25 | 10 |
| 89b | >200 | 20 | 1.25 | 10 |
| 112b | >200 | 20 | 0.625 | 10 |
| 112i | 0.621 ± 0.229 | 62.1 | 0.625 | 5 |
| 115i | >200 | 20 | 0.625 | 10 |
| 116i | >200 | 20 | 1.25 | 10 |
| 139b | >200 | 20 | 0.625 | 10 |
| 139e | >200 | 20 | 1.25 | 10 |
| 139i | >200 | 20 | 1.25 | 10 |

[a]The IC50 values in the Eis acetyltransferase assay.
[b]At these concentrations, these compounds did not inhibit the growth of H37Rv or that of K204 Mtb, when tested in the absence of KAN.
[c]KAN MIC values for H37Rv Mtb in the absence (first line) and in the presence of each compound at the specified concentrations.
[d]Same as [c], but for K204 Mtb.

To establish whether the inhibitors identified were specific to Eis over AACs from other families, compounds 46b and 46c were tested against AAC(6')-Ie/APH(2")-Ia from Staphylococcus aureus, AAC(3)-IV from E. coli, and AAC (2')-Ic from Mtb. Under optimal reaction conditions for each enzyme, no inhibition by either compound was observed with any of these AACs. These data demonstrate that the compounds are exquisitely selective for Mtb Eis over other AACs.

Eis Inhibitors Abolish Eis-Mediated Resistance of Mtb to KAN.

Having identified inhibitors of purified Mtb Eis enzyme, we next set to determine their activity in cellulo. Mycobacteria are notorious for their waxy cell wall that is difficult to penetrate for small molecules. Therefore, we anticipated that not all of the compounds that exhibited inhibition of purified Eis would be effective in cell cultures. We measured the effect of the forty selected compounds (at a concentration of 100-fold higher than their $IC_{50}$ values) on KAN MIC values against Mtb K204, a KAN-resistant strain bearing a clinically observed eis promoter mutation known to upregulate Eis production (Table 7). In the KAN-susceptible H37Rv strain, the MIC value of KAN is 1.25 μg/mL, whereas in the KAN-resistant K204 strain, the MIC value of KAN is 10 μg/mL. As expected, compounds that did not inhibit purified Mtb Eis (35e, 37d, 87b, 89b, 112b, 115i, 116i, and 139b, e, and i) did not overcome resistance to KAN in Mtb K204. 28 of the remaining 30 Eis inhibitors resulted in at least a 2-fold reduction in KAN MIC against Mtb K204, with two of these compounds, 3i and 11c, lowering KAN MIC 8-fold, down to the level of the KAN-susceptible H37Rv strain. Not unexpectedly, among very potent inhibitors of the enzymatic activity of Eis in vitro, there were some compounds that had little or no effect at sensitizing the resistant Mtb strain K204 to KAN. The compounds that reduced the MIC value of the KAN-resistant Mtb strain 4-fold had $IC_{50}$ values that ranged from 0.102±0.034 to 3.23±0.99 μM, emphasizing the notion that in vitro and in cellulo or in vivo activities need not be perfectly correlated.

Crystal Structures of Eis-Inhibitor Complexes Reveal the Inhibition Mechanism.

Figure 4A:
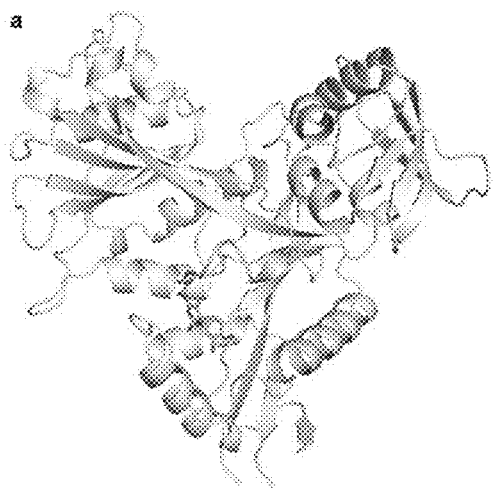
FIG. 4 provides crystal structures of EisC204A from Mtb in complex with 13g (a and b) and 11c (c and d). The overall views of the Eis monomer with the inhibitors bound (a and c) and zoom-in views of the active site (b and d) show that the inhibitors occupy a site overlapping with the AG substrate-binding site. The $F_o$-$F_c$ omit map contoured at 3a is shown by the mesh. Inhibitor interacting residues are shown as sticks. Water molecules mediating inhibitor binding are shown as navy blue spheres. The side chain of Asp26 and the backbone of this residue and its neighbors adopt different conformations in the two complexes. The CoA molecule was observed in the same position as in previously reported structures, with the phosphopantetheinyl arm exhibiting disorder and is not shown for the sake of clarity.
Figure 4B:
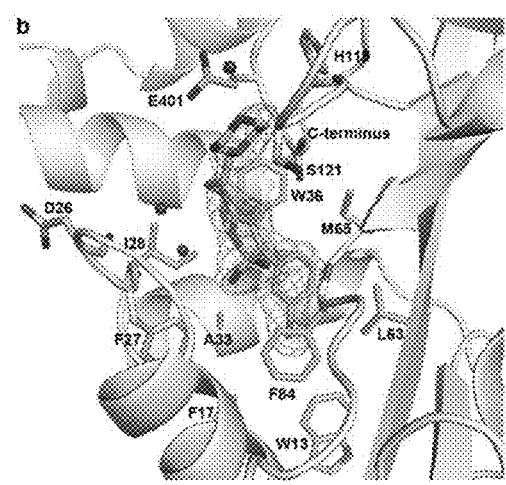
Figure 4C:
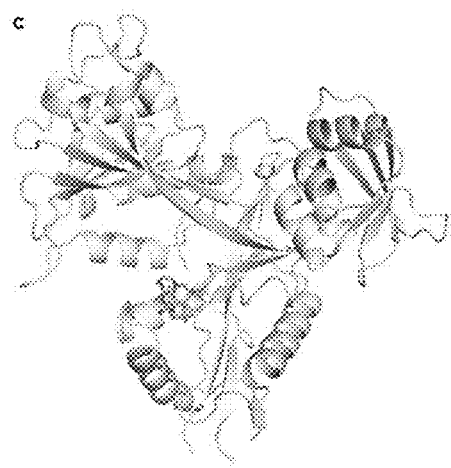
Figure 4D:
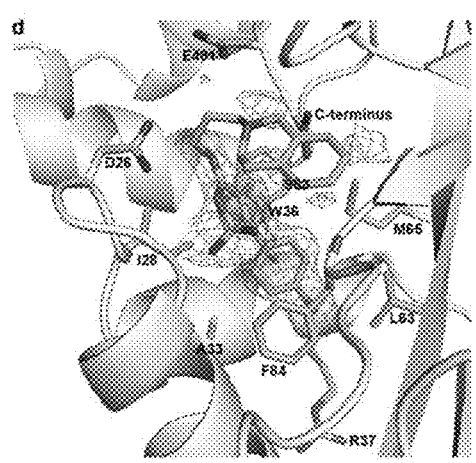

To elucidate the mechanism of Eis inhibition by the sulfonyl isothiazole-containing compounds, rationalize the observed SAR, and guide future rational inhibitor design, 2.2 Å-resolution crystal structures of Eis in complex with CoA and inhibitors 13g and 11c (FIGS. 4a,c) were determined, which displayed both potent inhibition of Eis acetylation in vitro and the KAN resistance abolishing effect in the Mtb cultures. Both inhibitors and their chemical features were clearly distinguishable and modeled into strong $F_o$-$F_c$ electron density (FIG. 4b,d). The only exception was the 1,2,3,4-tetrahydroisoquinoline (THQ) group of 11c, for which only partial electron density was observed (FIG. 4d), likely due to a somewhat dynamic behavior of this highly hydrophobic group in a partially polar environment, as allowed by the flexible diamine linkage. No other significant difference electron density that could be attributed to a bound inhibitor was observed elsewhere. Both inhibitors exhibited high steric complementarity with the Eis surface. The binding site for both inhibitors overlapped with the aminoglycoside substrate-binding site, as was recently established by the structure of Mtb Eis in complex with CoA and tobramycin. In addition, the $R_2$ groups of both inhibitors reached the C-terminal carboxyl group of Eis, which was proposed to serve as the general base in the acetyl transfer reaction. Therefore, these crystal structures indicate that the inhibitors block access of aminoglycosides to the active site of the enzyme. Explaining the critical role of the sulfonyl isothiazole core, this group is bound in the same location and orientation in both Eis-inhibitor structures (FIG. 4b,d). Remarkably, despite the nearly identical positions of this group, there are differences in how this group interacts with the protein for the two inhibitors. These differences are due to significant induced-fit conformational changes in the region spanning residues 26-31 of Eis (FIG. 4b,d), which uniquely adapts to bind the two structurally different $R_2$ groups. For inhibitor 13g (FIG. 4a,b), one of the sulfonyl oxygens forms a direct hydrogen bond with the main chain amide nitrogen of Phe84 and the ring nitrogen forms a water-mediated hydrogen bond with the main chain amide nitrogen of Ile28. In this case, the Eis conformation resembles that observed in a previously reported crystal structure with the aminoglycoside-binding pocket unoccupied. Inhibitor 11c does not make any water-mediated contacts due to a small positional shift of the inhibitor and a conformational change of Eis. Instead, the two sulfonyl oxygens are at a distance of ~4 Å, consistent with the stabilizing van der Waals and electrostatic interactions. The isothiazole ring is sterically sandwiched between the side chains of Ile28 and Ser83 in one direction and between the side chains of Phe24 and Trp36 in the orthogonal direction. The $R_1$ groups of the two compounds are almost coplanar and fit neatly into a nearly fully nonpolar environment of side chains Leu63, Trp13, and Ala33, the aliphatic stem of Arg37, Met65, and Phe84, explaining the nonpolar phenyl ring with small substitutions as effective $R_1$ groups (Table 5). Such environment, devoid of hydrogen bond donors or acceptors is appropriate for accommodating halogen substituents, as is the case with 11c and 13g. The halogens can be accommodated in the para and/or one, but not both meta positions. Substitutions at both meta positions would not be accommodated, as reflected in the list of potent inhibitors (FIG. 3, Table 5), since one of them would clash sterically with the side chain of Met65. In contrast with $R_1$, the conformations of the $R_2$ groups of the two inhibitors are drastically different with one exception—the positively charged ring nitrogen of $R_2$ occupies nearly the same location where it forms a salt bridge with the carboxyl group of Glu401 in both structures. Besides this interaction, $R_2$ group of compound 13g makes steric and weak electrostatic interactions with His119, Ser121, Glu401, and the C-terminal carboxyl group (weakly electrostatically interacting with the stem N) on one side and making water-mediated steric interactions with region 26-31 on the other side. In contrast, for the $R_2$ of the compound 11c: while the interactions with one face of this group are made with the same amino acid residues, the other face interacts directly through hydrophobic and steric interactions with the region 26-31, which is in a different conformation. Most prominently, the side chain of Asp26 is flipped to interact with the stem, and Phe24 orthogonally stacks against the double ring. Because the $R_1$ group abuts the hydrophobic wall, whereas $R_2$ group points towards the more extended end of the substrate binding channel, there is more variability in both the identity and the size of $R_2$ substituents, as exhibited in the list of effective $R_2$ groups (Table 4).

Discussion

While it has been met with initial skepticism, target-based rational drug design is now gaining momentum and is widely used in industrial and academic drug discovery pipelines, due to advances in HTS technology, robust assay development practices and availability of large and diverse chemical libraries. Prominent examples of successful rational drug design are HIV protease inhibitors ritonavir and the anticancer drug Gleevec. Here, we report the discovery and initial preclinical development of novel first-in-class sulfonyl isothiazole inhibitors of a unique acetyltransferase Eis from Mtb as an agent that overcomes one mechanism of resistance to KAN in Mtb. Among the diverse pool of compounds tested, we found agents that we validated as potent inhibitors of Eis both in the test tube and in the relevant Mtb cultures. Potencies in mid-nM range appear to be achieved through binding of the compounds via steric complementarity, hydrophobic and hydrogen bonding interactions. While one substituent group ($R_1$) is relatively unchangeable in terms of its size and physico-chemical properties, the other group ($R_2$) can greatly vary. The crystal structures of Eis-inhibitor complexes demonstrate that binding to variable structures is achieved by conformational plasticity of the aminoglycoside-binding site of Eis, which adapts to different $R_2$ groups, while the $R_1$ group achieves a nearly rigid-body fit. Binding of the two inhibitors of Eis investigated structurally differs not only in protein conformation, but also in the presence or absence of water-mediated contacts.

Aminoglycosides are among the antibiotics of last resort for MDR and XDR-TB patients, and resistance to them strongly decreases the chances of a favorable treatment outcome. The strategy of using KAN in combination with an Eis inhibitor is meant not only to overcome KAN resistance due to Eis upregulation, but also to curb emergence of new resistant strains by mutagenesis of the eis promoter, as such mutation would not have survival benefit in the face of combination therapy. This study not only validates AAC's as drug targets, but has set an important precedent for HTS-driven discovery for AACs that cause resistance in clinically useful non-TB pathogens, such as AAC(3) and AAC(6') in *Klebsiella pneumoniae* (32-34). As with TB, such inhibitory agents could play an important role in both overcoming existing resistance and curbing the acquisition of resistance.

In conclusion, we identified potent inhibitors of Eis enzymatic activity with resulting sensitization of KAN-resistant Mtb cells, in which the resistance to KAN is caused by Eis upregulation. The inhibitors bind in the AG binding pocket blocking the access of AGs to the active site of the enzyme. The inhibitor binding is accompanied by induced-fit conformational changes of the protein. These compounds have a great potential for further development as KAN adjuvants in Mtb.

Protocols:

Detailed versions of the abbreviated protocols below are provided in the Materials and Methods.

Protein, Reagents, and Small-Molecule Libraries.

The wild-type Eis from Mtb (4), EisC204A (10), AAC(6')/APH(2") (35), AAC(3)-IV (35), and AAC(2')-Ic (4) were overexpressed and purified as previously reported, with minor modifications. All reagents were purchased from Sigma with the exception of Albumin-dextrose-catalase (ADC), which was from BD Biosciences. Eis was screened at the Center for Chemical Genomics (CCG, University of Michigan) against 123,000 compounds from three libraries. Compounds were retested as fresh powder samples purchased from ChemDiv.

Eis Chemical Library Screening and Hit Validation.

Figure 5:
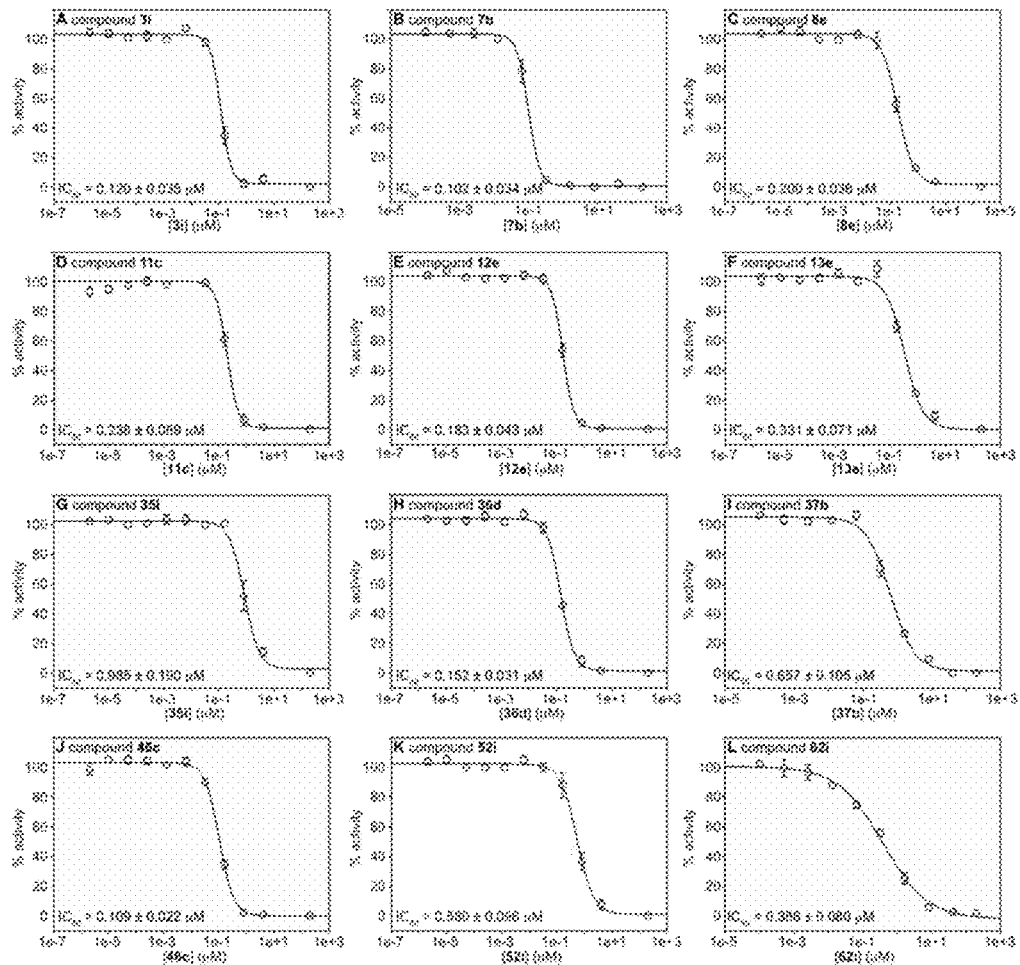
FIG. 5 includes representative $IC_{50}$ plots for the inhibition of Eis using fresh powder for several of the inhibitors identified in Table 5.

Screening of small-molecule libraries, hit validation, and dose response analysis (represented by FIG. 5) were performed as previously described.

Inhibitor Selectivity.

Compounds 46b and 46c were tested against three additional AAC enzymes: AAC(6')/APH(2"), AAC(3)-IV, and AAC(2')-Ic at optimal reaction conditions for each enzyme.

Mycobacterial MIC Determination by Alamar Blue Assay.

The assay was done with Mtb strains H37Rv and K204 in 7H9 broth. Compounds were tested at either 100× $IC_{50}$ (if known) or 20 µM for their inhibitory effect on Mtb growth and on KAN MIC in these two strains.

Crystallization, Diffraction Data Collection, and Structure Determination and Refinement of EisC204A-CoA-Inhibitor Complexes.

Crystals were grown by the hanging drop method and then underwent a complex harvesting process. The cryoprotectant solution contained 0.5 mM inhibitor. The diffraction data were collected at synchrotron beamline 22-ID of the Advanced Photon Source at the Argonne National Laboratory (Argonne, Ill.) at 100 K. The data were processed and the structures were built and refined by previously described methods.

Material and Methods

Example 1

1. Chemistry
1.1. General.

All reagents were purchased from commercial sources and used without purification. TLC analyses were performed on silica gel plates (pre-coated on aluminum; 0.20 mm thickness with fluorescent indicator $UV_{254}$) and were visualized by UV or charring in $KMnO_4$ stains. $^1H$ and $^{13}C$ NMR spectra were collected on 400 MHz NMR spectrometer (VARIAN INOVA) using $(CD_3)_2SO$. Chemical shifts are reported in parts per million (ppm) and are referenced to residual solvent peaks. All reactions were conducted under nitrogen atmosphere and all yields reported refer to isolated yields. The known compound A was characterized by $^1H$ NMR and is in complete agreement with sample reported elsewhere. All new compounds were characterized by $^1H$, $^{13}C$ NMR, and mass spectrometry.

1.2. Synthesis and Characterization of Sulfonamides Generated in this Study.

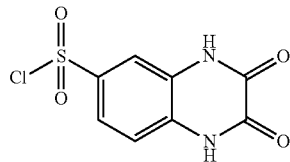 [SMILES: O=c1[nH]c2ccc(S(=O)(=O)Cl)cc2[nH]c1=O]

Synthesis of Compound A.

The known compound A was prepared following a previously published protocol.[1] Chlorosulfonic acid (20.53 mL, 308.36 mmol) was added to quinoxaline-2,3-diol (5.00 g, 30.83 mmol). The reaction mixture was then refluxed for 12 h. After cooling to room temperature, the reaction mixture was carefully poured onto ice, filtered, and the precipitate was washed with $H_2O$ (50 mL). The solid was collected and recrystallized with toluene to afford A (7.07 g, 88%) as a white solid: $^1H$ NMR (400 MHz, $(CD_3)_2SO$, which matches lit.) δ 11.97 (s, 1H), 11.94 (s, 1H), 7.43 (d, J=1.6 Hz, 1H), 7.30 (dd, J=8.4, 1.6 Hz, 1H), 7.04 (d, J=8.4 Hz, 1H).

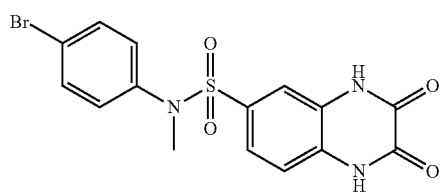

General Procedure for the Synthesis of Sulfonamides (e.g., Preparation of Compound 29).

A solution of compound A (0.30 g, 1.15 mmol) and 4-bromo-N-methylaniline (0.29 mL, 2.30 mmol) in DMF (6 mL) was stirred at room temperature for 12 h. $H_2O$ was added to the reaction mixture and the formed precipitate was filtered and washed with $H_2O$ (10 mL) to yield 29 (0.21 g, 45%) as a purple solid: $^1H$ NMR (400 MHz, $(CD_3)_2SO$) δ 12.27 (s, 1H), 12.00 (s, 1H), 7.55 (app dt, J=9.6, 3.2 Hz, 2H), 7.25 (d, J=9.6 Hz, 2H), 7.24 (s, 1H), 7.07 (app dt, J=9.2, 3.2 Hz, 2H), 3.09 (s, 3H); $^{13}C$ NMR (100 MHz, $(CD_3)_2SO$) δ 155.2, 154.8, 140.4, 131.9, 129.8, 129.3, 128.4, 125.9, 122.4, 120.2, 115.5, 114.4, 37.7; LRMS m/z calcd for $C_{15}H_{13}BrN_3O_4S$ $[M+H]^+$: 410.0; found 410.8.

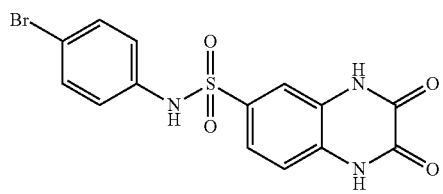 [SMILES: O=c1[nH]c2ccc(S(=O)(=O)Nc3ccc(Br)cc3)cc2[nH]c1=O]

Preparation of Compound 30.

As described for the synthesis of compound 29, compound A (0.30 g, 1.15 mmol), 4-bromoaniline (0.39 g, 2.30 mmol), and DMF (6 mL) were used to afford compound 30 (0.21 g, 47%) as a light yellow solid: $^1H$ NMR (400 MHz, $(CD_3)_2SO$) δ 12.17 (s, 1H), 12.09 (s, 1H), 10.49 (br s, 1H), 7.51 (d, J=1.6 Hz, 1H), 7.45 (dd, J=8.0, 1.6 Hz, 1H), 7.41 (app dt, J=9.6, 2.8 Hz, 2H), 7.19 (d, J=8.0 Hz, 1H), 7.04 (app dt, J=9.6, 2.8 Hz, 2H); $^{13}C$ NMR (100 MHz, $(CD_3)_2SO$) δ 155.2, 154.9, 137.1, 133.1, 132.1, 129.5, 125.9, 121.9, 121.5, 116.2, 115.6, 113.7, 113.6; LRMS m/z calcd for $C_{14}H_{11}N_3O_4SBr$ [M+H]$^+$: 396.0; found 396.8.

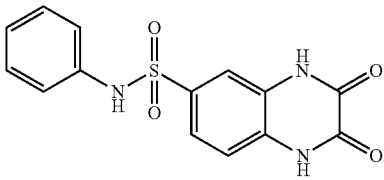 [SMILES: O=c1[nH]c2ccc(S(=O)(=O)Nc3ccccc3)cc2[nH]c1=O]

Preparation of Compound 31.

As described for the synthesis of compound 29, compound A (0.30 g, 1.15 mmol), aniline (0.21 mL, 2.30 mmol), and DMF (6 mL) were used to afford compound 31 (0.22 g, 61%) as a light yellow solid: $^1$H NMR (400 MHz, (CD$_3$)$_2$SO) δ 12.15 (s, 1H), 12.08 (s, 1H), 10.32 (br s, 1H), 7.53 (s, 1H), 7.44 (d, J=8.4 Hz, 1H), 7.24-7.17 (m, 3H), 7.08 (d, J=8.4 Hz, 2H), 7.02 (t, J=7.2 Hz, 1H); $^{13}$C NMR (100 MHz, (CD$_3$)$_2$SO) δ 155.2, 154.9, 137.6, 133.5, 129.3, 129.2, 125.8, 124.0, 121.5, 119.9, 115.5, 113.7; LRMS m/z calcd for $C_{14}H_{12}N_3O_4S$ [M+H]$^+$: 318.1; found 318.8.

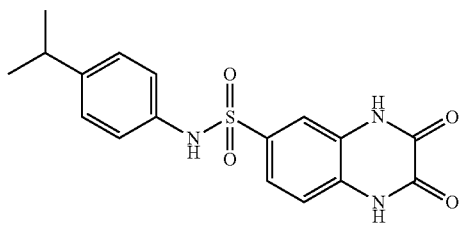 [SMILES: CC(C)c1ccc(NS(=O)(=O)c2ccc3[nH]c(=O)c(=O)[nH]c3c2)cc1]

Preparation of Compound 32.

As described for the synthesis of compound 29, compound A (0.30 g, 1.15 mmol), 4-isopropylaniline (0.31 g, 2.30 mmol), and DMF (6 mL) were used to afford compound 32 (0.24 g, 59%) as a pink solid: $^1$H NMR (400 MHz, (CD$_3$)$_2$SO) δ 12.15 (s, 1H), 12.08 (s, 1H), 10.21 (br s, 1H), 7.52 (d, J=2.0 Hz, 1H), 7.44 (dd, J=8.4, 2.0 Hz, 1H), 7.18 (d, J=8.4 Hz, 1H), 7.09 (app dt, J=8.4, 2.0 Hz, 2H), 6.99 (app dt, J=8.4, 2.0 Hz, 2H), 2.76 (hep., J=6.8 Hz, 1H), 1.10 (d, J=6.8 Hz, 6H); $^{13}$C NMR (100 MHz, (CD$_3$)$_2$SO) δ 155.2, 155.0, 144.1, 135.2, 133.8, 129.3, 127.0, 125.8, 121.5, 120.3, 115.5, 113.75, 113.69, 32.7, 23.8; LRMS m/z calcd for $C_{17}H_{18}N_3O_4S$ [M+H]$^+$: 360.1; found 360.8.

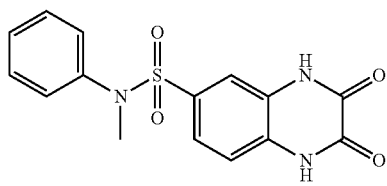 [SMILES: CN(c1ccccc1)S(=O)(=O)c1ccc2[nH]c(=O)c(=O)[nH]c2c1]

Preparation of Compound 33.

As described for the synthesis of compound 29, compound A (0.30 g, 1.15 mmol), N-methylaniline (0.25 mL, 2.30 mmol), and DMF (6 mL) were used to afford compound 33 (0.27 g, 71%) as a white solid: $^1$H NMR (400 MHz, (CD$_3$)$_2$SO) δ 12.24 (s, 1H), 12.00 (s, 1H), 7.34 (d, J=8.0 Hz, 2H), 7.31-7.29 (m, 2H), 7.22 (s, 1H), 7.20 (d, J=1.6 Hz, 1H), 7.10 (m, 2H), 3.12 (s, 3H); $^{13}$C NMR (100 MHz, (CD$_3$)$_2$SO) δ 155.2, 154.8, 141.1, 129.8, 129.6, 129.0, 127.4, 126.4, 125.9, 122.3, 120.0, 115.4, 114.5, 114.4, 38.0; LRMS m/z calcd for $C_{15}H_{14}N_3O_4S$ [M+H]$^+$: 332.1; found 332.8.

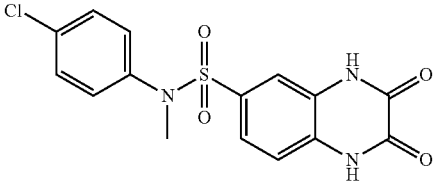 [SMILES: CN(c1ccc(Cl)cc1)S(=O)(=O)c1ccc2[nH]c(=O)c(=O)[nH]c2c1]

Preparation of Compound 34.

As described for the synthesis of compound 29, compound A (0.30 g, 1.15 mmol), 4-chloro-N-methylaniline (0.28 mL, 2.30 mmol), and DMF (6 mL) were used to afford compound 34 (0.16 g, 38%) as a white solid: $^1$H NMR (400 MHz, (CD$_3$)$_2$SO) δ 12.26 (s, 1H), 12.00 (s, 1H), 7.42 (d, J=8.8 Hz, 2H), 7.24 (d, J=8.8 Hz, 2H), 7.23 (s, 1H), 7.12 (m, 2H), 3.09 (s, 3H); $^{13}$C NMR (100 MHz, (CD$_3$)$_2$SO) δ 155.2, 154.8, 140.0, 131.7, 129.8, 129.3, 128.9, 128.6, 128.1, 125.9, 122.4, 115.5, 114.5, 37.8; LRMS m/z calcd for $C_{15}H_{13}ClN_3O_4S$ [M+H]$^+$: 366.0; found 366.8.

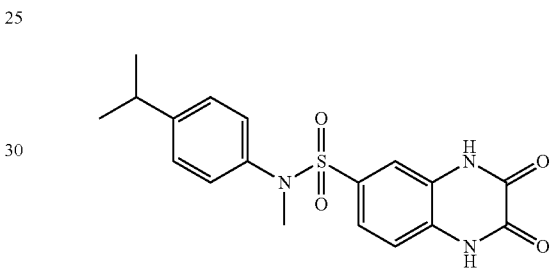

Preparation of Compound 35.

As described for the synthesis of compound 29, compound A (0.30 g, 1.15 mmol), 4-isopropyl-N-methylaniline (0.34 g, 2.30 mmol), and DMF (6 mL) were used to afford compound 35 (0.20 g, 48%) as a white solid: $^1$H NMR (400 MHz, (CD$_3$)$_2$SO) δ 12.25 (s, 1H), 12.00 (s, 1H), 7.34 (s, 1H), 7.23 (m, 1H), 7.21 (dt, J=8.8, 2.4 Hz, 2H), 7.00 (dt, J=8.8, 2.4 Hz, 2H), 3.09 (s, 3H), 2.88 (hep., J=7.2 Hz, 1H), 1.18 (d, J=7.2 Hz, 6H); $^{13}$C NMR (100 MHz, (CD$_3$)$_2$SO) δ 155.2, 154.8, 147.5, 138.8, 130.2, 129.5, 126.8, 126.4, 125.9, 122.3, 115.5, 114.5, 114.4, 38.2, 33.0, 23.8; LRMS m/z calcd for $C_{18}H_{20}N_3O_4S$ [M+H]$^+$: 374.1; found 374.8.

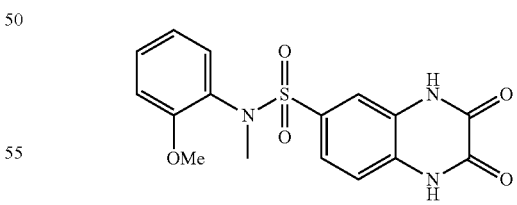

Preparation of Compound 36.

As described for the synthesis of compound 29, compound A (0.30 g, 1.15 mmol), 2-methoxy-N-methylaniline (0.31 mL, 2.30 mmol), and DMF (6 mL) were used to afford compound 36 (0.12 g, 29%) as a white solid: $^1$H NMR (400 MHz, (CD$_3$)$_2$SO) δ 12.23 (s, 1H), 11.99 (s, 1H), 7.40 (d, J=2.0 Hz, 1H), 7.38-7.34 (m, 1H), 7.33-7.30 (m, 1H), 7.24 (d, J=8.4 Hz, 1H), 7.14 (dd, J=8.0, 1.2 Hz, 1H), 7.01 (dd, J=8.0, 1.2 Hz, 1H), 6.93 (td, J=7.6, 1.2 Hz, 1H), 3.36 (s, 3H), 3.08 (s, 3H); $^{13}$C NMR (100 MHz, (CD$_3$)$_2$SO) δ 156.2, 155.3, 154.9, 132.9, 131.0, 129.8, 129.2, 128.6, 125.7, 122.2, 120.4, 115.2, 114.2, 112.6, 55.2, 37.7; LRMS m/z calcd for C$_{16}$H$_{16}$BrN$_3$O$_5$S [M+H]$^+$: 362.1; found 362.8.

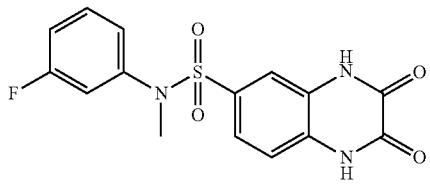 [SMILES: CN(c1cccc(F)c1)S(=O)(=O)c1ccc2[nH]c(=O)c(=O)[nH]c2c1]

Preparation of Compound 37.

As described for the synthesis of compound 29, compound A (0.30 g, 1.15 mmol), 3-fluoro-N-methylaniline (0.26 mL, 2.30 mmol), and DMF (6 mL) were used to afford compound 37 (0.06 g, 15%) as a white solid: $^1$H NMR (400 MHz, (CD$_3$)$_2$SO) δ 12.26 (s, 1H), 12.00 (s, 1H), 7.39 (app q, J=8.0 Hz, 1H), 7.30 (s, 1H), 7.23 (m, 2H), 7.16 (td, J=8.8, 5.6 Hz, 1H), 7.03 (dt, J=10.8, 2.4 Hz, 1H), 6.99 (m, 1H), 3.12 (s, 3H); $^{13}$C NMR (100 MHz, (CD$_3$)$_2$SO) δ 163.0, 160.6, 155.2, 154.8, 142.8, 142.7, 130.5, 130.4, 129.8, 129.4, 125.9, 122.3, 122.09, 122.06, 115.5, 114.4, 114.2, 114.0, 113.4, 113.1, 37.7; LRMS m/z calcd for C$_{15}$H$_{13}$FN$_3$O$_4$S [M+H]$^+$: 350.1; found 350.8.

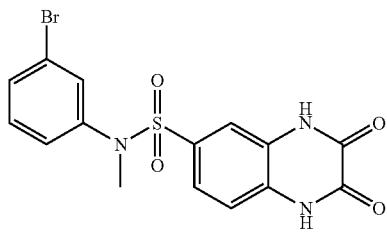 [SMILES: CN(c1cccc(Br)c1)S(=O)(=O)c1ccc2[nH]c(=O)c(=O)[nH]c2c1]

Preparation of Compound 38.

As described for the synthesis of compound 29, compound A (0.30 g, 1.15 mmol), 3-bromo-N-methylaniline (0.29 mL, 2.30 mmol), and DMF (6 mL) were used to afford compound 38 (0.02 g, 4%) as a white solid: $^1$H NMR (400 MHz, (CD$_3$)$_2$SO) δ 12.27 (s, 1H), 12.01 (s, 1H), 7.51 (ddd, J=7.6, 2.0, 1.2 Hz, 1H), 7.35 (t, J=2.0 Hz, 1H), 7.32 (d, J=8.0 Hz, 1H), 7.29 (m, 1H), 7.23 (m, 2H), 7.14 (ddd, J=7.6, 2.0, 1.2 Hz, 1H), 3.11 (s, 3H); $^{13}$C NMR (100 MHz, (CD$_3$)$_2$SO) δ 155.2, 154.8, 142.6, 130.8, 129.8, 129.3, 129.1, 129.0, 125.9, 125.1, 122.3, 121.3, 115.5, 114.5, 37.7; LRMS m/z calcd for C$_{15}$H$_{13}$BrN$_3$O$_4$S [M+H]$^+$: 410.0; found 410.8.

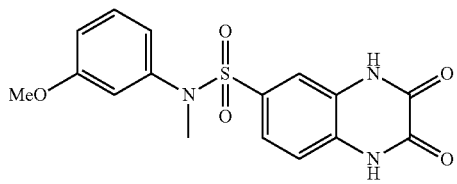 [SMILES: COc1cccc(N(C)S(=O)(=O)c2ccc3[nH]c(=O)c(=O)[nH]c3c2)c1]

Preparation of Compound 39.

As described for the synthesis of compound 29, compound A (0.20 g, 0.77 mmol), 3-methoxy-N-methylaniline (0.20 mL, 1.54 mmol), and DMF (4 mL) were used to afford compound 39 (0.05 g, 17%) as a gray solid: $^1$H NMR (400 MHz, (CD$_3$)$_2$SO) δ 12.23 (s, 1H), 11.99 (s, 1H), 7.33 (d, J=1.6 Hz, 1H), 7.27-7.22 (m, 3H), 6.88 (m, 1H), 6.67-6.65 (m, 2H), 3.70 (s, 3H), 3.11 (s, 3H); $^{13}$C NMR (100 MHz, (CD$_3$)$_2$SO) δ 159.3, 155.1, 154.8, 142.2, 130.0, 129.60, 129.57, 125.8, 122.3, 118.2, 115.4, 114.4, 112.8, 112.3, 55.2, 38.0; LRMS m/z calcd for C$_{16}$H$_{16}$N$_3$O$_5$S [M+H]$^+$: 362.1; found 362.8.

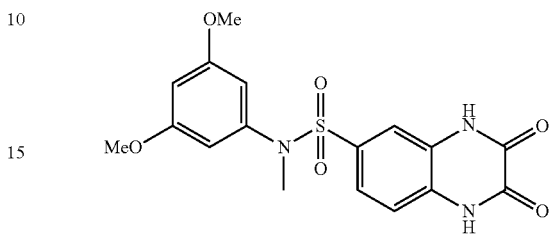

Preparation of Compound 40.

As described for the synthesis of compound 29, compound A (0.20 g, 0.77 mmol), 3,5-dimethoxy-N-methylaniline (0.26 g, 1.54 mmol), and DMF (4 mL) were used to afford compound 40 (0.03 g, 10%) as a white solid: $^1$H NMR (400 MHz, (CD$_3$)$_2$SO) δ 12.23 (s, 1H), 12.00 (s, 1H), 7.37 (d, J=2.0 Hz, 1H), 7.29 (dd, J=8.0, 2.0 Hz, 1H), 7.23 (d, J=8.0 Hz, 1H), 6.45 (t, J=2.0 Hz, 1H), 6.25 (d, J=2.0 Hz, 2H), 3.67 (s, 3H), 3.65 (s, 3H), 3.09 (s, 3H); $^{13}$C NMR (100 MHz, (CD$_3$)$_2$SO) δ 160.2, 155.2, 154.8, 142.8, 130.1, 129.6, 125.8, 122.3, 115.4, 114.4, 104.6, 99.1, 55.3, 38.0; LRMS m/z calcd for C$_{17}$H$_{18}$N$_3$O$_6$S [M+H]$^+$: 392.1; found 392.8.

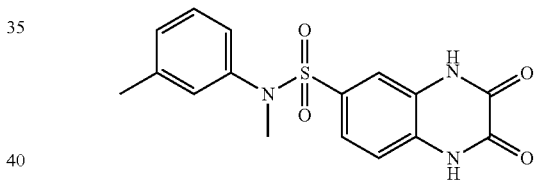

Preparation of Compound 41.

As described for the synthesis of compound 29, compound A (0.20 g, 0.77 mmol), 3-methyl-N-methylaniline (0.19 mL, 1.54 mmol), and DMF (4 mL) were used to afford compound 41 (0.15 g, 58%) as a white solid: $^1$H NMR (400 MHz, (CD$_3$)$_2$SO) δ 12.23 (s, 1H), 11.98 (s, 1H), 7.32 (m, 1H), 7.24-7.20 (m, 3H), 7.11 (m, 1H), 6.96 (m, 1H), 6.85 (m, 1H), 3.09 (s, 3H), 2.27 (s, 3H); $^{13}$C NMR (100 MHz, (CD$_3$)$_2$SO) δ 155.2, 154.8, 141.1, 138.3, 130.0, 129.5, 128.7, 128.0, 127.1, 125.8, 123.2, 122.3, 115.4, 114.4, 38.0, 20.8; LRMS m/z calcd for C$_{16}$H$_{16}$N$_3$O$_4$S [M+H]$^+$: 346.1; found 346.8.

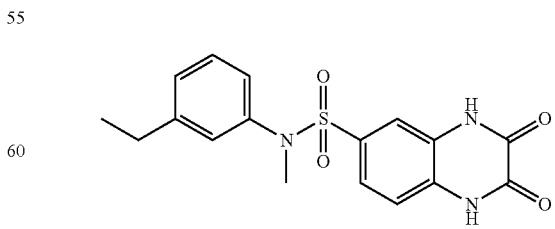

Preparation of Compound 42.

As described for the synthesis of compound 29, compound A (0.20 g, 0.77 mmol), 3-ethyl-N-methylaniline (0.21 g, 1.54 mmol), and DMF (4 mL) were used to afford compound 42 (0.20 g, 74%) as a white solid: $^1$H NMR (400 MHz, (CD$_3$)$_2$SO) δ 12.23 (s, 1H), 11.98 (s, 1H), 7.30 (s, 1H), 7.25 (t, J=8.8, 1H), 7.23 (s, 1H), 7.14 (d, J=7.2 Hz, 1H), 6.89 (m, 2H), 3.10 (s, 3H), 2.55 (q, J=8.0 Hz, 2H), 1.09 (t, J=8.0 Hz, 3H); $^{13}$C NMR (100 MHz, (CD$_3$)$_2$SO) δ 155.1, 154.8, 144.6, 141.1, 129.9, 129.5, 128.8, 126.9, 125.8, 123.7, 122.3, 115.4. 114.5, 38.1, 27.9, 15.4; LRMS m/z calcd for C$_{17}$H$_{18}$N$_3$O$_4$S [M+H]$^+$: 360.1; found 360.8.

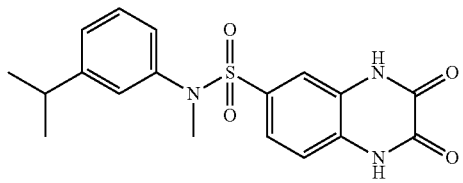 [SMILES: CC(C)c1cccc(N(C)S(=O)(=O)c2ccc3[nH]c(=O)c(=O)[nH]c3c2)c1]

Preparation of Compound 43.

As described for the synthesis of compound 29, compound A (0.07 g, 0.27 mmol), 3-i-propyl-N-methylaniline (0.08 g, 0.54 mmol), and DMF (1.5 mL) were used to afford compound 43 (0.06 g, 60%) as a white solid: $^1$H NMR (400 MHz, (CD$_3$)$_2$SO) δ 12.25 (s, 1H), 11.99 (s, 1H), 7.27 (d, J=8.0 Hz, 1H), 7.26 (t, J=8.0 Hz, 1H), 7.22 (d, J=2.0 Hz, 1H), 7.21 (dd, J=8.4, 1.6 Hz, 1H), 7.17 (dt, J=8.0, 1.2 Hz, 1H), 6.92 (ddd, J=8.0, 2.0, 1.2 Hz, 1H), 6.85 (t, J=2.0 Hz, 1H), 3.10 (s, 3H), 2.81 (hep., J=6.8 Hz, 1H), 1.10 (d, J=6.8 Hz, 6H); $^{13}$C NMR (100 MHz, (CD$_3$)$_2$SO) δ 155.2, 154.8, 149.3, 141.1, 129.9, 129.5, 128.8, 125.8, 125.5, 124.3, 124.2, 122.3, 115.4, 114.6, 38.1, 33.1, 23.6; LRMS m/z calcd for C$_{18}$H$_{19}$N$_3$O$_4$S [M+H]$^+$: 373.1; found 373.8.

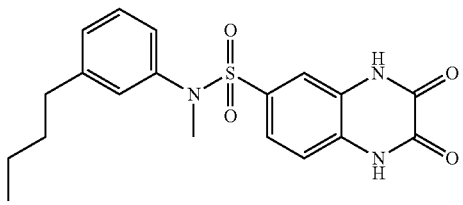 [SMILES: CCCCc1cccc(N(C)S(=O)(=O)c2ccc3[nH]c(=O)c(=O)[nH]c3c2)c1]

Preparation of Compound 44.

As described for the synthesis of compound 29, compound A (0.06 g, 0.25 mmol), 3-butyl-N-methylaniline (0.08 g, 0.49 mmol), and DMF (1.5 mL) were used to afford compound 44 (0.10 g, 100%) as a pink solid: $^1$H NMR (400 MHz, (CD$_3$)$_2$SO) δ 12.26 (s, 1H), 11.98 (s, 1H), 7.27 (m, 1H), 7.25 (s, 1H), 7.22 (m, 2H), 7.11 (d, J=8.0 Hz, 1H), 6.94 (m, 1H), 6.80 (t, J=2.0 Hz, 1H), 3.11 (s, 3H), 1.42-1.37 (m, 3H), 1.24-1.17 (m, 3H), 0.82 (t, J=7.6 Hz, 3H); $^{13}$C NMR (100 MHz, (CD$_3$)$_2$SO) δ 155.2, 154.8, 143.2, 141.0, 129.9, 129.5, 128.7, 127.4, 125.9, 125.8, 124.1, 122.3, 115.4, 114.6, 38.1, 34.5, 33.0, 21.6, 13.8; LRMS m/z calcd for C$_{18}$H$_{19}$N$_3$O$_4$S [M+H]$^+$: 373.1; found 373.8.

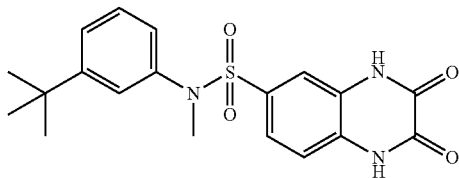 [SMILES: CN(c1cccc(C(C)(C)C)c1)S(=O)(=O)c1ccc2[nH]c(=O)c(=O)[nH]c2c1]

Preparation of Compound 45.

As described for the synthesis of compound 29, compound A (0.03 g, 0.13 mmol), 3-t-butyl-N-methylaniline (0.04 g, 0.27 mmol), and DMF (1 mL) were used to afford compound 45 (0.03 g, 58%) as a brown solid: $^1$H NMR (400 MHz, (CD$_3$)$_2$SO) δ 12.25 (s, 1H), 11.99 (s, 1H), 7.32 (dt, J=8.0, 1.6 Hz, 1H), 7.30-7.26 (m, 2H), 7.23 (m, 2H), 6.94 (t, J=1.6 Hz, 1H), 6.92 (d, J=1.6 Hz, 1H), 3.11 (s, 3H), 1.17 (s, 9H); $^{13}$C NMR (100 MHz, (CD$_3$)$_2$SO) δ 155.1, 154.7, 151.5, 140.9, 129.9, 129.5, 128.6, 125.7, 124.3, 124.0, 123.3, 122.3, 115.4, 114.6, 38.2, 34.3, 30.8; LRMS m/z calcd for C$_{19}$H$_{21}$N$_3$O$_4$S [M+H]$^+$: 387.1; found 387.8.

Preparation of Compound 46.

As described for the synthesis of compound 29, compound A (0.20 g, 0.77 mmol), N-methyl-2-naphthylamine (0.24 g, 1.54 mmol), and DMF (4 mL) were used to afford compound 46 (0.16 g, 55%) as an orange solid: $^1$H NMR (400 MHz, (CD$_3$)$_2$SO) δ 12.24 (s, 1H), 11.95 (s, 1H), 7.95-7.86 (m, 3H), 7.64 (d, J=2.0 Hz, 1H), 7.52 (m, 2H), 7.31-7.29 (m, 2H), 7.23 (m, 2H), 3.22 (s, 3H); $^{13}$C NMR (100 MHz, (CD$_3$)$_2$SO) δ 155.1, 154.8, 138.6, 132.9, 131.7, 129.8, 129.6, 128.5, 127.9, 127.5, 126.6, 126.4, 125.9, 124.9, 124.3, 122.4, 115.5, 114.4, 38.1; LRMS m/z calcd for C$_{19}$H$_{15}$N$_3$O$_4$S [M+H]$^+$: 381.1; found 381.8.

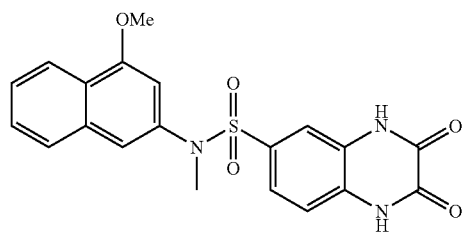 [SMILES: COc1cc(N(C)S(=O)(=O)c2ccc3[nH]c(=O)c(=O)[nH]c3c2)cc2ccccc12]

Preparation of Compound 47.

As described for the synthesis of compound 29, compound A (0.09 g, 0.35 mmol), N-methyl-4-methoxy-2-naphthylamine (0.13 g, 0.70 mmol), and DMF (2 mL) were used to afford compound 47 (0.03 g, 21%) as a yellow solid: $^1$H NMR (400 MHz, (CD$_3$)$_2$SO) δ 12.24 (s, 1H), 11.97 (s, 1H), 8.11-8.09 (m, 1H), 7.82-7.80 (m, 1H), 7.55-7.48 (m, 2H), 7.35 (d, J=2.0 Hz, 1H), 7.31 (dd, J=8.4, 2.0 Hz, 1H), 7.23 (d, J=8.4 Hz, 1H), 7.20 (d, J=1.2 Hz, 1H), 6.71 (d, J=2.0 Hz, 1H), 3.87 (s, 3H), 3.21 (s, 3H); $^{13}$C NMR (100 MHz, (CD$_3$)$_2$SO) δ 155.2, 154.9, 154.8, 139.1, 133.4, 129.9, 129.7, 127.8, 127.2, 125.9, 125.8, 123.7, 122.5, 121.3, 116.7, 115.4, 114.5, 103.9, 55.7, 38.2; LRMS m/z calcd for C$_{20}$H$_{17}$N$_3$O$_5$S [M+H]$^+$: 411.1; found 411.8.

2. Biochemistry and Biology:

2.1. Protein, Reagents, and Small-Molecule Libraries.

Recombinant Mtb Eis protein (Eis_Mtb), AAC(6')-Ie/APH(2")-Ia, AAC(3)-IV, and AAC(2')-Ic were expressed and purified as reported previously. All chemicals including 5',5-dithiobis-(2-nitrobenzoic acid) (DTNB), Tween® 80, neomycin B (NEO), kanamycin A (KAN), acetyl-CoA (Ac-CoA), and chlorhexidine were purchased from Sigma-Aldrich (St. Louis, Mo., USA). Albumin-dextrose-catalase (ADC) was from BD Biosciences (San Jose, Calif., USA). The high-throughput screening (HTS) to identify inhibitors of the acetyltransferase activity of purified Eis_Mtb was carried out at the Center for Chemical Genomics (CCG, University of Michigan) against 123,000 compounds from (i) a ChemDiv library (120,000), (ii) the BioFocus NCC library, and (iii) the MicroSource MS2000 library. All small molecules were dissolved in DMSO prior to testing. The immediate follow-up assays to confirm inhibition or triage false positives were performed with hit compounds from fresh powders purchased from ChemDiv (San Diego, Calif., USA). Note: All concentrations noted below are the final concentrations in the assays.

2.2. Eis Chemical Library Screening.

HTS was performed as previously described.[4] Briefly, absorbance signal from the reaction of the enzymatically released CoASH with Ellman's reagent, DTNB, at 412 nm ($\varepsilon_{412}$=14150 $M^{-1}$ $cm^{-1}$) was used to monitor the acetylation by Eis_Mtb. The reactions (40 μL) contained Tris (50 mM, pH 8.0 adjusted at room temperature), Eis (0.25 μM), NEO (100 μM), AcCoA (40 μM), DTNB (0.5 mM), and library compounds (20 μM). Chlorhexidine (5 μM) and DMSO (0.5%) served as positive and negative controls, respectively. Plates were incubated at room temperature and read on a PHERAstar plate reader at 5 min after initiation of the reaction. The average Z' score for the HTS assay was 0.60.

2.3. Hit Validation.

Hit compounds were defined as displaying 3-fold or stronger inhibition than the standard deviation (calculated for the inert compounds) in the HTS. These compounds were tested in triplicate. The compounds that exhibited reproducible inhibitory activity in two out of three trials were then tested in dose-response assays in the concentration range from 20 μM to 78 nM (generated by 2-fold dilutions of the compound stock), and $IC_{50}$ values were obtained for all compounds displaying dose-dependent inhibition.

2.4. Inhibition Kinetics.

Absorbance was measured on a SpectraMax M5 plate reader, for the reaction mixtures in 96-well plates (Thermo Fisher Scientific). Measurements were taken every 30 s for 10 min. Compounds were first serially dissolved in Tris-HCl (50 mM, pH 8.0, containing 10% v/v DMSO). A mixture (50 μL) of Eis (1 μM), KAN (400 μM), and Tris-HCl (50 mM, pH 8.0) was added to the inhibitors and incubated for 10 min. Reactions were initiated by the addition of a mixture (50 μL) of DTNB (8 mM), AcCoA (2 mM), and Tris-HCl (50 mM, pH 8.0). All assays were performed in triplicate. $IC_{50}$ values were calculated by curved fitting to a Hill plot with KaleidaGraph 3.6 software (Table 2 and FIG. 1).

2.5. Inhibitor Selectivity.

To investigate the selectivity of our inhibitors towards Eis, compounds 39 and 46 were tested against three additional AAC enzymes: AAC(2')-Ic, AAC(3)-IV, and AAC(6')-Ie/APH(2")-Ia. The conditions utilized for determination of $IC_{50}$ values were also used here under the optimum conditions for each enzyme. Compounds 39 and 46 (200 to 100 pM) were dissolved in buffer (50 mM MES pH 6.6 for AAC(6')-Ie/APH(2")-Ia and AAC(3)-IV and 100 mM sodium phosphate pH 7.4 for AAC(2')-Ic). Enzyme (0.25 μM for AAC(6')-Ie/APH(2")-Ia, 0.125 μM for AAC(3)-IV and AAC(2')-Ic), NEO (100 μM), and AcCoA (150 μM) were used for these assays. AAC(3)-IV and AAC(2')-Ic experiments were incubated at 25° C. AAC(6')-Ie/APH(2")-Ia experiments were incubated at 37° C. All other methods and concentrations are the same as for the experiments with Eis_Mtb.

2.6. Mycobacterial MIC Determination by Alamar Blue Assay.

Mtb strains H37Rv and K204 were inoculated from frozen stocks into Middlebrook 7H9 broth supplemented with ADC (10%), Tween® 80 (0.05%), and glycerol (0.4%), and incubated at 37° C. until turbidity appeared. The cultures were diluted with fresh 7H9 medium to the attenuance at 600 nm of 0.2, further diluted 1:25 in fresh 7H9 medium in 50 mL polypropylene tubes containing glass beads and vortexed for 30 sec. The cultures were kept still for 10 min, and then 90 μL aliquots were distributed into the wells of a clear 96-well culture plate. Compounds were initially tested at concentrations that were either 100-fold higher than their $IC_{50,KAN}$ or at 100 μM if the $IC_{50}$,KAN value was unknown or could not be achieved while keeping the DMSO concentration ≤1% in test wells. Working stocks for each compound were prepared at concentrations twice that of the desired final concentration in fresh 7H9 medium, and 100 μL of each of these working stocks was added to the 90 μL of bacterial cultures in the wells. The plates were incubated at 37° C. for 24 h in a humid environment before the addition of KAN (10 μL). Growth of H37Rv was evaluated at 2.5, and 1.25 μg/mL KAN while growth of K204 was evaluated at 10, 5, 2.5, and 1.25 μg/mL KAN. The plates were incubated at 37° C. for 6 days after the addition of KAN. Then, 40 μL of alamar blue diluted 1:2 in 10% Tween® 80 was added to each well and the plates continued to be incubated 37° C. The color of each well was preliminarily evaluated 24 h after the addition of alamar blue, with a final evaluation after 48 h. Alamar blue changes from indigo blue to pink as a result of bacterial growth. The lowest concentration of KAN that resulted in no change in color was defined as the MIC for each concentration of an inhibitory compound. Compound screening was carried out on biological replicates in duplicate. Several controls were included with every compound: uninoculated 7H9, compound and inoculated 7H9 only, inoculated 7H9+DMSO only, and inoculated 7H9 only. For each plate, 200 μL of sterile water was added to all perimeter wells to minimize evaporation.

3. Structural Biology:

3.1. Purification of EisC204A.

The active point mutant EisC204A that is less prone to oxidation than the wild-type Eis_Mtb was overexpressed in BL21(DE3) E. coli and purified as previously reported, with only minor modifications, as follows. The EisC204A-pET28a plasmid was transformed into E. coli BL21 (DE3) chemically competent cells and plated onto LB agar containing kanamycin (KAN; 50 μg/mL). After overnight incubation, a single colony from the plate was inoculated into LB broth (5 mL) containing KAN (50 μg/mL) (LB/KAN). This culture was grown at 37° C. until the attenuance at 600 nm of 0.5, then the culture was inoculated into 4 L of LB/KAN and grown at 37° C. At the attenuance at 600 nm of ~0.1, the culture was transferred to 16° C. for 1.5 h, and then IPTG was added at the final concentration of 0.5 mM. The induced culture was grown for an additional 16-18 h at 16° C. with shaking (200 rpm). All following purification steps were done at 4° C. The cells were pelleted by centrifugation at 5,000 rpm for 10 min. The cell pellets were resuspended in chilled lysis buffer (NaCl (300 mM), Tris-HCl pH 8.0 adjusted at room temperature (40 mM), glycerol (10% v/v), and β-mercaptoethanol (2 mM)). The cells were then disrupted by sonication and the insoluble material was removed by centrifugation at 35,000×g for 45 min at 4° C. The supernatant was passed through a 0.45 μm Millex-HV PVDF filter (Millipore, Billerica, Mass., USA) and then loaded onto a 5 mL Ni-IMAC HisTrap FF column (GE Healthcare) pre-equilibrated in the lysis buffer. The column was washed with 100 mL of lysis buffer containing 20 mM imidazole and then the protein was eluted in 10 mL of lysis buffer containing 200 mM imidazole. The eluate was concentrated using an Amicon Ultra-15 (10,000 MWCO) centrifugal filter device (Millipore) to the volume of 5 mL. The protein was then purified on a size-exclusion S-200 column (GE Healthcare) equilibrated in gel filtration buffer (Tris-HCl pH 8.0

(40 mM), NaCl (100 mM), and β-mercaptoethanol (2 mM)). The Eis-containing fractions were pooled and concentrated using an Amicon Ultra (10,000 MWCO) centrifugal filter device (Millipore) to 4 mg/mL. The pure Eis protein was stored on ice at 4° C.

3.2. Crystallization, Diffraction Data Collection, and Structure Determination and Refinement of EisC204A-CoA-Inhibitor 39 Complex.

Crystals were grown by vapor diffusion in hanging drops containing 14 of concentrated (4 mg/mL) EisC204A protein containing KAN (10 mM), and CoA (8 mM) mixed with 1 µL of the reservoir solution (Tris-HCl pH 8.5 adjusted at room temperature (100 mM), PEG 8,000 (10-15% w/v), and $(NH_4)_2SO_4$ (0.4 M)). The drops were equilibrated against 1 mL of the reservoir solution at 22° C. Single crystals were obtained in 2-3 weeks. The crystals were first gradually transferred into the reservoir solution. The $(NH_4)_2SO_4$ and KAN were then exchanged out of the solvent by a gradual transfer into the reservoir solution lacking $(NH_4)_2SO_4$: (Tris-HCl pH 8.5 (100 mM) and PEG 8,000 (13% w/v)). Then the crystals were gradually transferred into the cryoprotectant solution (Tris-HCl pH 8.5 (100 mM), PEG 8,000 (13% w/v), and glycerol (20% v/v)) and incubated in this solution for 10 min. Upon the incubation, the crystals were transferred in the inhibitor solution (the cryoprotectant solution containing 0.5 mM inhibitor) for 30 min, and then frozen in liquid nitrogen by quick immersion.

The X-ray diffraction data were collected at 100 K at synchrotron beamline 22-ID of the Advanced Photon Source at the Argonne National Laboratory (Argonne, Ill.). The data were processed with HKL2000. The crystal form was the same as that of wild-type Eis-CoA-acetamide complex determined previously by our group (PDB code 3R1K) and contained one Eis monomer in the asymmetric unit, with the Eis hexamer generated by crystal symmetry operations. This crystal structure (without ligands or water molecules) was used as the starting point, and rigid body refinement was performed by Refmac, with the Eis monomer as a single rigid-body domain. After the rigid body refinement, strong difference $F_o$-$F_c$ electron density for the inhibitor 39 molecule and a part of CoA was apparent, which allowed building of the molecules into the difference electron density with Coot program. The structures of EisC204A-CoA-inhibitor 39 complex was iteratively built and refined using programs Coot and Refmac, respectively. The data collection and refinement statistics for the structures reported here are given in Table 3. The EisC204A-CoA-inhibitor complex structures have been deposited in the Protein Data Bank. The accession number is 5EBV for the crystal structure of acetyltransferase Eis from *Mycobacterium tuberculosis* in complex with inhibitor 11c and CoA; and the accession number is 5EC4 for the crystal structure of acetyltransferase Eis from *Mycobacterium tuberculosis* in complex with inhibitor 13g and CoA.

Example 2

Protein, Reagents, and Small-Molecule Libraries.

The Eis from Mtb, (1) AAC(6')/APH(2"), (2) AAC(3)-IV, (2) and AAC(2')-Ic(1) were overexpressed and purified as previously reported in the literature. All reagents including 5',5-dithiobis-(2-nitrobenzoic acid) (DTNB), Tween® 80, neomycin B (NEO), kanamycin A (KAN), acetyl-CoA (AcCoA), and chlorhexidine were purchased from Sigma-Aldrich (St. Louis, Mo., USA). Albumin-dextrose-catalase (ADC) was purchased from BD Biosciences (San Jose, Calif., USA). Eis was screened at the Center for Chemical Genomics (CCG, University of Michigan) against 123,000 compounds from (i) a ChemDiv library (120,000), (ii) the BioFocus NCC library, and (iii) the MicroSource MS2000 library. All small molecule stock solutions for HTS were prepared in DMSO. The activity of promising compounds was confirmed using fresh powder samples purchased from ChemDiv (San Diego, Calif., USA). Note: All concentrations noted below are final concentration.

Eis Chemical Library Screening.

Screening of small-molecule libraries was performed as previously described. (3) Briefly, a UV-Vis assay monitoring the reaction of the enzymatically released CoASH with Ellman's reagent, DTNB, at 412 nm ($\varepsilon_{412}$=14150 $M^{-1}$ $cm^{-1}$) was used to determine inhibition of Eis. The final reactions (40 µL) contained Tris (50 mM, pH 8.0 adjusted at room temperature), Eis (0.25 µM), NEO (100 µM), AcCoA (40 µM), DTNB (0.5 mM), and molecules from the HTS libraries (20 µM). Chlorhexidine (5 µM) and DMSO (0.5%) were used as positive and negative controls, respectively. Plates were incubated at room temperature and read on a PHERAstar plate reader at a single end point reading at 5 min after initiation of the reaction. The average Z' score for the entire high-throughput screening assay was 0.60.

Hit Validation.

Compound from the initial screen determined to be hits (>3σ, statistically above the negative control) were tested in triplicate. All compounds inhibiting Eis in two out of three trials were then tested in a dose-dependent manner using two-fold dilutions from 20 µM to 78 nM, and $IC_{50}$ values were determined for all compounds having dose-dependent activity.

Inhibition Kinetics.

All $IC_{50}$ values were determined by UV-Vis assays monitoring CoASH release (see Eis chemical library screening above) by using a Multimode SpectraMax M5 plate reader in 96-well plates. Reactions (200 µL) contained inhibitors (200 µM to 2 pM), Tris (50 mM, pH 8.0 adjusted at room temperature), Eis (0.25 µM), AcCoA (500 µM), KAN (100 µM), and DTNB (2 mM). To calculate $IC_{50}$ values, a Hill plot fit was generated with KaleidaGraph 4.1 software by using the initial rates (first 2-5 min of reactions) normalized to reactions where inhibitors were omitted. $IC_{50}$ values are presented in Table 7 and representative dose-response curves are displayed in FIG. 5.

Inhibitor Selectivity.

Compounds 46b and 46c were tested against three additional AAC enzymes: AAC(6')/APH(2"), AAC(3)-IV, and AAC(2')-Ic. The conditions described above for determination of $IC_{50}$ values were used under the optimum conditions for each enzyme. Compounds 46b and 46c (200 µM to 100 pM) were dissolved in buffer (50 mM MES pH 6.6 for AAC(6')/APH(2") and AAC(3)-IV and 75 mM sodium phosphate pH 7.4 for AAC(2')-Ic). Enzyme (0.25 µM for AAC(6')/APH(2"), 125 nM for AAC(3)-IV and AAC(2')-Ic), NEO (100 µM), and AcCoA (150 µM) were used for these tests. AAC(6')/APH(2") experiments were incubated at 37° C. while AAC(3)-IV and AAC(2')-Ic experiments were incubated at 25° C. All other methods and concentrations remained identical to those for the experiments with Eis.

Mycobacterial MIC Determination by Alamar Blue Assay.

Mtb strains H37Rv and K204 were inoculated from frozen stocks into Middlebrook 7H9 broth supplemented with ADC (10%), Tween® 80 (0.05%), and glycerol (0.4%), and incubated at 37° C. until turbid. Cultures were diluted to an $A_{600}$ of 0.2 in fresh 7H9 medium, then additionally diluted 1:25 in 7H9 medium in 50 mL polypropylene tubes containing glass beads, vortexed for 30 sec, allowed to settle for 10 min, and 90 μL was distributed into wells of a clear 96-well culture plate. Compounds were tested at either 100× their $IC_{50}$ (if known) or 20 μM. Working stocks for each compound were prepared at 2× their desired final test concentration in fresh 7H9 medium, and 100 μL of 2× working stocks was added to test wells containing 90 μL of bacteria. Plates were incubated at 37° C. for 24 h in a humid environment before the addition of KAN (10 μL). Growth of H37Rv was evaluated at 5, 2.5, 1.25, 0.625, 0.312 and 0.156 μg/mL KAN while growth of K204 was evaluated at 20, 10, 5, 2.5, 1.25, 0.625 μg/mL KAN. Plates were incubated at 37° C. for 6 days after the addition of KAN. Then, 40 μL of alamar blue diluted 1:2 in 10% Tween® 80 was added to each well and plates were returned to 37° C. The color of each well was preliminarily evaluated 24 h after the addition of alamar blue, with a final evaluation after 48 h. Alamar blue changes from indigo blue to pink as a result of bacterial growth. The lowest concentration of KAN that resulted in no color change was recorded as the MIC for each concentration of compound. Compound screening was done on biological replicates in triplicate. Several controls were evaluated with every compound including, uninoculated 7H9, compound+inoculated 7H9 only, inoculated 7H9+DMSO only, and inoculated 7H9 only. For each plate, 200 μL of sterile ddH$_2$O was added to all perimeter wells to prevent evaporation.

Purification of EisC204A.

EisC204A was expressed and purified as described, (4) with minor modifications, as follows. The EisC204A-pET28a construct was transformed into *E. coli* BL21 (DE3) chemically competent cells, plated onto LB agar containing kanamycin (KAN; 50 μg/mL). A colony from the transformation plate was inoculated into LB broth (5 mL) supplemented with KAN (50 μg/mL) (LB/KAN) and the culture was grown at 37° C. until mid-log phase. This 5-mL culture was then inoculated into 4 L of LB/KAN and grown at 37° C. When attenuance at 600 nm reached ~0.1, the culture was transferred to 16° C. for ~1.5 h, and then IPTG was added at the final concentration of 0.5 mM. The induced culture was grown for an additional 16-18 h at 16° C. (Note: All culture growth steps were performed with shaking at 200 rpm. All purification steps were carried out at 4° C.). The cells were harvested by centrifugation at 5,000 rpm for 10 min at 4° C. The cell pellets were resuspended in lysis buffer (NaCl (300 mM), Tris-HCl pH 8.0 adjusted at room temperature (40 mM), glycerol (10% v/v), and β-mercaptoethanol (2 mM)). The cells were disrupted by sonication on ice and the insoluble cell debris were removed by centrifugation at 35,000×g for 45 min at 4° C. The supernatant was filtered through a 0.45 μm Millex-HV PVDF filter (Millipore, Billerica, Mass., USA) and applied to a 5 mL Ni-IMAC HisTrap FF column (GE Healthcare) equilibrated with lysis buffer. The protein was then eluted with lysis buffer in a stepwise imidazole gradient (6×5 mL fractions of 10 mM imidazole, 6×5 mL fractions of 20 mM imidazole, 3×5 mL fractions of 50 mM imidazole, and 7×5 mL fractions of 250 mM imidazole). The eluted fractions containing more than 95% pure desired protein, as determined by SDS-PAGE, were pooled and concentrated using an Amicon Ultra-15 (5,000 MWCO) centrifugal filter device (Millipore). The protein was further purified on a size-exclusion S-200 column (GE Healthcare) equilibrated in gel filtration buffer (Tris-HCl pH 8.0 (40 mM), NaCl (100 mM), and β-mercaptoethanol (2 mM)), and the Eis-containing fractions were pooled and concentrated using an Amicon Ultra (5,000 MWCO) centrifugal filter device (Millipore) to 4 mg/mL. The pure Eis protein was stored at 4° C.

Crystallization, Diffraction Data Collection, and Structure Determination and Refinement of EisC204A-CoA-Inhibitor Complexes.

Crystals were grown by vapor diffusion in hanging drops containing 1 μL of concentrated (4 mg/mL) EisC204A protein, KAN (10 mM), and CoA (8 mM) mixed with 1 μIL of the reservoir solution (Tris-HCl pH 8.5 adjusted at room temperature (100 mM), PEG 8,000 (10-15% w/v), and (NH$_4$)$_2$SO$_4$ (0.4 M)) equilibrated against 1 mL of the reservoir solution at 22° C. Single crystals were obtained in 2-3 weeks. The crystals were first gradually transferred into the reservoir solution. The (NH$_4$)$_2$SO$_4$ and KAN were exchanged out of the crystals by a gradual transfer into the reservoir solution lacking (NH$_4$)$_2$SO$_4$ (Tris-HCl pH 8.5 (100 mM) and PEG 8,000 (13% w/v)). CoA remained stably bound to Eis during this procedure. Then the crystals were gradually transferred into the cryoprotectant solution (Tris-HCl pH 8.5 (100 mM), PEG 8,000 (13% w/v), and glycerol (20% v/v)). After this transfer, the crystals were soaked in the inhibitor solution (the cryoprotectant solution containing 0.5 mM inhibitor) for 30 min, then rapidly frozen in liquid nitrogen.

The diffraction data were collected at synchrotron beamline 22-ID of the Advanced Photon Source at the Argonne National Laboratory (Argonne, Ill.) at 100 K. The data were indexed, integrated and scaled with HKL2000. The crystal form coincided with that of wild-type Eis-CoA-acetamide complex determined previously by our group (PDB code 3R1K(1)). The Eis from this structure was the starting point, and performed rigid body refinement by Refmac. After rigid body refinement, strong difference $F_o$-$F_c$ electron density for an inhibitor molecule and a part of CoA was apparent, which allowed facile building of these molecules by using Coot. The structures of EisC204A-CoA-inhibitor complexes were iteratively built and refined using programs Coot and Refmac, respectively. The data collection and refinement statistics for the structures reported here are given in Table 8. The EisC204A-CoA-inhibitor 11c and 13g structures were deposited in the Protein Data Bank with the PDB accession numbers 5EBV and 5EC4, respectively.

TABLE 8

X-ray diffraction data collection and refinement statistics for the EisC204A-CoA-inhibitor 11c and EisC204A-CoA-inhibitor 13g ternary complex structures.

| Data collection | 11c | 13g |
| --- | --- | --- |
| Space group | R3$_2$ | R3$_2$ |
| Number of monomers per asymmetric unit | 1 | 1 |
| Unit cell dimensions | | |
| a, b, c (Å) | 175.2, 175.2, 122.3 | 175.6, 175.6, 122.2 |
| a, b, g (*) | 90, 90, 120 | 90, 90, 120 |
| Resolution (Å) | 50.0-2.2 (2.24-2.20)$^a$ | 50.0-2.2 (2.24-2.20)$^a$ |
| I/s | 21 (2.9) | 24 (4.0) |

TABLE 8-continued

X-ray diffraction data collection and refinement statistics for the
EisC204A-CoA-inhibitor 11c and EisC204A-CoA-inhibitor 13g ternary
complex structures.

| | | |
|---|---|---|
| Completeness (%) | 99.9 (100) | 99.8 (99.4) |
| Redundancy | 9.5 (9.4) | 7.3 (7.3) |
| $R_{merge}$ | 0.11 (0.62) | 0.10 (0.56) |
| Number of unique reflections | 34,661 | 34,541 |
| Structure refinement statistics | | |
| Resolution (Å) | 40.0-2.2 | 40.0-2.2 |
| R (%) | 19.4 | 20.0 |
| $R_{free}$ (%) | 21.5 | 23.8 |
| Bond length deviation (rmsd) from ideal (Å) | 0.006 | 0.007 |
| Bond angle deviation (rmsd) from ideal (°) | 1.34 | 1.46 |
| Ramachandran plot statistics[b] | | |
| % of residues in most allowed regions | 94.1 | 93.2 |
| % of residues in additional allowed regions | 5.9 | 6.8 |
| % of residues in generously allowed regions | 0.0 | 0.0 |
| % of residues in disallowed regions | 0.0 (0 residues) | 0.0 (0 residues) |

[a]Numbers in parentheses indicate the values in the highest-resolution shell.
[b]Indicates Procheck statistics. (8)

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the present disclosure can be changed without departing from the scope of the subject matter disclosed herein. Furthermore, the foregoing description is for the purpose of illustration only, and not for the purpose of limitation.

Throughout this document, various references are mentioned. All such references are incorporated herein by reference, including the references set forth in the following list:

1. World Health Organization (2014) Global tuberculosis report 2014. ISBM 978 992 974 156580 156589.
2. Zaunbrecher M A, Sikes R D, Jr., Metchock B, Shinnick T M, & Posey J E (2009) Overexpression of the chromosomally encoded aminoglycoside acetyltransferase eis confers kanamycin resistance in *Mycobacterium tuberculosis*. *Proc Natl Acad Sci USA* 106(47):20004-20009.
3. Campbell P J, et al. (2011) Molecular detection of mutations associated with first- and second-line drug resistance compared with conventional drug susceptibility testing of *Mycobacterium tuberculosis*. *Antimicrob Agents Chemother* 55(5):2032-2041.
4. Jnawali H N, et al. (2013) Molecular genetics of *Mycobacterium tuberculosis* resistant to aminoglycosides and cyclic peptide capreomycin antibiotics in Korea. *World J Microbiol Biotechnol* 29(6):975-982.
5. Chen W, Biswas T, Porter V R, Tsodikov O V, & Garneau-Tsodikova S (2011) Unusual regioversatility of acetyltransferase Eis, a cause of drug resistance in XDR-TB. *Proc Natl Acad Sci USA* 108(24):9804-9808.
6. Tsodikov O V, Green K D, & Garneau-Tsodikova S (2014) A random sequential mechanism of aminoglycoside acetylation by *Mycobacterium tuberculosis* Eis protein. *PLoS One* 9(4):e92370.
7. Houghton J L, Biswas T, Chen W, Tsodikov O V, & Garneau-Tsodikova S (2013) Chemical and structural insights into the regioversatility of the aminoglycoside acetyltransferase Eis. *ChemBioChem* 14(16):2127-2135.
8. Chen W, Green K D, Tsodikov O V, & Garneau-Tsodikova S (2012) Aminoglycoside multiacetylating activity of the enhanced intracellular survival protein from *Mycobacterium smegmatis* and its inhibition. *Biochemistry* 51(24): 4959-4967.
9. Green K D, Pricer R E, Stewart M N, & Garneau-Tsodikova S (2015) Comparative study of Eis-like enzymes from pathogenic and non-pagthogenic bacteria. *ACS Infect Dis* 1(6):272-283.
10. Pricer R E, Houghton J L, Green K D, Mayhoub A S, & Garneau-Tsodikova S (2012) Biochemical and structural analysis of aminoglycoside acetyltransferase Eis from *Anabaena variabilis*. *Mol BioSyst* 8(12):3305-3313.
11. Green K D, et al. (2015) Biochemical and structural analysis of an Eis family aminoglycoside acetyltransferase from *Bacillus anthracis*. Biochemistry 54(20): 3197-3206.
12. Green K D, Chen W, & Garneau-Tsodikova S (2012) Identification and characterization of inhibitors of the aminoglycoside resistance acetyltransferase Eis from *Mycobacterium tuberculosis*. *ChemMedChem* 7(1):73-77.
13. Chen W, Green K D, & Garneau-Tsodikova S (2012) Cosubstrate tolerance of the aminoglycoside resistance enzyme Eis from *Mycobacterium tuberculosis*. *Antimicrob Agents Chemother* 56(11):5831-5838.
14. Houghton J L, Green K D, Pricer R E, Mayhoub A S, & Garneau-Tsodikova S (2013) Unexpected N-acetylation of capreomycin by mycobacterial Eis enzymes. *J Antimicrob Chemother* 68(4):800-805.
15. Yoon H J, et al. (2013) A docking study of enhanced intracellular survival protein from *Mycobacterium tuberculosis* with human DUSP16/MKP-7. *J Synchrotron Radiat* 20(Pt 6):929-932.
16. Hugonnet J E, Tremblay L W, Boshoff H I, Barry C E, 3rd, & Blanchard J S (2009) Meropenem-clavulanate is effective against extensively drug-resistant *Mycobacterium tuberculosis*. *Science* 323(5918):1215-1218.
17. Ainsa J A, et al. (1997) Aminoglycoside 2'-N-acetyltransferase genes are universally present in mycobacteria: characterization of the aac(2')-Ic gene from *Mycobacte-*

*rium tuberculosis* and the aac(2')-Id gene from *Mycobacterium smegmatis*. *Mol Microbiol* 24(2):431-441.
18. Vetting M W, Hegde S S, Javid-Majd F, Blanchard J S, & Roderick S L (2002) Aminoglycoside 2'-N-acetyltransferase from *Mycobacterium tuberculosis* in complex with coenzyme A and aminoglycoside substrates. *Nat Struct Biol* 9(9):653-658.
19. Green K D, Chen W, Houghton J L, Fridman M, & Garneau-Tsodikova S (2010) Exploring the substrate promiscuity of drug-modifying enzymes for the chemoenzymatic generation of N-acylated aminoglycosides. *ChemBioChem* 11(1):119-126.
20. Magalhaes M L & Blanchard J S (2005) The kinetic mechanism of AAC3-IV aminoglycoside acetyltransferase from *Escherichia coli*. *Biochemistry* 44(49):16275-16283.
21. Boehr D D, Daigle D M, & Wright G D (2004) Domain-domain interactions in the aminoglycoside antibiotic resistance enzyme AAC(6')-APH(2"). *Biochemistry* 43(30):9846-9855.
22. Caldwell S J & Berghuis A M (2012) Small-angle X-ray scattering analysis of the bifunctional antibiotic resistance enzyme aminoglycoside (6') acetyltransferase-Ie/aminoglycoside (2") phosphotransferase-Ia reveals a rigid solution structure. *Antimicrob Agents Chemother* 56(4):1899-1906.
23. Laskowski R A, Macarthur M W, Moss D S, & Thornton J M (1993) Procheck—a program to check the stereochemical quality of protein structures. *J Appl Cryst* 26:283-291.
24. World Health Organization (2014) Global tuberculosis report 2014. ISBM 978 992 974 156580 156589.
25. Green K D & Garneau-Tsodikova S (2013) Resistance in tuberculosis: what do we know and where can we go? *Front. Microbiol.* 4:208.
26. Campbell P J, et al. (2011) Molecular detection of mutations associated with first- and second-line drug resistance compared with conventional drug susceptibility testing of *Mycobacterium tuberculosis*. *Antimicrob. Agents Chemother.* 55(5):2032-2041.
27. Chen W, Biswas T, Porter V R, Tsodikov O V, & Garneau-Tsodikova S (2011) Unusual regioversatility of acetyltransferase Eis, a cause of drug resistance in XDR-TB. *Proc. Natl. Acad. Sci., U.S.A.* 108(24):9804-9808.
28. Chen W, Green K D, Tsodikov O V, & Garneau-Tsodikova S (2012) Aminoglycoside multiacetylating activity of the enhanced intracellular survival protein from *Mycobacterium smegmatis* and its inhibition. *Biochemistry* 51(24):4959-4967.
29. Chen W, Green K D, & Garneau-Tsodikova S (2012) Cosubstrate tolerance of the aminoglycoside resistance enzyme Eis from *Mycobacterium tuberculosis*. *Antimicrob. Agents Chemother.* 56(11):5831-5838.
30. Houghton J L, Green K D, Pricer R E, Mayhoub A S, & Garneau-Tsodikova S (2013) Unexpected N-acetylation of capreomycin by mycobacterial Eis enzymes. *J. Antimicrob. Chemother.* 68(4):800-805.
31. Jennings B C, Labby K J, Green K D, & Garneau-Tsodikova S (2013) Redesign of substrate specificity and identification of the aminoglycoside binding residues of Eis from *Mycobacterium tuberculosis*. *Biochemistry* 52(30):5125-5132.
32. Tsodikov O V, Green K D, & Garneau-Tsodikova S (2014) A random sequential mechanism of aminoglycoside acetylation by *Mycobacterium tuberculosis* Eis protein. *PloS one* 9(4):e92370.
33. Houghton J L, Biswas T, Chen W, Tsodikov O V, & Garneau-Tsodikova S (2013) Chemical and structural insights into the regioversatility of the aminoglycoside acetyltransferase Eis. *ChemBioChem* 14(16):2127-2135.
34. Pricer R E, Houghton J L, Green K D, Mayhoub A S, & Garneau-Tsodikova S (2012) Biochemical and structural analysis of aminoglycoside acetyltransferase Eis from *Anabaena variabilis*. *Mol. BioSyst.* 8(12):3305-3313.
35. Green K D, et al. (2015) Biochemical and structural analysis of an Eis family aminoglycoside acetyltransferase from *Bacillus anthracis*. *Biochemistry* 54(20):3197-3206.
36. Green K D, Pricer R E, Stewart M N, & Garneau-Tsodikova S (2015) Comparative study of Eis-like enzymes from pathogenic and non-pathogenic bacteria. *ACS Infec. Dis.* 1(6):272-283.
37. Hugonnet J E, Tremblay L W, Boshoff H I, Barry C E, 3rd, & Blanchard J S (2009) Meropenem-clavulanate is effective against extensively drug-resistant *Mycobacterium tuberculosis*. *Science* 323(5918):1215-1218.
38. Zhang J, et al. (2014) Non-antibiotic agent ginsenoside 20(S)-Rh2 enhanced the antibacterial effects of ciprofloxacin in vitro and in vivo as a potential NorA inhibitor. *Eur. J. Pharmacol.* 740:277-284.
39. Shlaes D M (2013) New beta-lactam-beta-lactamase inhibitor combinations in clinical development. *Ann. New York Acad. Sci.* 1277:105-114.
40. Zhanel G G, et al. (2013) Ceftazidime-avibactam: a novel cephalosporin/beta-lactamase inhibitor combination. *Drugs* 73(2):159-177.
41. Sader H S, Castanheira M, Flamm R K, Farrell D J, & Jones R N (2014) Antimicrobial activity of ceftazidime-avibactam against Gram-negative organisms collected from U.S. medical centers in 2012. *Antimicrob. Agents Chemother.* 58(3):1684-1692.
42. Gao F, Yan X, & Auclair K (2009) Synthesis of a phosphonate-linked aminoglycoside-coenzyme a bisubstrate and use in mechanistic studies of an enzyme involved in aminoglycoside resistance. *Chemistry* 15(9):2064-2070.
43. Gao F, Yan X, Baettig O M, Berghuis A M, & Auclair K (2005) Regio- and chemoselective 6'-N-derivatization of aminoglycosides: bisubstrate inhibitors as probes to study aminoglycoside 6'-N-acetyltransferases. *Angew. Chem.* 44(42):6859-6862.
44. Gao F, et al. (2006) Synthesis and structure-activity relationships of truncated bisubstrate inhibitors of aminoglycoside 6'-N-acetyltransferases. *J. Med. Chem.* 49(17):5273-5281.
45. Gao F, et al. (2008) Synthesis and use of sulfonamide-, sulfoxide-, or sulfone-containing aminoglycoside-CoA bisubstrates as mechanistic probes for aminoglycoside N-6'-acetyltransferase. *Bioorg. Med. Chem. Lett.* 18(20):5518-5522.
46. Boehr D D, et al. (2003) Broad-spectrum peptide inhibitors of aminoglycoside antibiotic resistance enzymes. *Chem. Biol.* 10(2):189-196.
47. Suga T, et al. (2012) Aranorosin circumvents arbekacin-resistance in MRSA by inhibiting the bifunctional enzyme AAC(6')/APH(2"). *J. Antibiot.* 65(10):527-529.
48. Green K D, Chen W, & Garneau-Tsodikova S (2012) Identification and characterization of inhibitors of the aminoglycoside resistance acetyltransferase Eis from *Mycobacterium tuberculosis*. *ChemMedChem* 7(1):73-77.

49. Boehr D D, Daigle D M, & Wright G D (2004) Domain-domain interactions in the aminoglycoside antibiotic resistance enzyme AAC(6')-APH(2"). *Biochemistry* 43(30):9846-9855.
50. Caldwell S J & Berghuis A M (2012) Small-angle X-ray scattering analysis of the bifunctional antibiotic resistance enzyme aminoglycoside (6') acetyltransferase-Ie/aminoglycoside (2") phosphotransferase-Ia reveals a rigid solution structure. *Antimicrob. Agents Chemother.* 56(4): 1899-1906.
51. Magalhaes M L & Blanchard J S (2005) The kinetic mechanism of AAC3-IV aminoglycoside acetyltransferase from *Escherichia coli. Biochemistry* 44(49):16275-16283.
52. Ainsa J A, et al. (1997) Aminoglycoside 2'-N-acetyltransferase genes are universally present in mycobacteria: characterization of the aac(2)-Ic gene from *Mycobacterium tuberculosis* and the aac(2')-Id gene from *Mycobacterium smegmatis. Mol. Microbiol.* 24(2):431-441.
53. Vetting M W, Hegde S S, Javid-Majd F, Blanchard J S, & Roderick S L (2002) Aminoglycoside 2'-N-acetyltransferase from *Mycobacterium tuberculosis* in complex with coenzyme A and aminoglycoside substrates. *Nat. Struct. Biol.* 9(9):653-658.
54. Agafonov R V, Wilson C, Otten R, Buosi V, & Kern D (2014) Energetic dissection of Gleevec's selectivity toward human tyrosine kinases. *Nat. Struct. Mol. Biol.* 21(10):848-853.
55. Mainardi J L, et al. (1994) Activity of isepamicin and selection of permeability mutants to beta-lactams during aminoglycoside therapy of experimental endocarditis due to *Klebsiella-pneumoniae*-Cf104 producing an aminoglycoside acetyltransferase 6' modifying enzyme and a Tem-3 beta-lactamase. *J. Infect. Dis.* 169(6):1318-1324.
56. Stoesser N, et al. (2013) Predicting antimicrobial susceptibilities for *Escherichia coli* and *Klebsiella pneumoniae* isolates using whole genomic sequence data. *J. Antimicrob. Chemother.* 68(10):2234-2244.
57. Filippa N, et al. (2013) Outbreak of multidrug-resistant *Klebsiella pneumoniae* carrying qnrB1 and bla(CTX-M15) in a French intensive care unit. *Ann. Intensive Care* 3:18.
58. Green K D, Chen W, Houghton J L, Fridman M, & Garneau-Tsodikova S (2010) Exploring the substrate promiscuity of drug-modifying enzymes for the chemoenzymatic generation of N-acylated aminoglycosides. *ChemBioChem* 11(1):119-126.
59. Obamefi C, Akinpelu D. Synthesis and antimicrobial activity of some 2(1H)-quinoxaline-6-sulfonyl derivatives. *Phosphorus Sulfur Silicon Relat. Elem.* 180(8): 1795-1807 (2005)
60. Chen W, Biswas T, Porter V R, Tsodikov O V, Garneau-Tsodikova S. Unusual regioversatility of acetyltransferase Eis, a cause of drug resistance in XDR-TB. *Proc. Natl. Acad. Sci., U.S.A.* 108(24):9804-9808 (2011)
61. Green K D, Chen W, Houghton J L, Fridman M, Garneau-Tsodikova S. Exploring the substrate promiscuity of drug-modifying enzymes for the chemoenzymatic generation of N-acylated aminoglycosides. *ChemBioChem.* 11(1):119-126 (2010)
62. Green K D, Chen W, Garneau-Tsodikova S. Identification and characterization of inhibitors of the aminoglycoside resistance acetyltransferase Eis from *Mycobacterium tuberculosis. ChemMedChem.* 7(1):73-77 (2012)
63. Houghton J L, Biswas T, Chen W, Tsodikov O V, Garneau-Tsodikova S. Chemical and structural insights into the regioversatility of the aminoglycoside acetyltransferase Eis. *ChemBioChem.* 14(16):2127-2135 (2013)
64. Otwinowski Z, Minor W. Processing of X-ray diffraction data collected in oscillation mode. *Met. Enzymol. Macromol. Crystallogr.* 276:307-326 (1997)
65. Murshudov G N, Vagin A A, Dodson E J. Refinement of macromolecular structures by the maximum-likelihood method. *Acta Cryst. Section D.* 53(Pt 3):240-255 (1997)
66. Emsley P, Cowtan K. Coot: model-building tools for molecular graphics. *Acta Cryst. Section D.* 60(Pt 12 Pt 1):2126-2132 (2004)
67. Chen W, Biswas T, Porter V R, Tsodikov O V, & Garneau-Tsodikova S (2011) Unusual regioversatility of acetyltransferase Eis, a cause of drug resistance in XDR-TB. *Proc. Natl. Acad. Sci., U.S.A.* 108(24):9804-9808.
68. Green K D, Chen W, Houghton J L, Fridman M, & Garneau-Tsodikova S (2010) Exploring the substrate promiscuity of drug-modifying enzymes for the chemoenzymatic generation of N-acylated aminoglycosides. *ChemBioChem.* 11(1):119-126.
69. Green K D, Chen W, & Garneau-Tsodikova S (2012) Identification and characterization of inhibitors of the aminoglycoside resistance acetyltransferase Eis from *Mycobacterium tuberculosis. ChemMedChem* 7(1):73-77.
70. Houghton J L, Biswas T, Chen W, Tsodikov O V, & Garneau-Tsodikova S (2013) Chemical and structural insights into the regioversatility of the aminoglycoside acetyltransferase Eis. *ChemBioChem* 14(16):2127-2135.
71. Otwinowski Z & Minor W (1997) Processing of X-ray diffraction data collected in oscillation mode. *Methods Enzymol. Macromol. Crystallogr. A* 276:307-326.
72. Murshudov G N, Vagin A A, & Dodson E J (1997) Refinement of macromolecular structures by the maximum-likelihood method. *Acta Crystallogr. D* 53(Pt 3):240-255.
73. Emsley P & Cowtan K (2004) Coot: model-building tools for molecular graphics. *Acta Crystallogr. D* 60(Pt 12 Pt 1):2126-2132.
74. Laskowski R A, Macarthur M W, Moss D S, & Thornton J M (1993) Procheck—a program to check the stereochemical quality of protein structures. *J. Appl. Cryst.* 26:283-291.

What is claimed is:
1. A compound of the formula:

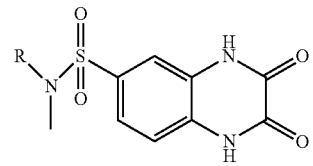

wherein R is selected from the group consisting of

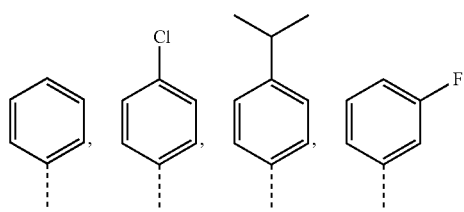

-continued

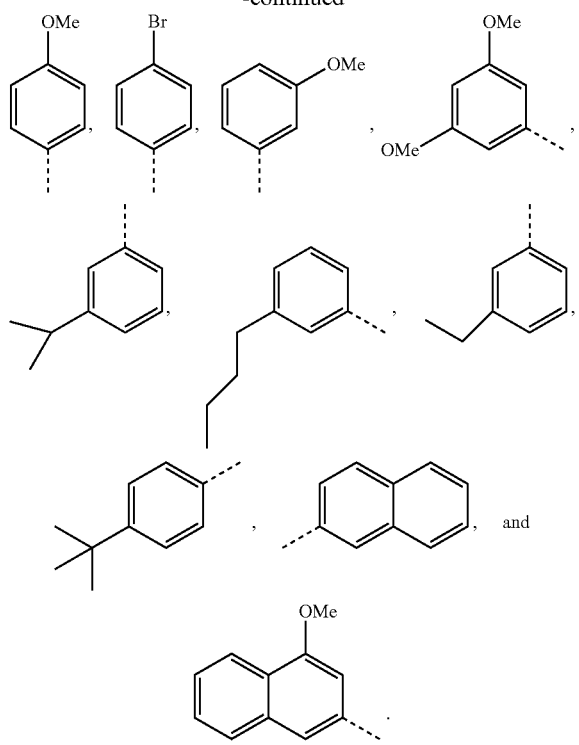

2. A pharmaceutical composition comprising the compound of claim 1, and a suitable pharmaceutical carrier.

3. The composition of claim 2, and further comprising an aminoglycoside.

4. The composition of claim 3, wherein the aminoglycoside is kanamycin (KAN).

5. A method of inhibiting Eis comprising administering to a subject an effective amount of a composition comprising a compound according to the formula

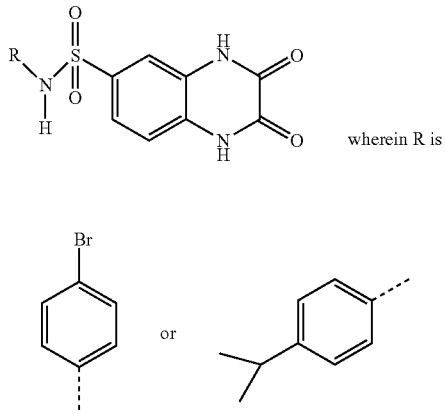

wherein R is or a compound of claim 1.

6. A method of inhibiting Eis comprising administering an effective amount of a composition comprising a compound according to the formula:

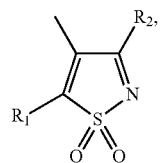

wherein
R1 is selected from:

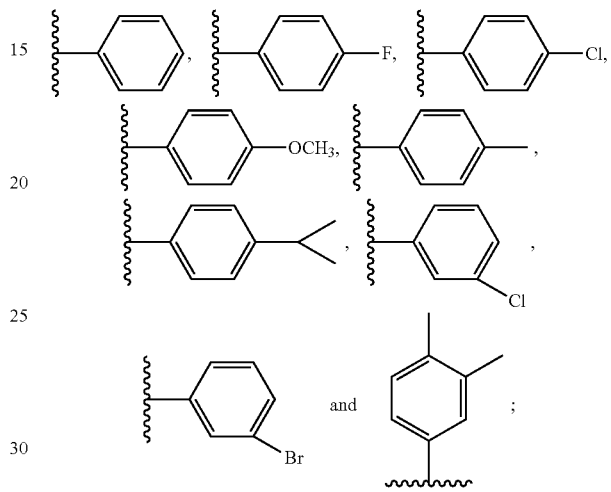

R2 is selected from:

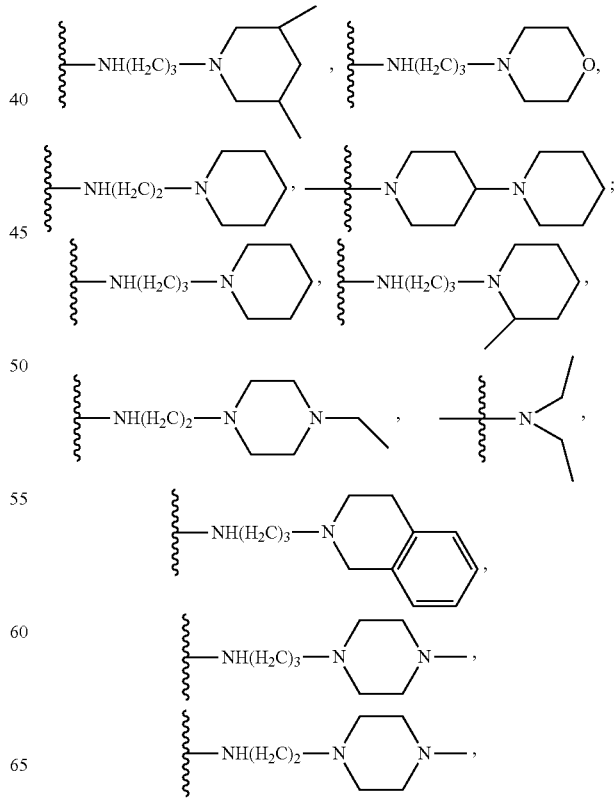

-continued
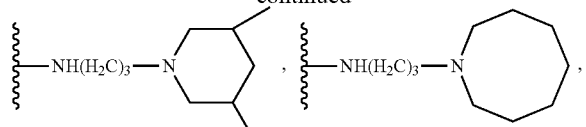
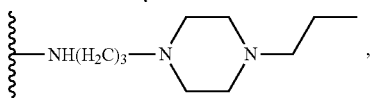
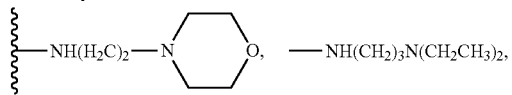
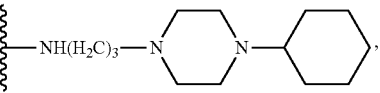
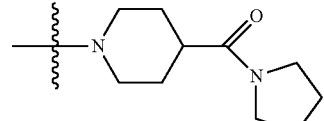
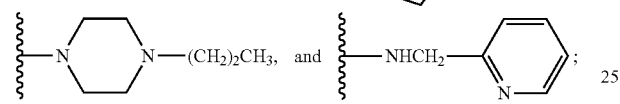
and
when R1 is
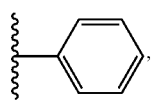
R2 is
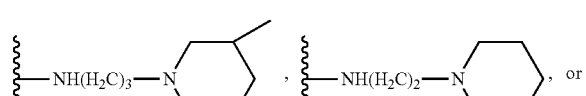
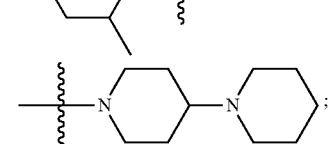
when R1 is
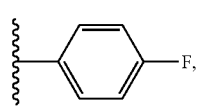 [SMILES: *c1ccc(F)cc1]
R2 is
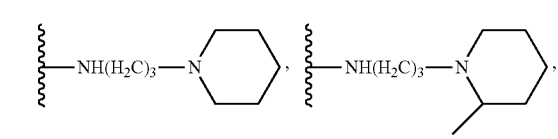 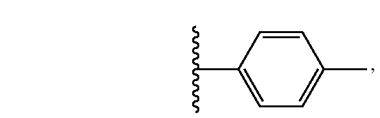 [SMILES: *c1ccc(C)cc1]
-continued
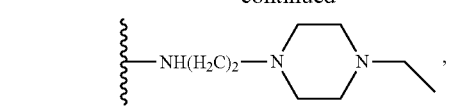
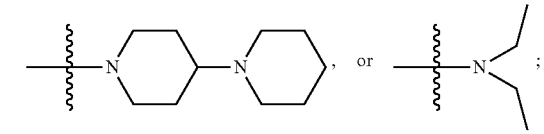
when R1 is
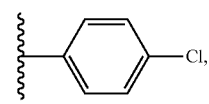
R2 is
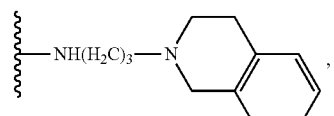
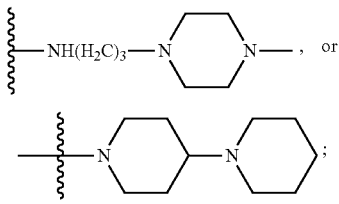
when R1 is
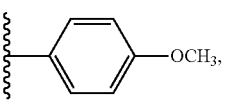
R2 is
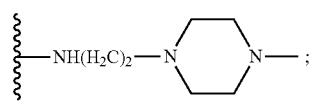
when R1 is
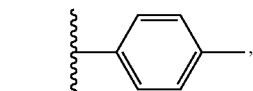

R2 is
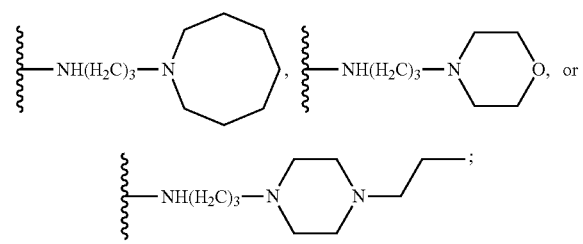
when R1 is
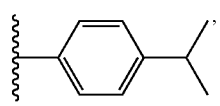
R2 is
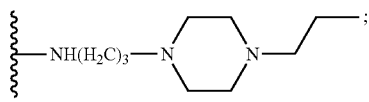
when R1 is
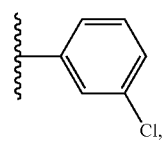 [SMILES: *c1cccc(Br)c1]
R2 is
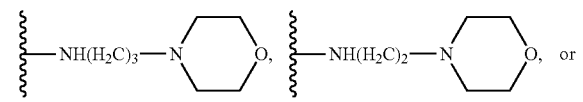
when R1 is
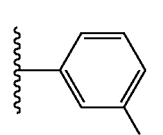
R2 is
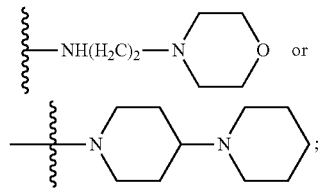
and
when R1 is
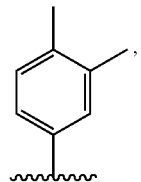 [SMILES: *c1ccc(C)c(C)c1]
R2 is —NH(CH₂)₃N(CH₂CH₃)₂,
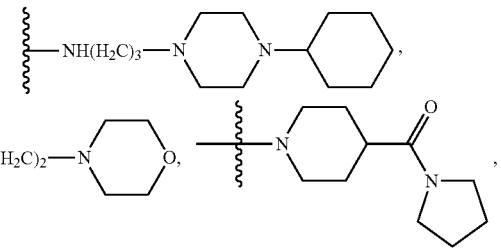
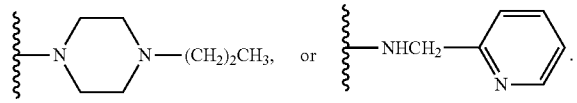
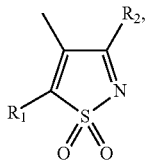
7. The method of claim 6, wherein the compound is according to the formula:
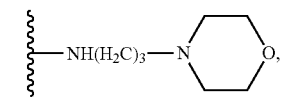
wherein R1 is
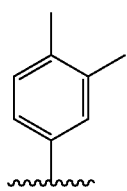

and R2 is —NH(CH$_2$)$_3$N(CH$_2$CH$_3$)$_2$; R1 is

[structure: 3-chlorophenyl]

and R2 is

[structure: —NH(H$_2$C)$_3$—N-morpholinyl], or R1 is

[structure: 4-chlorophenyl] and [structure: —NH(H$_2$C)$_3$—N-tetrahydroisoquinolinyl].

8. The method claim 5, wherein a MIC$_{KAN}$ value is less than about 0.625 μg/mL for *Mycobacterium tuberculosis* (Mtb) strain H37Rv or less than about 5 μg/mL for Mtb strain K204.

9. The method of claim 5, further comprising administering an aminoglycoside.

10. The method of claim 9, wherein the aminoglycoside is kanamycin (KAN).

11. A method of treating aminoglycoside-resistant *Mycobacterium tuberculosis* (Mtb), comprising administering the compound of claim 1 to a subject.

12. The method of claim 11, further comprising administering an aminoglycoside.

13. The method of claim 12, wherein the aminoglycoside is kanamycin (KAN).

14. The method of claim 12, wherein the aminoglycoside is administered to a subject in need of treatment for aminoglycoside-resistant Mtb.

15. A kit comprising the compound of claim 1, packaged together with an aminoglycoside.

16. The kit of claim 15, wherein the aminoglycoside is kanamycin (KAN).

* * * * *